US008109865B2

(12) United States Patent  (10) Patent No.: US 8,109,865 B2
Jackson  (45) Date of Patent: Feb. 7, 2012

(54) ANTIPROTON PRODUCTION AND DELIVERY FOR IMAGING AND TERMINATION OF UNDESIRABLE CELLS

(75) Inventor: Gerald Peter Jackson, West Chicago, IL (US)

(73) Assignee: Hbar Technologies, LLC, West Chicago, IL (US)

( * ) Notice: Subject to any disclaimer, the term of this patent is extended or adjusted under 35 U.S.C. 154(b) by 446 days.

(21) Appl. No.: 11/702,950

(22) Filed: Feb. 5, 2007

(65) Prior Publication Data

US 2007/0225603 A1    Sep. 27, 2007

Related U.S. Application Data

(63) Continuation-in-part of application No. 10/479,272, filed as application No. PCT/US02/27796 on Aug. 29, 2002, now abandoned.

(60) Provisional application No. 60/316,711, filed on Aug. 30, 2001, provisional application No. 60/370,605, filed on Apr. 5, 2002, provisional application No. 60/382,042, filed on May 20, 2002, provisional application No. 60/388,428, filed on May 29, 2002.

(51) Int. Cl.
 *A61N 5/00* (2006.01)

(52) U.S. Cl. ........................................................... 600/1

(58) Field of Classification Search .................. 600/1, 2, 600/411; 378/65, 145, 150, 165, 17; 324/318; 250/493.1, 503.1, 281, 282, 292, 424, 306, 250/307
See application file for complete search history.

(56) References Cited

U.S. PATENT DOCUMENTS

| | | | |
|---|---|---|---|
| 4,491,948 A | 1/1985 | Deacon et al. | 372/2 |
| 5,001,437 A | 3/1991 | Miyata et al. | 328/235 |
| 5,051,600 A * | 9/1991 | Schuetz et al. | 250/492.3 |
| 5,073,913 A | 12/1991 | Martin | 378/34 |
| 5,138,271 A | 8/1992 | Ikegami | 328/233 |
| 5,339,812 A * | 8/1994 | Hardy et al. | 600/429 |
| 5,557,178 A | 9/1996 | Talman | 315/501 |
| 5,895,926 A * | 4/1999 | Britton et al. | 250/492.3 |
| 5,977,554 A * | 11/1999 | Smith et al. | 250/493.1 |
| 6,160,263 A | 12/2000 | Smith et al. | 250/493.1 |
| 6,198,957 B1* | 3/2001 | Green | 600/411 |
| 6,265,837 B1 | 7/2001 | Akiyama et al. | 315/503 |
| 6,414,331 B1 | 7/2002 | Smith et al. | 250/493.1 |
| 6,576,916 B2 | 6/2003 | Smith et al. | 250/493.1 |
| 6,606,370 B1 | 8/2003 | Kasprowicz | 376/913 |
| 6,815,688 B2* | 11/2004 | Schneiker et al. | 250/396 R |
| 2003/0183783 A1 | 10/2003 | Smith et al. | 250/493.1 |
| 2004/0096033 A1* | 5/2004 | Seppi et al. | 378/65 |

OTHER PUBLICATIONS

"Amendment A" filed Mar. 13, 2009, for U.S. Appl. No. 11/603,313, titled Deceleration of Hadron Beams in Synchrotrons Designed for Acceleration. pp. 1-16.
U.S. Appl. No. 60/316,711, filed Aug. 30, 2001, Howe.
U.S. Appl. No. 60/370,605, filed Apr. 5, 2002, Jackson.
U.S. Appl. No. 60/382,042, filed May 20, 2002, Jackson.

(Continued)

*Primary Examiner* — Samuel G Gilbert
(74) *Attorney, Agent, or Firm* — Peter K. Trzyna, Esq.

(57) ABSTRACT

Systems and methods for using antiprotons for terminating unwanted or undesirable cells which can be used in the treatment of conditions caused by the existence and/or proliferation of such undesirable cells. Such conditions include cardiovascular ailments, Parkinson's disease, wet macular degeneration, endocrine disorders, dermatological ailments, and cancer. Because of the unique nature of antiprotons and their annihilation characteristics, the preferred antiproton delivery device (1010, 1015, 1030) embodiments further incorporate detector arrays (1050*a*), capable of detecting characteristic emissions in the course of treatment.

10 Claims, 19 Drawing Sheets

OTHER PUBLICATIONS

U.S. Appl. No. 60/388,428, filed Aug. 29, 2002, Maggiore.
U.S. Appl. No. 60/731,971, filed Oct. 31, 2005, Jackson.
U.S. Appl. No. 60/734,126, filed Nov. 7, 2005, Jackson.
U.S. Appl. No. 60/735,108, filed Nov. 9, 2005, Jackson.
U. Oelfke, G.K.Y. Lam, & M.S. Atkins. Proton Dose Monitoring with PET: Quantitative Studies in Lucite. Received Jun. 29, 1995. 20 pages.
"Fermilab Low Energy Antiproton Home Page." Last edited by Gerry Jackson (gpj @fnal.gov) on Oct. 14, 2000. pp. 1-34.
File History for U.S. Appl. No. 10/479,272, filed Dec. 1, 2003, and File History for PCT/US02/27796, filed Aug. 29, 2002. pp. 1-227.
"Improper Change of Inventorship by International Bureau" letter dated Nov. 20, 2006, to WIPO, and WIPO's "Communication in Cases for Which No Other Form is Applicable" letter dated Jan. 26, 2007, stating that the "removal of inventors Steve Howe and Gerald Jackson was issued in error." pp. 1-4.
R.A. Lewis, G.A. Smith, and S.D. Howe, "Antiproton Portable Traps and Medical Applications", Hyperfine Interactions, vol. 109 (1997) 155.
Gray, L., and Kalogeropoulos, T. E. "Possible Biomedical Applications of Antiproton Beams: Focused Radiation Transfer" Radiat. Res. 97, 246-252 (1984).
Sullivan, A.H., "A Measurement of the Local Energy Deposition by Antiprotons Coming to Rest in Tissue-Like Material," Phys. Med. Biol., 1985, vol. 30, No. 12, 1297-1303. CERN, Geneva, Switzerland.

\* cited by examiner

DIAGRAM OF AN ANTIPROTON ANNIHILATION EVENT

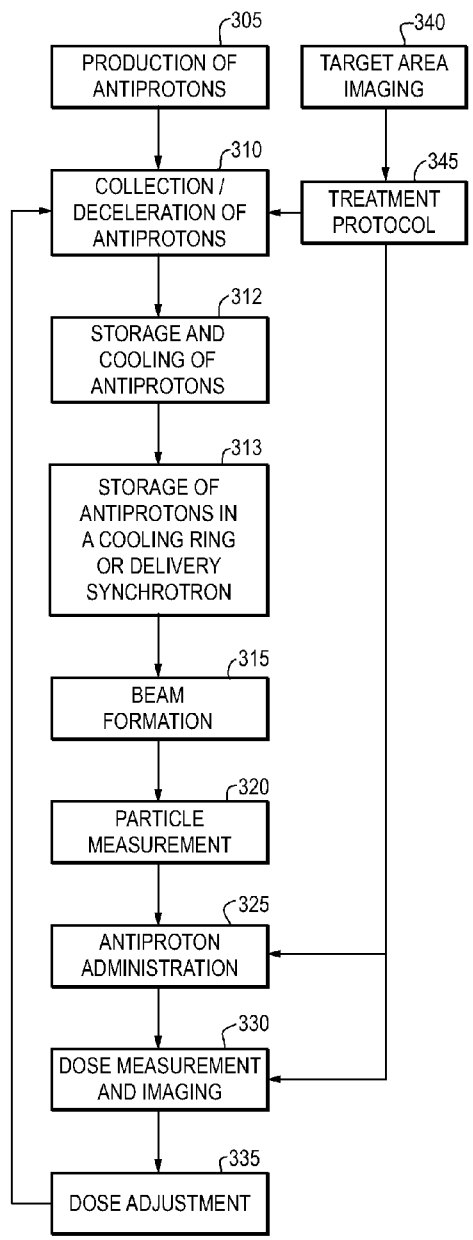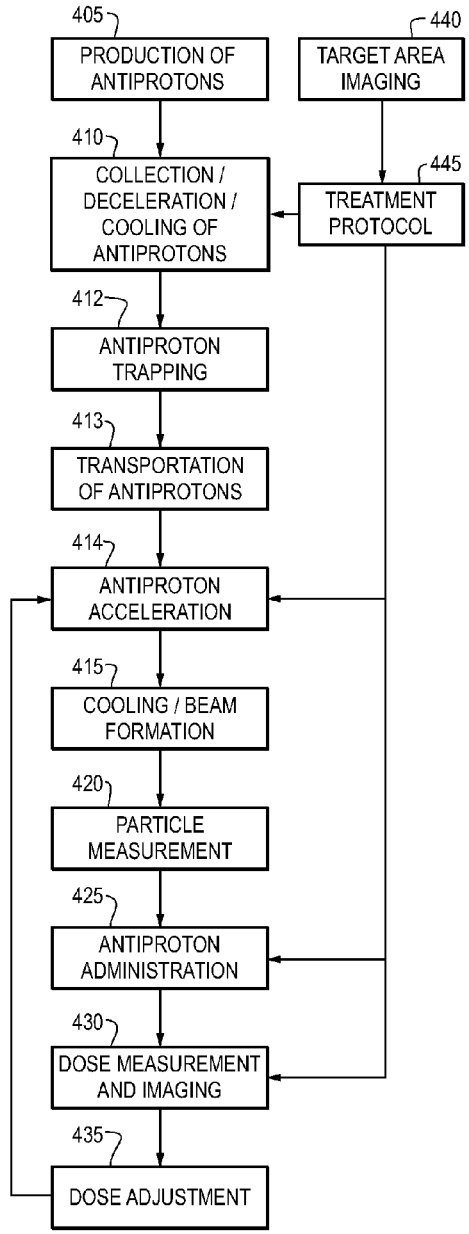

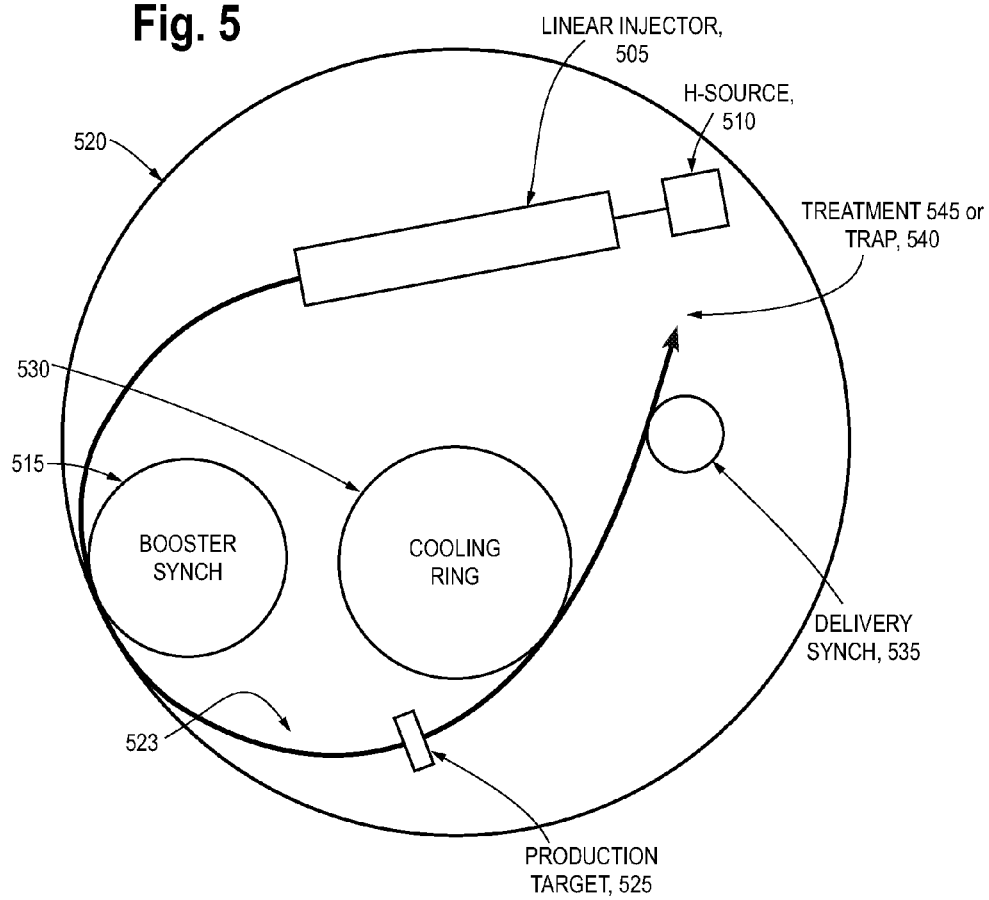
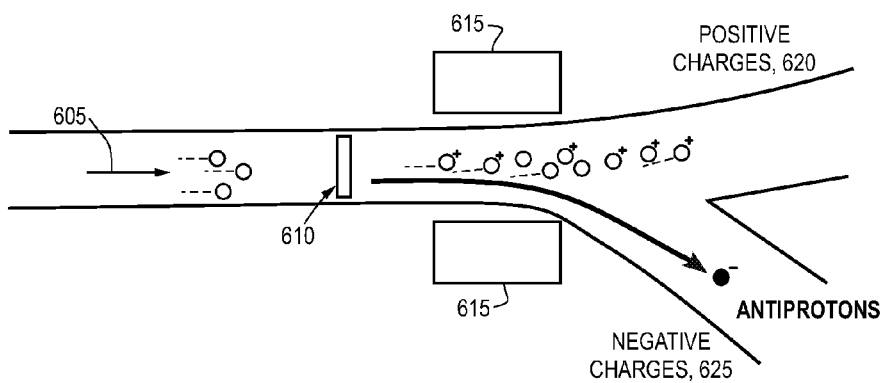

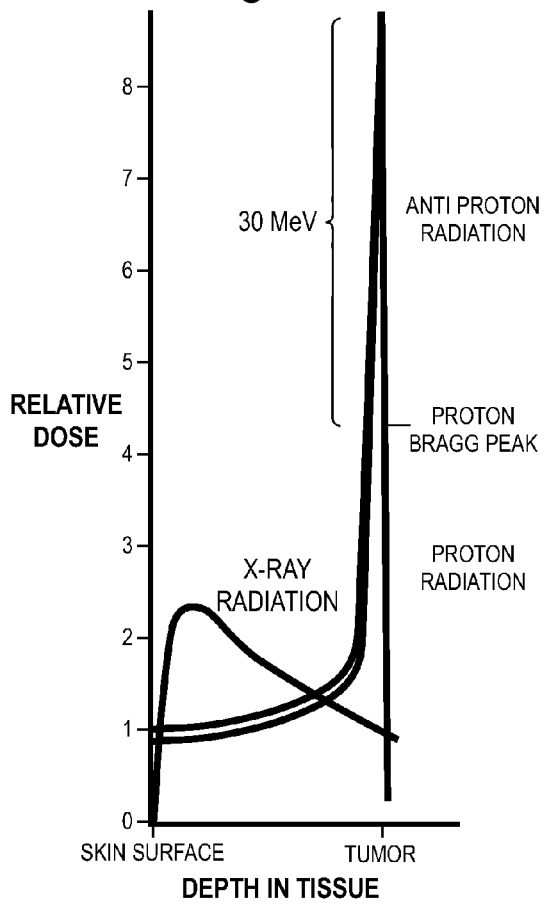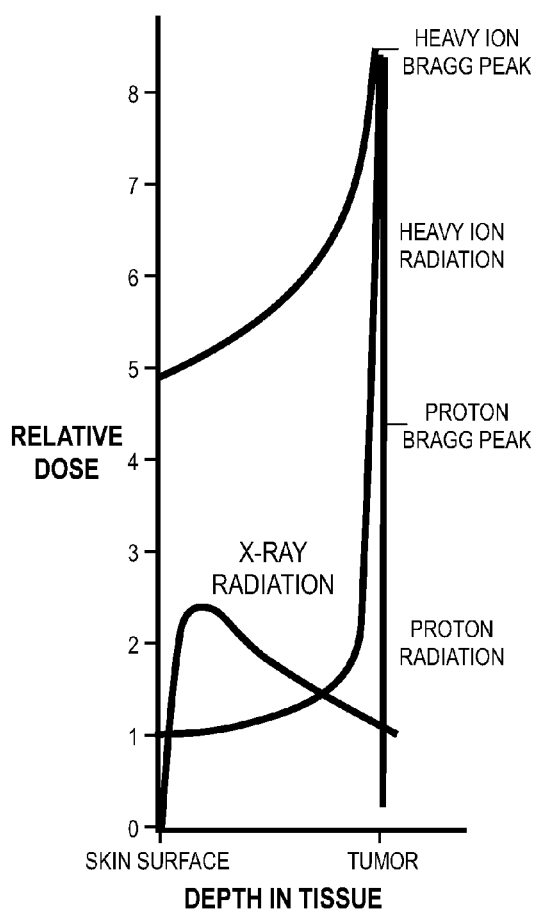

PROTON MULTIPLE SCATTERING AFTER HAVING TRAVERSED 15 cm $H_2O$ IS SHOWN.

PROTON MULTIPLE SCATTERING AFTER HAVING TRAVERSED 15 cm $H_2O$ IS SHOWN.

THE SHOWER RADIAL ENERGY DEPOSITION ORTHOGONAL
TO THE SHOWER AXIS IN TUNGSTEN IS SHOWN

THE SHOWER RADIAL ENERGY DEPOSITION ORTHOGONAL
TO THE SHOWER AXIS IN $PbWO_4$ IS SHOWN

THE OPENING ANGLE IN DEGREES AS A FUNCTION OF NEUTRAL PION MOMENTA AND THE RATIO OF GAMMA-RAY ENERGIES ARE SHOWN

THE LABORATORY-OPENING ANGLES IN RADIANS FOR THE DECAY GAMMAS FROM THE NEUTRAL PION AS A FUNCTION OF PION MOMENTUM AND THE RATIO OF THE ENERGIES OF THE DECAY GAMMAS ARE SHOWN

ANTIPROTON PRODUCTION AND DELIVERY FOR IMAGING AND TERMINATION OF UNDESIRABLE CELLS

I. CONTINUITY STATEMENT

The present patent application is a continuation-in-part of, and incorporates by reference from, Ser. No. 10/479,272, filed on Dec. 1, 2003, now abandoned which is a 371 of PCT/US02/27796, filed on Aug. 29, 2002, which claims benefit from and incorporates by reference Ser. Nos. 60/316,711 filed on Aug. 30, 2001; 60/370,605 filed on Apr. 5, 2002; Ser. No. 60/382,042 filed on May 20, 2002; and Ser. No. 60/388,428 filed on May 29, 2002. All of the above are incorporated by reference.

II. FIELD OF THE INVENTION

The invention relates to the use of radiation to treat medical conditions and, more specifically, to devices, procedures, and systems that controllably deliver antiprotons into a patient for the targeted termination of undesirable cells, such as cancerous cells, within the patient.

III. BACKGROUND OF THE INVENTION

Numerous medical conditions are caused by the existence and/or proliferation of unwanted or undesirable cells within a patient. Such conditions include cardiovascular ailments, such as a trial fibrillation and in-stent restenosis of coronary arteries, arteriovenous vascular malformations (AVMs), cardiac arrhythmias, Parkinson's disease, orthopedic ailments, such as post-op ossification, degenerative and inflammatory arthritis and bone spurs, wet macular degeneration, endocrine disorders, such as insulinomas and pituitary adenomas, herniated or inflamed discs, ovary-related conditions, Graves opthalmoplegia, dermatological ailments, such as furunclosis, telangiectasia, Kaposi's sarcoma, genito-urinary conditions, and cancer.

More specifically, cancer is caused by the altered regulation of cell proliferation, resulting in the abnormal and deadly formation of cancer cells and spread of tumors. Cells are the basic building blocks and fundamental functioning units of animals, such as human beings. Each cell is composed of a nucleus, which contains chromosomes, surrounded by cytoplasm contained within a cell membrane. Most cells divide by a process called mitosis. While normal cells have functioning restraints that limit the timing and extent of cell division, cancerous cells do not have such functioning restraints and keep dividing to an extent beyond that which is necessary for proper cell repair or replacement. This cell proliferation eventually produces a detectable lump or mass herein referred to as a tumor. If not successfully treated, it can kill the animal host.

Cancer that initiates in a single cell, and causes a tumor localized in a specific region, can spread to other parts of the body by direct extension or through the blood stream or lymphatic vessels, which drain the tumor-bearing areas of the body and converge into regional sites containing nests of lymph nodes. The ability of cancer cells to invade into adjacent tissue and spread to distant sites (metastasize) is dependent upon having access to a blood supply. As such, tumors larger than 2 mm have a network of blood vessels growing into them, which can be highly fragile and susceptible to breakage.

Several general categories of cancer exist. Carcinomas are cancers arising from epithelial (squamous cell carcinoma) or secretory surfaces (adenocarcinomas); sarcomas are cancers arising within supporting structures such as bone, muscle, cartilage, fat or fibrous tissue; hematological malignancies are cancers arising from blood cell elements such as leukemia lymphoma and myeloma. Other cancers include brain cancers, nerve cancers, melanomas, and germ cell cancers (testicular and ovarian cancers). Carcinomas are the most common types of cancers and include lung, breast, prostate, gastrointestinal, skin, cervix, oral, kidney and bladder cancer. The most frequently diagnosed cancer in men is prostate cancer; in women it is breast cancer. The lifetime risk of a person developing cancer is about 2 in 5 with the risk of death from cancer being about 1 in 5.

Diagnosing cancer often involves the detection of an unusual mass within the body, usually through some imaging process such as X-ray, Magnetic Resonance Imaging (MRI), or Computed Tomography (CT) scanning, followed by the surgical removal of a specimen of that mass (biopsy) and examination by a pathologist who examines the specimen to determine if it is cancer and, if so, the type of cancer. Positron Emission Tomography (PET) can be used to non-invasively detect abnormally high glucose metabolic activity in tissue areas and thereby assist in the detection of some cancers. The cancer is then assigned a stage that refers to the extent of the cancer. Each cancer has a staging protocol designated by organ. Conventionally, Stage I indicates the existence of a detectable tumor under a specified size, depending on cancer type. Stage II indicates that the cancer has spread into adjacent tissue or lymph nodes. Stage III indicates that the cancer has spread beyond its own region or has grown to a minimum size qualifying it for Stage III status, and Stage IV indicates that the cancer involves another organ(s) at a distant site. Stages are typically assigned by physical examination, radiographic imaging, clinical laboratory data, or sometimes by exploratory surgery.

Once diagnosed and identified in terms of characteristics, location, and stage, the cancer is treated using one, or a combination of several, methods, including surgery, chemotherapy, and radiation. Other less commonly used treatment approaches do exist, including immunotherapy. The cancer is treated with one or several basic goals in mind: cure, prevention of spread, prolongation of survival, and/or palliation (symptom relief).

Surgery is currently a preferred treatment approach where the cancer is localized, in an early stage, and present in only one place. Preferably, the cancer is within a substantial margin of normal tissue and can be excised without unacceptable morbidity or incurring the risk of death. Moreover, for surgery to be successful, the cancer should have little potential to spread to other parts of the body. Surgery needs to be followed up by diagnostic imaging to determine if the cancer has been removed and, in many cases, subsequent adjuvant radiation and/or chemotherapy is administered.

Chemotherapy, usually employing medicines that are toxic to cancer cells, is given by injection into the blood stream or by pill. With certain limitations, the chemotherapeutic agents travel to all parts of the body and can treat cancer in any location by interfering with cell division. Although affecting cancer cells to a greater extent, chemotherapeutic agents do interfere with normal cell division as well, causing severe side effects and adverse health consequences to patients, such as kidney failure, severe diarrheas, or respiratory problems. Certain agents are highly toxic to the heart, reproductive organs, and/or nerves. Almost all are toxic to the bone marrow, which is responsible for the production of the white and the red blood cells and platelets. Because white blood cells such as granulocytes, monocytes and lymphocytes, are primarily responsible for fighting infections and platelets are essential for clotting, chemotherapeutic agents often cause patients to be highly susceptible to infections and spontaneous bleeding. Other side effects include nausea and ulcerations. The course of chemotherapy requires a number of dosage cycles to attack cancer cells, permit healthy cells to recover, and then again attack the target cancer cells. Depending on the patient's response, a decision is made to either stop treatment or continue with some sort of maintenance dosage.

Radiation therapy is the exposing of cancerous cells to ionizing radiation with the objective of terminating those cells over one or several division cycles. Conventionally, radiation is delivered by sending an energy beam, typically x-rays, through a pathway containing healthy tissue and into the target cancerous region. Because energy is being driven through healthy tissue, medical practitioners must determine the best way to deliver sufficient energy to kill a plurality of cancerous cells without generating unacceptable levels of collateral damage to adjacent normal tissue. Several factors should be taken into account, including, for example: 1) the energy deposition profile, which determines what amount of energy a particular radiation beam, having a particular energy level, will deliver to the pathway relative to the target cancer cells, 2) the amount of energy needed to terminate cancerous cells, which determines the threshold level of energy that needs to be delivered to the target site and, consequently, what amount of collateral damage may have to be tolerated in order to do so, and 3) the size, shape, and location of the tumor, which is used to calculate the requisite radiation dosage and determine the appropriate configurations by which radiation beams can be delivered to the target site.

Conventional radiation therapies are frequently unable to deliver sufficiently high levels of radiation to a target region without generating unacceptably high levels of collateral damage. The most common radiation therapy, x-ray (or photon), has a linear energy transfer (LET) profile that varies with depth. The LET of photon radiation increases initially and then decreases with depth, often depositing more energy in intervening tissue than in the target tumor site for deeply buried targets. Photons also continue traveling through the body, once they pass the target region, further depositing energy in healthy tissue. Photons are therefore unable to precisely target a tumor region without endangering surrounding normal tissues.

As such, x-ray radiation treatment sequentially delivers small doses of radiation (fractions) capable of terminating cancerous cells without inflicting too much damage on normal cells. Dividing cells are more susceptible to radiation damage; non-dividing (i.e. resting cells) are less susceptible. X-ray radiation is very often delivered using multiple fields which are required to avoid repeatedly exposing a single healthy tissue pathway to lethal radiation. For example, a typical treatment regimen may require 20-25 exposures in which 200 RADS (Radiation Adsorbed Dose) are delivered per day, 5 days per week for 5 weeks, resulting in a total dose of 5,000 RADS, or 50 Grays, where several of those exposures occur through different pathways having the same target region, an isocenter, in common. Frequent radiation treatments (fractionation of dose) need to occur over a large portion of the replication cycle of a particular cancer, explaining the basis for why a series of treatments over several weeks is required to treat cancer with photon radiation therapy. It should be noted that, even with treatment fractionation and using multiple dose delivery pathways, the collateral damage causes substantial adverse health consequences, from nausea and pain to the permanent disruption of mucosal linings surfaces and adjacent supporting structures.

Proton therapy is another form of radiation therapy currently being used to treat cancer. Relative to other conventional approaches, protons have improved physical properties for radiation therapy because, as a radiation source, they are amenable to control, and thus the radiation oncologist can more precisely shape dose distribution inside a patient's body. Therefore, the dose delivered by a proton beam may be better localized in space relative to conventional radiation therapies, both in the lateral direction and in depth, causing more destruction at a target site with correspondingly less collateral damage.

As shown in FIG. 1, where the target tumor site is at a depth of 25 cm, a mono-energetic proton beam 110 deposits the same energy dosage as a beam of photon energy 105 at the target point. However, the collateral damage, represented by the difference 115, 120 in the areas under the curves between the energy dosages of the two respective beams 110, 105 (measured in areas outside the target region 125), is far greater for the photon beam 105. As a result, the proton beam 110 delivers the same termination power at the tumor site with correspondingly less collateral damage.

A substantial amount of investment has been made in researching proton therapies and building and deploying a proton therapy infrastructure, including proton accelerators, proton delivery devices, such as proton gantries, and specialized medical facilities. Despite this substantial investment, proton therapy still has several significant disadvantages. Most significantly, while the energy deposition profile in proton radiation represents an improvement over conventional approaches, it still does not deliver sufficient amount of termination power at a tumor site relative to the collateral damage it causes.

Another cancer therapy, heavy ion therapy, uses a heavy ion, namely an atom (e.g., a carbon atom) that has been stripped of its electrons, to deliver cancer cell terminating energy to a target region. Like proton beam therapy, heavy ion therapy has the ability to deposit energy directly into the cancerous tumor in three dimensions, hence the dose delivered by the heavy ion beam may also be better localized in space relative to conventional radiation therapies both in lateral direction and in depth. Heavy ions deposit more energy into a tumor than do protons and hence have more cancer cell killing capability than do protons. Heavy ions do have the capability of killing resting cells, but while the killing power deposited on the tumor for ion therapy is dramatically greater, the collateral damage to healthy intervening tissue (that issue between the skin surface and the tumor) is likewise greater—even greater collateral damage than for conventional radiation. In fact, collateral damage inflicted by heavy ion therapy can be even greater than the direct damage to the tumor with proton therapy. Additionally, in certain heavy ion therapy applications, treatment imaging is enabled by the fragmentation of the heavy ion, such as $^{12}C$, as it approaches a patient in-beam and as it strikes cells while traveling through a patient. The heavy ion fragments into isotopes that may be imaged through conventional PET detection, that being $^{11}C$ in the case of $^{12}C$ heavy ion therapy. This imaging process is not, however, real-time in that imaging is delayed until the radioisotope decays and is substantially complicated by the migration of the isotope within the tumor.

IV. SUMMARY OF THE INVENTION

It will be highly beneficial to treat cancer by delivering radiation to a tumor region that is sufficient enough to kill both dividing and non-dividing (resting) cancerous cells while not terminating an unacceptably high number of healthy cells in the radiation delivery pathway, thereby minimizing the number of treatments required and substantially eliminating fractionation requirements. Additionally, neither proton therapy nor heavy ion therapy permits any real-time imaging of the treatment as it occurs. It will be very beneficial to deploy a radiation source that can enable the real-time imaging of the treatment, where the images are generated at the point of the radiation delivery as by-products of the cancer cell termination process.

Preferred methods and systems disclosed herein are directed toward the use of antiprotons for the termination of cells. The cells thus terminated are preferably unwanted or undesirable due to any of a great number of reasons, including, but not limited to, being malformed or simply being present in an unwanted or undesirable location. The methods and systems, in preferred embodiments, are directed toward treatment of conditions caused by the existence and/or proliferation of undesirable cells. Such conditions include cardiovascular ailments, such as atrial fibrillation and in-stent restenosis of coronary arteries, arteriovenous vascular malformations (AVMs), cardiac arrhythmias, Parkinson's disease, orthopedic ailments, such as post-op ossification, degenerative and inflammatory arthritis and bone spurs, wet macular degeneration, endocrine disorders, such as insulinomas and pituitary adenomas, herniated or inflamed discs, ovary-related conditions, Graves opthalmoplegia, dermatological ailments, such as furunclosis, telangiectasia, Kaposi's sarcoma, genito-urinary conditions, and cancer.

In one embodiment, there is provided a method for treating a patient having a plurality of undesirable target cells, such as cancer cells, comprising receiving a plurality of antiprotons in a trapped state, inserting the antiprotons into an accelerator, accelerating the antiprotons to a predetermined, therapeutic energy level, forming a beam of antiprotons, and exposing at least a portion of the plurality of undesirable target cells to the beam, thereby causing the termination of one or more of said cells.

In another embodiment, there is provided a method for treating a patient having a plurality of undesirable target cells, such as cancer cells, in an area comprising imaging the area, determining a dose of antiproton radiation to be delivered to the area wherein the determination is a function of the destructive effect of antiprotons annihilating in the area and the destructive effect of alpha particles released from the annihilations, and delivering the determined dose of antiprotons to the area.

In another embodiment, there is provided a system for treating a patient having a plurality of undesirable target cells, such as cancer cells, comprising an accelerator having a receptor port for receiving a plurality of antiprotons wherein the accelerator accelerates the antiprotons from a trapped state to a predetermined, therapeutic energy level, an antiproton delivery device for directing the antiprotons as a beam at the plurality of undesirable target cells in a patient; and a patient station for supporting the patient in a position allowing the plurality of undesirable target cells be radiated by the beam of antiprotons.

In another embodiment, there is provided a system for treating a patient having a plurality of undesirable cells, such as cancer cells, comprising an accelerator for accelerating a plurality of antiprotons to a predetermined, therapeutic energy level, an antiproton delivery device for directing the antiprotons as a beam at the plurality of undesirable target cells in a patient, a beam monitoring system, structurally integrated with the antiproton delivery device, for monitoring the beam; and a patient station for supporting the patient in a position allowing the plurality of undesirable target cells be radiated by the beam of antiprotons. In a preferred embodiment, the system further comprises a processor operative to process an instruction set that determines a dose of antiproton radiation to be delivered to said area wherein the determination is a function of the destructive affect of antiprotons annihilating in said area and the destructive affect of alpha particles released from said annihilations; and an output device in data communication with the processor.

In another embodiment, there is provided a method for activating a patient's immune response to counter cancerous cell growth comprising receiving a plurality of antiprotons into an accelerator, accelerating the antiprotons to a predetermined, therapeutic energy level, forming a beam of antiprotons, and exposing a tumor in the patient to the beam, wherein the activation is achieved by minimizing injury to tumor-adjacent antigen serving macrophage dendritic cells and minimizing injury to lymphokine activated killer T-cells in the tumor microenvironment.

In another embodiment, there is provided a system for activating a patient's immune response to counter cancerous cell growth comprising an accelerator for accelerating a plurality of antiprotons to a predetermined, therapeutic energy level, an antiproton delivery device for directing the antiprotons as a beam at a tumor in a patient; and a patient station for supporting the patient in a position to have said tumor be radiated by the beam, wherein the activation is achieved by minimizing injury to tumor-adjacent antigen serving macrophage dendritic cells and minimizing injury to lymphokine activated killer T-cells in the tumor microenvironment.

Certain other embodiments also include novel embodiments of antiproton delivery devices, including a retrofitted proton gantry and a fixed beam antiproton delivery system, and an antiproton medical facility integrating existing cancer diagnostic stations with antiproton therapy, as described herein. Because of the unique nature of antiprotons and their annihilation characteristics, some preferred antiproton delivery device embodiments further incorporate detector arrays, capable of detecting characteristic emissions in the course of treatment.

V. BRIEF DESCRIPTION OF THE DRAWINGS

These and other features and advantages of the described embodiments of the invention will be appreciated, as they become better understood by reference to the following Detailed Description when considered in connection with the accompanying drawings, wherein:

FIG. 1 is a graph of energy deposition as compared to depth for conventional radiation therapies;

FIG. 1A is a diagram of a typical antiproton annihilation event;

FIG. 2 is a graph of energy deposition as compared to depth for conventional radiation therapies and antiproton therapy;

FIG. 3 is a schematic flowchart representation of one preferred embodiment;

FIG. 4 is a schematic flowchart representation of another preferred embodiment;

FIG. 5 is a diagram of an antiproton production facility;

FIG. 6 is a diagrammatic representation of antiproton generation;

FIG. 7 is a schematic representation of one embodiment of an antiproton delivery device;

FIG. 8 is a schematic representation of another embodiment of an antiproton gantry;

FIG. 9 is a schematic representation of another embodiment of an antiproton delivery device;

FIG. 10A is a schematic representation of an embodiment of an antiproton delivery device combined with a detector array;

FIG. 10B is a schematic representation of an embodiment of an antiproton delivery device combined with a detector array;

FIG. 10C is a schematic representation of a detector array, taken from a beam pipe perspective, using PbWO.sub.4 as a calorimeter element and applied to brain imaging;

FIG. 10D is a side view schematic representation of a detector array using PbWO.sub.4 as a calorimeter element and applied to brain imaging;

FIG. 10E is a schematic representation of a detector array, taken from a beam pipe perspective, using PbWO.sub.4 as a calorimeter element and applied to torso imaging;

FIG. 10F is a side view schematic representation of a detector array using PbWO.sub.4 as a calorimeter element and applied to torso imaging;

FIG. 10G is a schematic representation of a detector array, taken from a beam pipe perspective, using CsI(TI) as a calorimeter element and applied to brain imaging;

FIG. 10H is a side view schematic representation of a detector array using CsI(TI) as a calorimeter element and applied to brain imaging;

FIG. 10I is a schematic representation of a detector array, taken from a beam pipe perspective, using CsI(TI) as a calorimeter element and applied to torso imaging;

FIG. 10J is a side view schematic representation of a detector array using CsI(TI) as a calorimeter element and applied to torso imaging;

FIG. 10K is a schematic representation of a detector array, taken from a beam pipe perspective, using Ir as a calorimeter element and applied to brain imaging;

FIG. 10L is a side view schematic representation of a detector array using Ir as a calorimeter element and applied to brain imaging;

FIG. 10M is a schematic representation of a detector array, taken from a beam pipe perspective, using Ir as a calorimeter element and applied to torso imaging;

FIG. 10N is a side view schematic representation of a detector array using Ir as a calorimeter element and applied to torso imaging;

FIG. 10O is a schematic representation of a detector array, taken from a beam pipe perspective, using W as a calorimeter element and applied to brain imaging;

FIG. 10P is a side view schematic representation of a detector array using W as a calorimeter element and applied to brain imaging;

FIG. 10Q is a schematic representation of a detector array, taken from a beam pipe perspective, using W as a calorimeter element and applied to torso imaging;

FIG. 10R is a side view schematic representation of a detector array using W as a calorimeter element and applied to torso imaging;

FIG. 11 is a layout of an exemplary antiproton radiation medical facility;

FIG. 11a is a schematic representation of a beam line integrated into a medical facility;

FIG. 12 is a schematic flowchart of an existing therapy station integrated with an antiproton treatment protocol station; and FIG. 13 is an exemplary output graphic combining antiproton dosage ranges with tumor location.

FIG. 14 is a dose vs. depth curve for antiproton radiation, x-ray radiation, and proton radiation.

FIG. 15 is a dose vs. depth curve for x-ray radiation, proton radiation, and heavy ion radiation.

FIG. 16 is an image of a cross-section of tissue showing deposition of energy in tissue throughout its depth from incident x-ray radiation.

FIG. 17 is an image of a cross-section of tissue showing deposition of energy in tissue throughout its depth from incident proton radiation.

FIG. 18 is a chart showing ionization tracks of protons and heavy ions in water.

FIG. 19 is a chart showing proton multiple scattering after 15 cm H2O vs. Momenta.

FIG. 20 is a chart showing $\pi$ multiple scattering after 15 cm H2O vs. Momenta.

FIG. 21 is a chart showing shower radial energy desposition orthogonal to shower axis in tungsten.

FIG. 22 is a chart showing shower radial energy disposition orthogonal to shower axis in $PbWO_4$.

FIG. 23 is a chart showing the lab opening angle in degrees as a function of neutral pion momenta and the ratio of gamma-ray energies.

FIG. 24 is a chart of the lab opening angle in radians for the decay gammas from the neutral pion as a function of pion momentum and the ratio of the energies of the decay gammas.

VI. DETAILED DESCRIPTION OF THE PREFERRED EMBODIMENTS

Preferred embodiments disclosed herein are related toward preferred methods and systems for the use of antiprotons for the termination of cells, including, but not limited to use for the treatment of medical conditions caused by existing or proliferating unwanted or undesirable cells, such as cancer, and the accompanying devices, systems, and processes to conduct such treatments. Such conditions include cardiovascular ailments, such as atial fibrillation and in-stent restenosis of coronary arteries, arteriovenous vascular malformations (AVMs), cardiac arrhythmias, Parkinson's disease, orthopedic ailments, such as post-op ossification, degenerative and inflammatory arthritis and bone spurs, wet macular degeneration, endocrine disorders, such as insulinomas and pituitary adenomas, herniated or inflamed discs, ovary-related conditions, Graves opthalmoplegia, dermatological ailments, such as furunclosis, telangiectasia, Kaposi's sarcoma, genito-urinary conditions, and cancer. While the detailed description provided herein primarily discusses the application of the preferred methods and systems to the termination of cancerous cells, one of ordinary skill in the art will appreciate that the methods and systems can be applied to the termination of any type of unwanted or undesirable cell. The specific use of cancer in the present description should not be interpreted to limit the application of the methods and systems to the treatment of cancer. Furthermore, unwanted and undesirable shall be used interchangeably to describe the cells which are the preferred targets of the antiprotons as described herein.

Antiprotons have been identified as a preferential radiation source for the treatment of cancer for several reasons. First, as discussed herein, antiproton production and distribution are now technically and economically feasible, making antiprotons a viable radiation source for medical treatments. Second, as antiprotons travel through a substance, such as human tissue, they transfer energy in a manner similar to other charged particles. As with protons, antiprotons lose kinetic energy as they pass through a substance, causing collateral damage to the healthy tissue pathway. The theory of energy loss for a charged particle can be described by the following equation, where the stopping power (dE/dx) in MeV is approximated using p (g/cm.sup.3) as the density of the medium, .beta. is the velocity (v/c) of the moving particle, f(.beta.)=In(2 mc.sup.2.beta..sup.2/(1-.beta..sup.2))=.beta..sup.2, m is the mass of the electron (0.51 MeV/c2), and $Z_i$, $A_i$, $C_i$ and $I_i$ (MeV) are the atomic number, weight, concentration, and excitation potential of the i.sup.th element, respectively.

$$-\frac{1}{\rho}\frac{dE}{dX} = \frac{0.30708}{\beta^2} \cdot \sum \frac{Z_i \cdot C_i}{A_i}\{f(\beta) - \ln I_i\}$$

As the velocity of a charged particle decreases, the stopping power increases rapidly because of the inverse proportional dependence on particle velocity (.beta..sup.2). The result is a very large energy deposition toward the end point which, in the case of cancer therapy, is in the tumor itself. The large final energy deposition causes a sharp Bragg Peak, as shown in FIG. 1 for proton therapy. Unlike protons, however, antiprotons undergo a highly energetic annihilation event, releasing a plurality of charged and neutral particles and causing a much greater amount of damage in the target region, once they slow down in the target area and become captured in a nucleus or as they pass through the target area. Referring to FIG. 1A, when an antiproton 105A comes to rest with a nucleus, it generates an annihilation event 110A, in which several by-products are generated, including gamma radiation 115A, mesons (both charged and neutral pions) 120A, and heavy charged particles 125A. The heavy charged particles are highly destructive to nuclei adjacent to the annihilation site and, therefore, propagate the damage incurred from the initial antiproton annihilation to adjacent cells, thereby terminating more cells in the course of a single antiproton exposure. This unique annihilation event allows for the targeted, localized delivery of larger amounts of cell-terminating radiation with substantially similar amounts of collateral damage, thereby permitting cancer treatment regimens that do not require fractionated treatment protocols. The nature of this annihilation event is an important element in the proper determination of dosage and to the real-time imaging process, as later discussed herein.

Referring to FIG. 2, the relative doses (arbitrary units) of various radiation sources are shown in relation to depth of energy deposition in tissue. A target tumor site 203 is identified at a particular depth, such as 11-12 cm. A mono-energetic proton beam 210 delivers a relative biological dose of 1, as compared to a beam of photon energy 205, which delivers a relative biological dose of approximately 0.65. An antiproton beam 220 substantially overlays with the proton beam 210, but has a greater relative dose at greater than 1.2, the difference being represented by 225. Despite the greater relative dose, the antiproton beam 220 has substantially similar amounts of collateral damage compared to the proton beam 210 and far less collateral damage compared to the photon beam 205, the collateral damage being caused by the deposition of energy over the region 230 between the skin surface and tumor site. As a result, the antiproton beam 220 delivers the greater termination power at the tumor site 203 with correspondingly less collateral damage (the difference in collateral damage determined by taking the difference between the integrated areas under beam curve 210 and beam curve 220 calculated over region 230). From a different perspective, for the same collateral damage, the antiproton beam can deliver far greater termination power at the tumor site relative to proton and photon radiation sources.

One preferred embodiment, as diagrammed in FIG. 3, comprises the production of antiprotons 305, the collection and then deceleration of antiprotons to a desired energy level 310, the storage and cooling of antiprotons 312, the storage of antiprotons in a cooling ring or delivery synchrotron 313, the formation of antiprotons into an administrable beam 315, the measurement of antiprotons to determine the actual number being delivered 320, the delivery of that measured beam via an antproton delivery and imaging device to a prepared patent 325, optionally though preferably the dose measurement and imaging of the resultant radiation event and comparison of that image to previously recorded images of the target area 330, and, optionally, though preferably, the adjustment of dosage characteristics to insure the impacted area, as imaged, aligns with the desired target area 335. Prior to the delivery step, a patient had been prepared, optionally, though preferably, by imaging the target area 340 using imaging technologies, to confirm the size, location, and configurational characteristics of the target tumor, and determining an appropriate treatment regimen in light of the tumor characteristics 345. A patient is then securely positioned relative to the antiproton delivery and image device. The treatment regimen data informs the extent of deceleration 310 (i.e. the predetermined delivery energy of the antprotons useful for treatment), antiproton delivery methodology 325, and the dose measurement and imaging of the resultant radiation event and comparison of that image to previously recorded images of the target area 330.

Another embodiment, as diagrammed in FIG. 4, comprises the production of antiprotons 405, the collection, deceleration and cooling of antiprotons 410, the trapping of cooled and slowed antiprotons into a trap device 412, the transport of the trap device to a medical facility 413, the reception and acceleration (i.e. to a suitable energy) of antiprotons at the medical facility 414, the cooling and formation of antiprotons into an administrable beam 415, the measurement of antiprotons to determine the actual number being delivered 420, the delivery of that measured beam via an antiproton delivery and imaging device to a prepared patient 425, optionally though preferably the dose measurement and imaging of the resultant radiation event and comparison of that image to previously recorded images of the target area 430, and, optionally though preferably, the adjustment of dosage characteristics to insure the impacted area, as imaged, aligns with the desired target area 435. Prior to the delivery step, a patient had been prepared, optionally though preferably, by imaging the target area 440 using imaging technologies, to confirm the size, location, and configurational characteristics of the target tumor, and determining an appropriate treatment regimen in light of the tumor characteristics 445. A patient is then securely positioned relative to the antiproton delivery and image device. The treatment regimen data informs the extent of antiproton acceleration (i.e. the delivery energy of the antiprotons needed for treatment) 414, antiproton delivery methodology 425, and the dose measurement and imaging of the resultant radiation event and comparison of that image to previously recorded images of the target area 430. These two preferred embodiments, along with other embodiments, shall be discussed in greater detail in each of the subsequent sections.

Antiproton Production

Antiprotons for use in the preferred methods and systems disclosed herein can be generated by any method. The antiproton generation process is described herein using a circular accelerator, such as the one found at Fermi National Laboratory in Batavia, Ill. It should be noted, however, that the Fermi accelerator has been designed to generate antiprotons having far greater energies than that which are generally preferred for use in connection with the preferred methods and systems disclosed herein. Although such antiprotons may be effectively altered to suit the methods, as discussed below. Different accelerators, such as a circular accelerator that accelerates particles to energies lower than those achieved by Fermi National Accelerator Laboratory, can also be effectively used in the context of the methods and systems described herein.

In a preferred embodiment, antiproton production comprises a six-stage process, culminating in the deceleration of antiprotons for medical application or storage and trapping, as discussed in the subsequent sections. Referring now to FIG. 5, a device [not shown], an exemplary embodiment of which is a Cockroft-Walton, is used to add electrons to hydrogen atoms delivered from a source 510, resulting negative ions consisting of two electrons and one proton. The device applies a positive voltage to the negative ions, thereby accelerating them. In one embodiment, the negative ions are accelerated to an energy of approximately 750 keV. The negative ions are transferred from the Cockroft-Walton device and enter into a linear accelerator (or a Linear Injector) 505, referred to as a Linac, which comprises a plurality of tanks filled with tubes spaced varying distances apart. An electric field is applied to the tubes, repeatedly reversing in direction, causing the negative ions to alternately hide in tubes when the electric field, as applied, will slow them down, and emerge into gaps between the tubes when the field is of a direction that accelerates them. The Linac 505 further increases the energy of the ions to approximately 400 MeV. The negative ions are passed through a carbon foil, thereby removing the electrons and leaving protons, which are then passed into a booster synchrotron 515. The booster synchrotron 515 is a circular accelerator, a rapid cycling synchrotron that forces the positively charged particles to travel in a circular path through the application of magnetic fields. Through each revolution, the protons experience the repeated application of accelerating electric fields and therefore increase in energy. In one embodiment, the booster 515 raises the energy level of protons to about 8 GeV, cycles approximately 12 times in rapid succession, and introduces about 12 proton packets (pulses) into the main accelerator ring 520, which is a synchrotron that further accelerates the protons to about 150 GeV. In the embodiment, the accelerator 520 is approximately four miles in circumference with a tunnel ten feet in diameter and housing approximately 1,000 copper-coiled magnets to bend and focus the protons. In another embodiment, the booster 515 introduces proton packets into a 14 GeV main accelerator ring 520.

In this embodiment, antiprotons are produced by extracting bunches of approximately 120 GeV protons from this synchrotron ring 520, transporting them via a beamline 523 to a production target 525, and focusing them on the target 525. In other related embodiments, the protons may be at other energies as would be recognized by those skilled in the art. The proton collisions with the target 525 produce a number of particles, including antiprotons. The produced antiprotons are selected, as shown in FIG. 6, and transported to a ring 530 where they are debunched and then cooled, preferably by a process referred to as stochastic cooling. In this context, beam cooling is the technique where both the physical size and energy spread of a particle beam circulating in a cooling/ storage ring are reduced with little accompanying beam loss, as further discussed below. Subsequently, the antiprotons are transferred to another ring 535 for deceleration or acceleration to appropriate energies for delivery to a specialized antiproton trap 540, to a treatment system 545 or for accumulation and/or storage.

Antprotons are created by the interaction of high-energy protons with nuclei in the target area. Referring now to FIG. 6, a schematic diagram of antiproton production is provided. Protons 605 having an energy level are focused on, and impact, a target 610. The target is preferably comprised of a metallic material that is relatively easy to remove heat from, such as copper, nickel, or iridium. In approximately one collision per million, an antiproton-proton pair is formed. In one operation, approximately 10 trillion protons impinge on the target per minute, generating 10 million antiprotons. Using magnets 615, antiprotons are separated from the positively charged protons and directed toward a system and process for cooling the antiproton beam. As previously stated, antiprotons can be created in a number of different ways. In another embodiment, protons are accelerated in a linear accelerator, a booster, and then a synchrotron up to about 27 GeV. The protons are focused onto a target, such as the materials mentioned above, and, in the interaction of the protons with the target nuclei, produce many particle-antiparticle pairs, including proton-antiproton pairs.

One of ordinary skill in the art will appreciate that the present invention is not limited to the above-described antiproton generation methods. For example, other methods and systems for generating negative hydrogen ions, not simply a Cockroft-Walton device may be used. Additionally, while specific energy levels have been described, preferred methods can be effectively performed by generating antiprotons from protons accelerated to any appropriate range, such as approximately 12 GeV/c, 11 GeV/c, 10 GeV/c, 13 GeV/c, among other values. In a preferred embodiment, a circular accelerator with a smaller circumference is used to generate protons and antiprotons at lower energy levels, thereby allowing for a more cost-effective antiproton production method. The process of producing antiprotons results in a plurality of antiprotons moving at high momentum, with varying energies (referred to as energy spreads) and directions (referred to as transverse oscillations). To commercially deploy antiprotons, however, such energy spreads and transverse oscillations are preferably reduced. The term "cooling" refers to the reduction of the beam's transverse dimensions and energy spread.

Electric fields are preferably applied to antiprotons, as they travel through a vacuum pipe ring structure. Within the radio frequency cavities, as antiprotons decelerate, the size of their transverse oscillations increase. If not managed properly, a substantial number of antiprotons can be lost in this process. Among the cooling methods that may be used to avoid excessive antiproton loss are stochastic cooling and electron cooling. Electron cooling uses an electron beam merged with the antiproton beam to act as a heat exchanger and is more effective at low energy. In stochastic cooling, the beam is positionally sampled by a monitor and an error signal generated in a monitor is fed back, via a corrector, to the beam sample that created it. This process eventually centers the sample's characteristics towards an average value, after a large number of passages through the apparatus. In preferred embodiments, generated antiprotons are decelerated to an energy level suitable for the particular medical treatment methodology being employed. More specifically, where a medical facility is located proximate to the antiproton generation location, generated antiprotons are preferably slowed from their generation energies to a medically beneficial energy level, such as between 1 MeV and 300 MeV, preferably around 250 MeV, and delivered directly to a patient, as further discussed below. To do so, a deceleration, cooling, and collection process is performed. Antiprotons are decelerated to a low energy level, for example between 1.5 and 3 GeV/c, or alternatively, they are generated at that energy. In one embodiment, the deceleration process is performed using the aforementioned cooling techniques in a separate, dedicated deceleration ring. In another embodiment, this first deceleration step is unnecessary because a low-energy antiproton production method is used and consequently generates low energy antiprotons, such as in the 1.5-3 GeV/c range. It should be noted that the 1.5-3 GeV/c energy range is not meant to be restrictive of the low energy range.

Once in the 1.5 GeV/c range, antiprotons are collected and further decelerated to a medically beneficial energy level, such as about 250 MeV. In a preferred embodiment, this collection and second deceleration stage is conducted by employing the aforementioned cooling and deceleration techniques in a dedicated cooling and deceleration ring. The antiprotons can be stored either in the cooling ring or in the delivery synchrotron. As discussed below, the antprotons, once a medically beneficial energy level, are introduced via a beam line to a patient, a controlled, adjustable energy level, through a number of alternative antiproton delivery devices. Alternatively, where a medical facility is not proximate to an antiproton production location, preferably antiprotons are produced, stored, and transported to facility sites. Antiprotons are therefore similarly decelerated down to an appropriate level, after which the antiprotons are squeezed out in groups, referred to as bunches, and ejected through the application of a kicker magnet which leads the ejected antiprotons through a separate line into an accumulator, collector, or some other storage device. A person familiar with high-energy physics will understand how to produce, collect, cool, decelerate and extract antiprotons through the application of vacuums pumps, magnets, radio-frequency cavities, high voltage instruments and electronic circuits. Antiprotons circulate inside vacuum pipes in order to avoid contact with matter with which they annihilate. The vacuum should be as high as possible and therefore several vacuum pumps, which extract air, are placed around the pipe. The magnets used include dipoles, which serve to change the direction of antiproton movement and insure they stay within the circular track, and quadrupoles, which are used as lenses or focusing magnets to insure that antiproton beam size is smaller than the vacuum pipe size. Electric fields are used to modify antiproton energy levels and are provided for by radio-frequency cavities that produce high voltages synchronized with the rotation of antiprotons around the ring.

Antiprotons may either be stored in a ring for future use or in traps for distribution to antiproton medical facilities. In one embodiment, antiprotons are stored in traps, such as those disclosed in U.S. Pat. Nos. 6,160,263 and 5,977,554 which are incorporated herein by reference. The trapped antiprotons are inserted into a linear accelerator or synchrotron, accelerated to appropriate energy levels, and then formed into a beam for use in treatment. Operationally, the trap is attached to an inlet port that interfaces with a Linac or RFQ. The electric field used to trap the voltage is decreased while an attracting field is generated in the accelerator, causing the antiprotons to drift into the accelerator structure. Antiprotons therefore drift from the trap at very low energies, on the order of about 10-20 KeV. Once the antiprotons are positioned inside the accelerator, they are accelerated to an appropriate energy level. The delivery synchrotron is preferably designed to be stable at 1 MeV-300 MeV energy levels and will result in antiprotons being delivered at certain minimum energies, which can be accelerated to using a small Linac or an RFQ. An exemplary cyclotron will preferably be designed for the production of an antiproton beam, i.e. 1.5 mA proton current at 590 MeV.

Whether obtaining the antiprotons from a decelerator attached to the main antiproton production source or obtaining antiprotons from a trapped state and accelerating them, a main antiproton beam is generated. The beam is stored and conditioned in a delivery synchrotron. The stored antiprotons can then be adjusted to an appropriate energy level while in the delivery synchrotron. Adjustment of the energy can be readily achieved such as by using the rapid-cycling energy characteristic of the delivery synchrotron or by using a set of carbon or copper degrader blocks, or a combination of the two methods. In a combination mode, the energy of the beam can be adjusted by changing the arrangement of the degrader blocks to provide variable degrader thicknesses to the beam and by tuning the beam line to the appropriate delivery momentum. In a preferred embodiment, no degrader blocks are used to adjust the beam energy, as the degrader processes may produce spurious particle emissions such as undesired neutrons. Spurious particle emission is generally avoided if the delivery synchrotron is adjusted to provide particles of the desired target energy level directly. A calculated number of antiprotons at the correct energy is then split off the stored beam using an electrostatic splitter for delivery to a patient.

For medical applications, the target energy level may vary between about 1 MeV and 300 MeV, preferably about 250 MeV and including 5 MeV, 10 MeV, 15 MeV, 20 MeV, 25 MeV, 30 MeV, 35 MeV, 40 MeV, 45 MeV, 50 MeV, 55 MeV, 60 MeV, 65 MeV, 70 MeV, 75 MeV, 80 MeV, 85 MeV, 90 MeV, 95 MeV, 100 MeV, 105 MeV, 110 MeV, 115 MeV, 120 MeV, 125 MeV, 130 MeV, 135 MeV, 140 MeV, 145 MeV, 150 MeV, 155 MeV, 160 MeV, 165 MeV, 170 MeV, 175 MeV, 180 MeV, 185 MeV, 190 MeV, 195 MeV, 200 MeV, 205 MeV, 210 MeV, 220 MeV, 225 MeV, 230 MeV, 235 MeV, 240 MeV, 245 MeV, 250 MeV, 255 MeV, 260 MeV, 265 MeV, 270 MeV, 275 MeV, 280 MeV, 285 MeV, 290 MeV, 295 MeV, and 300 MeV. The specific energy used at any time depends upon the particle penetration depth for the specific treatment being performed. The particle beam is preferably analyzed in momentum and phase space using beam profile monitors to insure the resultant beam is appropriately shaped and is substantially monochromatic in order to couple the beam into the delivery device. The delivery synchrotron provides substantially monochromatic particles directly by the intrinsic nature of the synchrotron acceleration process. The shape characteristic of the particle beam is adjustable by means of a pair of magnetic quadrupole focusing elements positioned along the delivery beam pipe. In treatments requiring high spatial resolution, the beam will be focused into a small spot size using the magnetic quadrupole focusing elements. Other treatments may utilize a broader, less highly focused beam. A continuous range of beam geometries between broad and sharply focused can be achieved using the magnetic quadrupole focusing elements, without affecting the monochromatic nature of the beam. The beam is then introduced into a beam line, a vacuum pipe, that is directed into the antiproton radiating and imaging device.

Antiproton Radiating and Imaging Device

The beam line is directed through an antiproton radiating and imaging device in order to administer antiproton radiation to a patient. In one embodiment, a gantry is used to deliver antiprotons to a patient, or a proton therapy gantry is retrofitted to accept and deliver antiprotons instead of protons. Referring to FIG. 7, an antiproton gantry is shown. The antiproton gantry comprises a delivery pipe 1005 passing through a shielded support structure 1010 and into a gantry head 1015 through which the antiprotons are directed into a patient 1020. Although not required, the delivery pipe 1005 bends as it extends out from an accelerator [not shown], through the structure 1010, and into the gantry head 1015 through the application of magnets 1030. More specifically, in the illustrated embodiment, the antiproton beam [not shown] enters into the structure 1010 via the vacuum pipe 1005 and is deflected by two 35 degrees bending magnets 1030 that are parallel to the rotation axis of the gantry head 1015. Once in the gantry head 1015, the beam is directed, through the use of a magnet 1030, through a nozzle 1035 having a monitor and range shifter system [not shown], and into the patient 1020. In addition to the plurality of magnets 1030, there are preferably also focusing quadrupole magnets [not shown].

Preferably the support structure 1010 is designed to provide maximum rigidity to the beam line. The weight of the entire gantry generally is dominated by the bending magnets 1030 and appropriate balancing weights should be provided in the structure 1010 to insure the gantry does not fall, tip, or otherwise become unstable. Operationally, the antiproton beam is deposited in the patient as a sequence of sequential, directed applications. Referring to FIG. 8, the number of antiprotons delivered in a single, directed application is measured by the beam monitor system 1140 positioned in the nozzle 1135. In one embodiment, the beam monitoring system comprises two monitoring subsystems providing two independent beam flux measurements. The first subsystem comprises two parallel plane ionization chambers. The first chamber covers the size of the full swept beam. The external high-voltage planes are preferably made of thin Mylar foils, approximately 25 microns, coated with aluminum. The signal plane in the middle of the chamber is generally open to air and operates at about 2 kV. The gap between the signal and high voltage foils is approximately 5 mm on each side of the signal plane, allowing for a fast collection time of less than 100 microseconds. The second chamber is a similar ionization chamber with a larger gap, i.e. 1 cm, and a lower electric field, i.e. 2 kV of applied voltage. The reaction time of the second monitor is slower. The second subsystem comprises of a position sensitive monitor made of kapton foils coated with 4 mm wide aluminum strips. The ionization charge created in the gap of the chamber is collected on the different strips, providing the information on the position and shape of the antiproton beam. In preferred embodiments, This information is monitored continuously during treatment by reading the content of scalers at the end of each spot. Preferably, two strip planes are used, one for the direction perpendicular to the sweeper displacement and the other parallel to it. It should be further noted that other methods and systems can be used to monitor the beam. For example, measuring antiproton delivery rates can be achieved by calculating the difference between how many antiprotons are left in a storage device, cooling ring, or other source after a pulse of antiprotons has been delivered to the synchrotron relative to how many antprotons were present in the source prior to the pulse.

Once the target number of antiprotons has been reached, the beam is switched off using a fast kicker-magnet [not shown] located in the beam line ahead of the gantry head 1115. In one embodiment, the fast kicker magnet is a 20 cm long, laminated C-magnet with a 5 cm pole gap, and the vacuum chamber is an elliptical pipe comprised of a material capable of enabling the generation and maintenance of a sufficiently high vacuum level. The lamination of the magnet and the material of the beam pipe are chosen to avoid eddy current effects during switching of the kicker magnet. In one embodiment, Ferrite Philips 8C11 may be used for the yoke of the kicker magnet to minimize eddy currents and aid compatibility with the ultra-high vacuum environment. The kicker magnet is operated at 50 amps to deflect the beam in the vertical direction. With this device, the beam can be switched on and off in less than 50 microseconds.

The depth of the dose deposition is measured by a range shifter system 1145. The range shifter is placed in the nozzle, behind the monitoring system, and, in one embodiment, consists of 40 degrader plates, which cover the full swept beam. Pneumatic valves can be used to move individual plates into the beam path. The mechanical movement of the beam takes approximately 30 ms per plate. Using a single command, removing all plates from the beam path can occur in approximately 200 ms. Of the 40 plates, 36 are made of polyethylene and have a thickness equal to an antproton range of 4.7 mm in water. One plate has only half that thickness to allow for a more precise depth scanning at low energy. Three plates are made of thin lead foil and can be used to enlarge the spot size, if desired. The projected dead time contribution from the range shifter system is 35-40 seconds, 30 seconds to move plates into the beam path and 5-10 seconds to remove the full stack. Additional devices can be used to contour the beam, including specially designed metal alloys. These devices may be used at the outlet of the nozzle [not shown] and can conform the beam to the cross-sectional size and shape of the target area within the patient.

In preferred embodiments, a beam is formed and delivered without the use of degraders or other devices to physically contour the beam. The inclusion of barriers, structures, or other materials within the beam line can cause the unwanted generation of particles, such as pions, neutrons and gamma rays, that will dose the patient without any beneficial medical purpose. To vary dosage levels, it is preferred to use a variable energy synchrotron whose energy level can be modified as needed to deliver antiprotons to the requisite depth.

In another embodiment, shown in FIG. 9, a delivery pipe 940 is directed through a series of magnets 919, 915, 917, 910 and positioned relative to a patient table 930. The delivery pipe 940 bends as it extends out from an accelerator [not shown], through a shielded support structure 905, and into the plurality of delivery heads 935 through the application of magnets 919, 910, 917, 915. Operationally, the fixed delivery mechanism can deliver an antiproton beam 920 from multiple directions without requiring a rotatable gantry. The present embodiment can therefore direct multiple antiproton beams 920 to target a single isocenter without requiring the more complex gantry structure. While the present embodiment is shown having three delivery points from which fixed beams 920 are emitted in the direction of the patient table 930, one of ordinary skill in the art will appreciate that, using the appropriate number and type of bending magnets, the beam line can be designed to deliver any number of fixed beam configurations directed toward the patient table.

More specifically, in the illustrated embodiment, the antiproton beam [not shown] enters into the structure 905 via the vacuum pipe 940. The vacuum pipe extends through one 135 degree bending magnet 910, present in line with the delivery pipe 940, and into a nozzle head 935. When activated by a control system [not shown], the bending magnet 910 operates to redirect the antiproton beam into a second vacuum pipe section 940a, into a first 90 degree bending magnet 915, and through a second nozzle head 935, if the 90 degree bending magnet 915 is activated by a control system [not shown]). If the 90 degree bending magnet 915 is unactivated, a first 45 degree bending magnet 917 is activated to redirect the antiproton beam into and through a third vacuum pipe section 940b, into a second 135 degree bending magnet 919, and through a third nozzle head 935. The first 45 degree bending magnet 917 and first 90 degree bending magnet 915 are shown in FIG. 9 as being co-located in the same area. Preferably the support structure 905 is designed to provide maximum rigidity to the beam line. The weight of the entire gantry is generally dominated by the bending magnets 919, 910, 915, 917 and appropriate balancing weights should be provided in the structure 905 to insure the gantry does not fall, tip, or otherwise become unstable.

Operationally, the antiproton beam is deposited in the patient preferably as a sequence of sequential pulses, directed from one, or a combination of several, delivery points defined by nozzles 935. For example, in operation, the 135 degree bending magnet 910 can be inactivated by a control system [not shown] to allow an antiproton beam to travel into and through a nozzle head 935 having a monitor and range shifter system [not shown], and into the patient [not shown]. Where a second beam impingement path is desired, e.g. through a second delivery point, the 135 degree bending magnet 910 can be activated by a control system [not shown] to allow an antiproton beam to be redirected into the first 90 degree bending magnet and, if activated, through a nozzle head 935 having a monitor and range shifter system [not shown] and into the patient [not shown]. Where a third beam impingement path is desired, the first 45 degree bending magnet 917 can be activated by a control system [not shown] to allow an antiproton beam to be redirected into the second 135 degree bending magnet and, if activated, through a nozzle head 935 having a monitor and range shifter system [not shown] and into the patient [not shown]. A beam impingement path is the pathway through the patient that is traveled by an antiproton beam to reach a target region.

As previously discussed, the number of antiprotons delivered in a single, directed application is preferably measured by a beam monitor system positioned in the nozzle 935. In one embodiment, the beam monitoring system comprises two monitoring subsystems providing two independent beam flux measurements. The two monitoring subsystems are substantially similar to those described in relation to the gantry configuration. Similarly, other methods and systems can be used to monitor the beam. Once the target number of antiprotons has been delivered into a patient through a delivery point, the beam is switched off preferably using a fast kicker-magnet [not shown] located in the beam line 940. The fast kicker magnet and associated support structures are substantially similar to those described in relation to the gantry configuration.

While a range shifter system and other additional devices can be used to control and contour the beam, as discussed in relation to the gantry configuration, in preferred embodiments a beam is formed and delivered without the use of degraders or other devices to physically contour the beam. The inclusion of barriers, structures, or other materials within the beam line can cause the unwanted generation of particles, such as pions, neutrons and gamma rays, that will dose the patient without any beneficial medical purpose. To vary dosage levels, it is preferred to use a variable energy synchrotron whose energy level can be modified as needed to deliver antiprotons to the requisite depth.

In both the gantry and fixed beam configurations, the patient table can be fixed or moveable. Where moveable, the patient table can be moved linearly along all three coordinate planes, x, y, and z, and rotationally across one or more coordinate planes, as needed. In a preferred embodiment, the patient table comprises an elongated rectangular bedding, preferably of sufficient firmness to maintain the patient on an even plane surface, that is affixed to a table frame that preferably has at least four legs connected, at their bases, to wheels. The frame is preferably a metallic structure capable of being tilted to modify the planar position of the bedding without requiring the concurrent repositioning of the patient. One of ordinary skill in the art will appreciate that numerous table designs can be with in various embodiments, including the one described by U.S. Pat. No. 6,152,599 incorporated herein by reference, without departing from the scope of the invention.

As further discussed below, a plurality of variables are monitored and modified to insure that the proper dosage is being delivered to the proper area within the patient. The position and quantity of each dose is determined by the application of an antiproton treatment protocol and cancer diagnostic procedure pursuant to one preferred embodiment. Through the diagnosis and protocol procedures, dose distributions of various shapes, from uniform to complex, can be constructed and delivered by modifying the beam impingement path and location on the patient, the number of antiprotons delivered, and the energy of the antiprotons. The antiproton beam, as delivered, is rapidly focused on the target area using magnetic fields in the form of a highly directed pencil beam positioned in three-dimensional space to insure the dose distribution substantially matches the distribution determined theoretically by Bragg Peak calculations.

In one embodiment, the gantry head can be rotated circumferentially relative to the patient to allow for the radial movement of the nozzle around the patient. The radial movement preferably covers a 180 degree arc above the patient table. Additionally, the patient table can preferably be rotated, both vertically and horizontally, to establish an appropriate beam delivery angle relative to the gantry head. In operation, singular doses can be delivered, through specific tissue pathways, and then terminated. If necessary, the gantry head and/or patient table can then be moved to position the patient for a subsequent exposure to an antiproton beam via a different tissue pathway. The patient table is preferably not repeatedly rotated in the course of a treatment to reposition a patient in order to avoid creating discomfort to the patient and because such table adjustments often use far greater time and technician assistance.

Where a target volume is being treated for which multiple doses delivered adjacent to one another may be needed it is preferred to use a sweeper magnet to move the beam, thereby speeding up adjustment time and obtaining greater precision relative to mechanical reconfigurations. One preferred sweeper magnet is a 40 cm long H-type laminated magnet with a 5 cm pole gap having a vacuum pipe made of insulator material to avoid eddy effects. Using this type of sweeper effect, the beam spot can be moved by about 10 cm. The current in the coils can be chosen at any desired value, preferably in the range of +/−500 amps, which corresponds to a magnetic field range of +/−0.8 Tesla. The sweeper magnet is used to perform the most frequent displacements of the antiproton beam. For adjacent irradiations requiring only a small change of current in the sweeper magnet, the time required to switch the beam off and adjust position should be below about 5 ms. For example, where a treatment requires 10,000 adjacent spots delivered to a single target area, total dead time may be limited to under one minute.

In another embodiment, the dose distributions of various shapes, from uniform to complex, can be constructed and delivered by transmitting a beam of antiprotons from a plurality of different delivery points fixed in space. Referring back to FIG. 9, a single isocenter 980, for example a tumor located in the brain of a patient, can be targeted via three different beam pathways using the three delivery points. Additionally, the patient table can be preferably rotated, both vertically and horizontally, to establish an appropriate beam delivery angle relative to the delivery points. In operation, singular doses can be delivered, through specific tissue pathways, and then terminated. The patient table is preferably not repeatedly rotated in the course of a treatment.

In preferred antiproton device configurations, an operator workstation comprising a data processor, data storage device, and display is in data communication with the delivery synchrotron, magnets, and delivery structures, such as the motorized drive gears attached to the gantry head and/or to the base of the patient table. The workstation is programmed to implement the antiproton treatment protocol developed for the patient. An operator initiates the workstation and indicates, through an interface, that the patent is positioned in an initial reference position. By positioning the patient in an initial reference position, the workstation can be informed as to where the patient sits in space and, therefore, move the gantry head and/or patient table into the proper position relative to the patient, for delivering the antiproton beam. Several methods may be used for positioning, including, but not limited to those which follow. The initial reference position can be established, for example, by placing the patient in a specific position relative to the table utilizing spine implanted radioopaque fiducials which may be implanted in the patient's spinal column permitting accurate repositioning of the patient to +/−1.7 mm. The initial reference position can also be established by placing the patient in a specific position relative to the patient table or by covering the patient with a sheet comprised of a grid of electronic contacts, each of said contacts being placed in a specific position relative to the patient's body. More specifically, in one embodiment, the grid of electronic contacts is interconnected by a conductive material and culminates in a single wire contact extending into a grid reader. The grid reader sends a signal into and through the contacts, receives responses from the contacts, reconstructs the grid structure in space, and transmits the grid configuration to the workstation. Operating on assumptions as to how that grid structure is positioned relative to the patient's body, the workstation can identify specific points on the patient's body.

Beginning with the patient in an initial reference position, the workstation transmits a signal to the motorized drive gears of the gantry head and/or patient table informing the drive gears to move the gantry head and/or patient table into a specific position based upon the angle and path by which an initial antiproton dose will be delivered into the patient. Where a fixed beam line configuration is being used, only the patient table is manipulated to achieve a specific position based upon the angle and path by which an initial antiproton dose will be delivered into the patient.

With the patient position positioned, the workstation transmits a signal to the beam monitor system informing it what amount of antiprotons are to be delivered and also transmits a signal to the range shifter system informing it of the dosage depth prior to activating the delivery synchrotron to accelerate (or decelerate) and deliver antiprotons of the desired energy level to the system. In one embodiment, the delivery system is activated and antiprotons are delivered to an appropriate depth and in an appropriate number, as measured and monitored by the range shifter and beam monitoring systems respectively. Preferably a plurality of procedures are used in parallel to monitor the quantity and depth of dose delivery. For example, a first procedure can comprise the workstation actively communicating scanning parameters to the ranger shifter and beam monitoring systems. Concurrently, a second procedure can be implemented in which the workstation passively monitors the activities of the ranger shifter and beam monitoring systems. Passive monitoring can be achieved by detecting the number and location of antiproton annihilations within the patient, as further discussed below, and deriving the associated energy level and number of antiprotons delivered. The data generated from the second procedure can be compared to the parameters of the first procedure to cross check the accuracy of the monitoring and shut down systems. If a discrepancy is identified, an automatic shutdown procedure can be effectuated, where the antiproton source is turned off, the fast kicker magnet is activated, and/or a solid beam shutter is deployed.

In a second preferred embodiment, the workstation transmits a signal to the beam monitoring system informing it what amount of antiprotons are to be delivered and also transmits a signal to the delivery synchrotron to accelerate and deliver antiprotons at a specific, predefined energy level, thereby eliminating the need for degraders, range-shifters or other such mechanism that may generate unwanted particles, such as pions, neutrons and gamma rays. In one embodiment, the delivery system is activated and antiprotons are delivered to an appropriate depth and in an appropriate number, as measured and monitored by the beam monitoring system. Preferably, similar parallel procedures as discussed above are used to monitor the quantity and depth of dose delivery.

After the initial antiproton irradiation is completed, the parameters for the position of beam scan are preferably modified to enable the irradiation of an entire target area. Beam repositioning is preferably performed with the beam switched off. As previously discussed, beam repositioning can be effectuated by gantry head movement, table movement, or the use of a deflecting magnet (such as a sweeper magnet), depending on the antiproton delivery device being used.

In a gantry configuration, to insure beam focus on the designated target area, referred to as the isocenter, it is preferred that the shape of the poles of the 90 degrees bending magnet and of the sweeper magnet are designed to produce a displacement of the swept beam which is substantially exactly parallel to its direction and to maintain the focusing of the beam at the isocentric plane independently of the setting of the sweeper magnet. The shape of the scanned beam is preferably sweeper invariant. The precision of the beam is measured at better than 1 mm for beam parallelism during scanning (independent of sweeper position), change of beam shape during scanning (independent of sweeper position), isocenter stability (independent of gantry angle), and beam position reproducibility after a change of the beam energy.

In addition to the above controls, for both the fixed beam and gantry configurations, a preferred embodiment additionally has a plurality of backup controls to shut down or otherwise block the undesired antiproton irradiation of a patient. Antiproton beams are automatically controlled by a fast kicker magnet. In case the kicker magnet fails to activate, another form of beam shut down should be immediately deployed, such as the switching off of the antiproton accelerator. Alternatively or in combination, a mechanical beam shutter can be used to block the patient from antproton exposure.

In a preferred embodiment of the antiproton gantry device, shown in FIG. 10a, the gantry 1050a is combined with a plurality of detectors 1060a that enable the imaging of certain patient tissue areas subjected to antiproton radiation. A patient [not shown] is positioned on a patient table 1065a. Antiproton beam 1070a enters gantry 1050a and is directed toward a target volume 1075a. As previously discussed, a plurality of different configurations can be used to direct beam 1070a toward volume 1075a, and the configuration shown in FIG. 10a is merely an exemplary embodiment. The detectors 1060a are arrayed in a configuration that avoids obstructing beam 1070a while concurrently exposing the detector array 1060a to antiproton annihilation emissions that can be used to conduct real-time imaging, as further discussed below.

Similarly, in a preferred embodiment of the fixed beam device, shown in FIG. 10b, the fixed beam system 1050b is combined with a plurality of detectors 1060b, 1062b that enable the imaging of certain patient tissue areas subjected to antiproton radiation. A patient [not shown] is positioned on a rotatable patient table 1065b. An antiproton beam line [not shown] enters gantry 1050b and is directed by action of a plurality of beam magnets toward a target volume 1075b. As previously discussed, a plurality of different configurations 1070b can be used to direct an incoming beam toward volume 1075b, and the configuration shown in FIG. 10b is merely an exemplary embodiment. The detectors 1060b, 1062b are arrayed in a substantially spherical upper detector configuration 1060b and substantially spherical lower detector configuration 1062b that avoids obstructing the plurality of beams 1070b while concurrently exposing the detector array 1060b, 1062b to antiproton annihilation emissions that can be used to conduct real-time imaging, as further discussed below.

The detectors are preferably made of a high atomic number, high-density material capable of interacting with gamma rays to create an electromagnetic shower. The shower energy is substantially contained inside a volume, each having a radius of two times the Moliere radius and having a length of approximately 20 $X_0$ radiation lengths. In one embodiment, the detector assembly is supported by a carriage, which can be rotated around the target axis running on a bent, nearly semicircular track. The detector may also be moved radially by a screw arrangement to a specified range of distance from the target to the crystal face.

In specialized high-energy physics experimentation, energetic charged particles and gamma rays, which are produced when an antiproton annihilates at rest on a proton and which then move radially away from that annihilation site, are detected and tracked back to a common point, referred to as the vertex. The process of tracking the energetic charged particles and gamma rays back to their common point of origination is referred to as vertex reconstruction. To effectively perform vertex reconstruction, the detectors used are preferably. designed to detect particles and/or radiation that have the highest likelihood of escaping a patient's body with the least amount of scattering or other perturbations that can complicate determinations of where the particle and/or radiation had originated.

Assuming an antiproton beam penetrates and stops at the center of a sphere of water having a 15 centimeter (cm) radius and annihilates, only those particles having energy greater than given by the stopping range of 15 cm of water will escape the sphere and be capable of being detected. Relative to charged kaons, neutral kaons (short), and neutral kaons (long), muons and charged pions have the highest probability of escaping the 15 cm sphere. Neutral pions decay in less than 0.025 microns from the point of annihilation into a pair of gamma rays that escape with energy carried by the pion.

Charged pions escaping material undergo substantial amounts of scattering, thereby increasing the complexity of vertex reconstruction. When being emitted out of 15 cm of water, charged pions having momenta less than about 160 MeV/c stop in the water and are not detected, while charged pions having momenta in excess of about 150 MeV/c scatter laterally, relative to the direction of the linearly formed track, by a root mean square of approximately 7 millimeters. The change of direction is dependent upon the particle's momentum, the particle's charge, and the material through which the particle is passing.

Although lateral displacement improves as particle momentum increases, even at the higher momenta, pion lateral scattering is at or around 1.5 mm, thereby limiting imaging precision to plus or minus 1.5 mm. This limitation decreases as the site of annihilation approaches the surface.

In a preferred embodiment, vertex reconstruction is performed using neutral pion decay gamma radiation. Unlike charged pions, gamma rays have a high probability of escaping a material body without undergoing substantial interactions which cause scattering and skew vertex reconstruction calculations. Further, the pair of gamma rays emitted can be traced back to the point where the neutral pion decayed and, because neutral pions decay within 0.025 microns of the annihilation point, can provide a more accurate representation of where the annihilation occurred. In a typical annihilation event, the mean number of gammas emitted for each antiproton annihilation event is four (two for each neutral pion), and can be as high as 10.

Operationally, vertex reconstruction is performed by relying on the detection of multiple points along the shower axis and the use of those multiple points to generate a vector localizing a common origination area. It is preferred that any heavy inorganic scintillators used to detect gamma rays have one or more of certain desired characteristics, including, high stopping power to maximize the probability of complete absorption of the incident energy, high timing resolution, high energy resolution, minimum dead time, wavelengths of emission that match with the spectral response of the photodetectors, mechanical ruggedness, radiation hardness, chemical stability in normal atmospheric conditions, and reasonable cost. Existing heavy scintillators meet certain of these criteria, including high luminous efficiency measured in photons/ MeV (NaI(TI) and CsI(TI)), high density/high atomic number (BGO), short Moliere radius (BGO and $CeF_3$), high initial photon intensity measured in photons/MeV/ns with high timing resolution ($BaF_2$), and high luminous efficiency and wavelength suitable for silicon photodiodes (CsI (TI) and $CdWO_4$). Proper selection of a detector provides for a further benefit of gamma ray shower detection over charged particle detection is speed. Shower detection can be done using a fast scintillator, less than 15 nanoseconds, thereby allowing a faster response than charged particle tracking.

Tungsten (W), sodium iodide doped with thallium (NaI (TI)), and lead tungstate ($PbWO_4$) are three materials which can preferably be used for shower detection. Sodium iodide activated by thallium is a well-known material used for scintillation applications. NaI(TI) has a high luminescence efficiency and. spectroscopic performance with minimal significant self absorption of the scintillated light. Lead tungstate is a highly efficient and fast scintillator with one of the shortest radiation lengths and Moliere radii among the known scintillators, satisfactory light yield for this energy range, and high radiation stability. Radiation lengths for NaI(TI), CsI (Ti), $PbWO_4$, BGO, Tungsten (W), and Iridium (Ir) are 2.59 cm, 1.86 cm, 0.89 cm, 1.12 cm, 0.323 cm, and 0.27 cm, respectively. The Moliere Radius for NaI(TI), $PbWO_4$, and W are 4.5 cm, 2.2 cm, and 0.8 cm respectively. The density for NaI(TI), CsI(TI), $PbWO_4$, BGO, Tungsten (W), and Iridium (Ir) are 3.67, 4.53, 8.28, 7.13, 19.4, and 22.4, respectively. The decay time for NaI(TI) is 250 ns while for $PbWO_4$ it is between 5 and 15 ns. For BGO and CsI(TI), the decay times are 300 ns and 0.9/7.0.mu.S. The light output for NaI(TI), CsI(TI), $PbWO_4$, and BGO are 1.0, 0.85, 0.01, and 0.15, respectively. Another material usable for the present application includes uranium, which has the requisite Moliere radius and material density. However, because it is not actively sensitive to the shower, it will have to be combined with an active scintillator. Using layers of tungsten, for example, in combination with uranium can provide a satisfactory detector device.

When using tungsten, one can employ the sensing element in a matrix, such as a 3.23.times.3.23.times.3.23 mm.sup.3 matrix, or in a crossed 3.23.times.3.23.times.200 mm.sup.3 hodoscope plastic scintillator a to sample the shower's charged particles passing between sandwich plates. Locating the vertex with a precision on the order of 500 microns is possible using these techniques. When using lead tungstate, one can use a 9.times.9.times.9 mm.sup.3 matrix or a crossed 9.times.9.times.200 mm.sup.3 hodoscope sensor array. Th radiation length of lead tungstate is 2.7 times greater than tungsten. Although the preferred approach is dependent upon a plurality of technical, as well as economic considerations, one consideration favoring the smaller shower localization of tungsten over lead tungstate is its ability to separate the gamma pair of the neutral pion decay. As the momenta of neutral pions increase, lead tungstate loses efficiency at separating decay gammas relative to a tungsten shower detector.

Preferably, the detectors are surrounded by a shielding structure to isolate the detectors from the surrounding environment. In one implementation, NaI(TI) crystals are surrounded by an active plastic shield, a passive LiH shield, and a low activity thick lead shield which, in combination, have a cosmic rejection efficiency around 98%. Further, the detectors are preferably supported by a carriage structure to enable efficient rotation around a target axis.

Referring to FIGS. 10c through 10r, a plurality of detector configurations is shown particular to each calorimeter imager material used. Imagers for NaI and BGO are not shown because NaI is similar to CsI and BGO is similar to PbWO.sub.4. FIGS. 10c and 10d show preferred detector configurations for brain imaging using PbWO.sub.4 as the calorimeter imager material. In FIGS. 10c and 10d, a beam pipe 1083d delivers an antiproton beam to a predesignated area within the patient's brain 1085d. The beam direction and imager 1086d are fixed relative to each other. The patient is positioned on a table 1084d. In use, a patient will first be positioned between detector elements, as shown in FIGS. 10a and 10b, and then the elements are assembled into a portion of a spherical shell sharing the center with the annihilation region, appropriately accounting for straggling and multiple straggling limits. Sufficient resolution can be achieved by having the calorimeter elements point approximately to the annihilation site. When annihilation occurs, a plurality of gamma rays 1087d are emitted, due to the decay of neutral pions generated in the course of the annihilation, which extend from the target region 1085d with an opening angle of approximately 30 degrees taken from the point of annihilation. The gamma radiation may have an opening angle less than 30 degrees, but not more than 30 degrees relative to each other. In one embodiment, the imager length (20 radiation lengths) is 17.8 cm. The inner radius size is 0.89 cm.times.0.89 cm with the outer radius size being 1.8 cm.times.1.8 cm. The maximum mass is approximately 1556 kg.

FIGS. 10g and 10h, 10k and 10l, and 10o and 10p show a similar detector configuration using CsI(TI), Ir, and W as calorimeter elements, respectively. A beam pipe 1083h, 1083l, 1083p delivers an antiproton beam to a predesignated area within the patient's brain 1085h, 1085l, 1085p. The beam direction and imager 1086h, 1086l, 1086p are fixed relative to each other at least during detection. The patient is positioned on a table 1084h, 1084l, 1084p. In use, a patient will first be positioned between detector elements, as shown in FIGS. 10a and 10b, and then the elements assembled into a portion of a spherical shell sharing the center with the annihilation region, appropriately accounting for straggling and multiple straggling limits. Sufficient resolution can be achieved by having the calorimeter elements point approximately to the annihilation site. When annihilation occurs, a plurality of gamma rays 1087h, 1087l, 1087p are emitted, due to the decay of neutral pions generated in the course of the annihilation, which extend from the target region 1085h, 1085l, 1085p with an opening angle of approximately 30 degrees taken from the point of annihilation. The gamma radiation may have an opening angle less than 30 degrees, but not more than 30 degrees relative to each other. In one embodiment, or CsI(TI), the imager length (20 radiation lengths) is 37.2 cm, the inner radius size is 1.86 cm.times.1.86 cm, the outer radius size is 5.7 cm.times.5.7 cm and the maximum mass is approximately 3172 kg; for Ir, the imager length (20 radiation lengths) is 10.8 cm, the inner radius size is 2.7 cm.times.2.7 cm, and the maximum mass is approximately 1073 kg; for W, the imager length (20 radiation lengths) is 12.92 cm, the inner radius size is 0.32 cm.times.0.32 cm, the outer radius size is 5.7 cm.times.5.7 cm, and the maximum mass is approximately 1137 kg; and for BGO (not shown), the imager length (20 radiation lengths) is 22.4 cm and the inner radius size is 1.12 cm.times.1.12 cm. For non scintillators, such as Ir and W, preferably approximately 50% of the space in the length is dedicated to a plastic scintillator read out of the shower in a hodoscope's geometry.

FIGS. 10e and 10f show detector configurations for torso imaging using PbWO.sub.4 as the calorimeter imager material. A beam pipe 1083f delivers an antiproton beam to a predesignated area within the patient's torso 1085f. The beam direction and imager 1086f are preferably fixed relative to each other. The patient is positioned on a table 1084f. As previously stated, in use, a patient will first be positioned between detector elements, as shown in FIGS. 10a and 10b, and then the elements are assembled into a portion of a spherical shell sharing the center with the annihilation region, appropriately accounting for straggling and multiple straggling limits. Sufficient resolution may be achieved when the calorimeter elements point approximately to the annihilation site. When annihilation occurs, a plurality of gamma rays 1087f are emitted, due to the decay of neutral pions generated in the course of the annihilation, which extend from the target region 1085f with an opening angle of approximately 30 degrees taken from the point of annihilation. The gamma radiation may have an opening angle less than 30 degrees, but not more than 30 degrees relative to each other. In one embodiment, the imager length (20 radiation lengths) is 17.8 cm, the inner radius size is 0.89 cm.times.0.89 cm, the outer radius size is 1.8 cm.times.1.8 cm, and the maximum mass is approximately 3618 kg.

FIGS. 10i and 10j, 10m and 10n, and 10q and 10r show a similar detector configuration using CsI(TI), Ir, and W as calorimeter elements, respectively. A beam pipe 1083j, 1083n, 1083r delivers an antiproton beam to a predesignated area within the patient's torso 1085j, 1085n, 1085r. The beam direction and imager 1086j, 1086n, 1086r are fixed relative to each other. The patient is positioned on a table 1084j, 1084n, 1084r. In use, a patient will first be positioned between detector elements, as shown in FIGS. 10a and 10b, and then the elements are assembled into a portion of a spherical shell sharing the center with the annihilation region, appropriately accounting for straggling and multiple straggling limits. Sufficient resolution may be achieved when the calorimeter elements point approximately to the annihilation site. When annihilation occurs, a plurality of gamma rays 1087j, 1087n, 1087r are emitted, due to the decay of neutral pions generated in the course of the annihilation, which extend from the target region 1085j, 1085n, 1085r with an opening angle of approximately 30 degrees taken from the point of annihilation. The gamma radiation may have an opening angle less than 30 degrees, but not more than 30 degrees relative to each other. In one embodiment, for CsI(TI), the imager length (20 radiation lengths) is 37.2 cm, the inner radius size is 1.86 cm.times.1.86 cm, the outer radius size is 3.8 cm.times.3.8 cm and the maximum mass is approximately 6328 kg; for Ir, the imager length (20 radiation lengths) is 10.8 cm, the inner radius size is 2.7 cm.times.2.7 cm, and the maximum mass is approximately 2500 kg; for W, the imager length (20 radiation lengths) is 12.92 cm, the inner radius size is 0.32 cm.times.0.32 cm, and the maximum mass is approximately 2618 kg. For non scintillators, such as Ir and W, approximately 50% of the space in the length is dedicated to a plastic scintillator read out of the shower in a hodoscope's geometry.

With respect to performance, the angular acceptance achieved in the crystal barrel spectrometer is approximately 6 degrees (100 mrad). Without adjacent cell interpolation, the calorimeter imager materials, operating in the aforementioned brain imager and torso imager configurations, have the following degrees of angular acceptance: for brain imager configurations, the angular acceptance of CsI(TI), PbWO.sub.4, BGO, W, and Ir is 103 mrad, 49 mrad, 62 mrad, 18 mrad, and 15 mrad respectively. For torso imager configurations, the angular acceptance of CsI(TI), PbWO.sub.4, BGO, W, and Ir is 53 mrad, 25 mrad, 32 mrad, 9.2 mrad, and 7.2 mrad respectively. If interpolation is implemented, a 300% gain in resolution may be achieved for certain calorimeter imager materials operating in certain configurations, upwards of a 1000% gain in resolution for materials such as PbWO.sub.4. The highest angular resolution can be achieved with W or Ir, although Ir may be expensive to use.

Diagnosis and Treatment Strategy

Cancer is diagnosed using a variety of methods, a few of which are discussed herein. A patient suspected to have cancer maybe imaged using x-ray, CT, MRI, radioactively labeled tracer uptake, thermography, ultra sound and PET scanning. A medical practitioner skilled in the art of cancer diagnosis will understand how to use these technologies to yield an image that can indicate the presence of an unusual mass, and possibly, cancer.

In one preferred embodiment, a patient is treated in a medical facility in which antiproton radiation therapy can be delivered. A schematic plan layout of an exemplary medical facility is provided in FIG. 11. The exemplary medical facility 1100 comprises a plurality of areas dedicated to standard medical facility functions, including examination rooms, maintenance areas, reception areas, waiting rooms, janitorial rooms, utilities, staircases 1187, elevators 1180, a lobby 1190, and staff areas, such as staff offices, meeting rooms, lunch areas, patient record keeping. Preferably, sizeable rooms internal to the facility 1185 are used for staff offices and/or examination rooms, rooms adjacent to the treatment area 1160 are used for patient preparation and changing, larger rooms 1170 are used for meeting or waiting areas, the smaller rooms 1175 are used for utilities or janitorial purposes, and the other rooms 1165 are used for storing patient records, secretarial functions, lunch rooms, smaller staff offices, and at least one dosimetry room and health physics room.

The illustrated medical facility 1100 further comprises areas specialized for the delivery of antiproton therapy. A plurality of treatment rooms 1103 surrounded by heavy shielding 1135 is located in the back of the facility 1100. A control room 1130 is integrally provided with each treatment room 1103. In one room 1003, a MRI 1145 is provided proximate to a CT simulator 1155. In a set of second rooms 1103, a patient table 1120 is situated proximate to a delivery point 1115 integrally attached to a delivery device, such as a fixed beam or gantry device. Additionally, a treatment chair 1140 and an array of detectors [not shown] can also be situated proximate to the delivery point 1115 and patient table 1120. In a third room 1103, a calibration system 1125 is provided that enables an operator to calibrate the operation of the beam transport system 1105 and delivery synchrotron [not shown]. Operationally, an antiproton beam is caused to travel through the beam transport system 1105 and bend by force of a plurality of bending magnets 1110, which are housed in a support structure.

Depending upon a centralized schedule of operation, one of the plurality of beam lines directed into specific treatment rooms 1103 will be active and delivering a predesignated dose of antiprotons to a patient 1124 positioned on a patent table 1120. Antiprotons traveling through the beam transport 1105 will be directed into the appropriate beam pipe that feeds a particular treatment room 1103. The beam pipe as shown terminates in a gantry or vertical/horizontal beamline. Referring to FIG. 11a, an exemplary beam line 1105a integrated with a medical facility 1100a is shown in the context of delivering an antiproton beam to a fixed beam antiproton delivery device. Two fixed beams 1125a are generated, focused on a target volume 1130a, by action of a plurality of bending magnets selectively bending antprotons traveling through a beam pipe 1140a. A person familiar with high-energy physics will understand how to produce, collect, cool, decelerate and extract antiprotons through the application of vacuums pumps, magnets, radio-frequency cavities, high voltage instruments and electronic circuits. Antiprotons circulate inside vacuum pipes in order to avoid contact with matter with which they annihilate. The vacuum should be optimal, therefore several vacuum pumps, which extract air, are placed around the pipe. The magnets used include dipoles, which serve to change the direction of antiproton movement and insure they stay within the circular track, and quadrupoles, which are used as lenses or focusing magnets to insure that antiproton beam size is smaller than the vacuum pipe size. Electric fields are used to modify antiproton energy levels and are provided for by radio-frequency cavities that produce high voltages synchronized with the rotation of antiprotons around the ring. While the medical facility 1100, 1100a has been described in relation to a specific design and layout, one of ordinary skill in the art will appreciate that other space configurations can be used, depending upon the particular conditions of the location and the needs of the facility.

A patient is positioned in a diagnosis area that can have one of, or a combination of, several diagnostic devices. One diagnostic device can include a magnetic resonance imaging (MRI) scan in which a patient is subjected to an external, uniform magnetic field and radiofrequency energy that excites protons in the patient's body and subsequently produces signals with amplitudes dependent on relaxation characteristics and spin density. Abnormalities can be detected by identifying unusual signals that indicate a particular region has a different proton density than normally expected. Another diagnostic device that can reveal tissue structure and therefore identify unusual masses is computer tomography (CT) scanning. CT scans are performed by passing x-rays through a patient, at a large number of angles, by rotating the x-ray source around the patient. A plurality of detector arrays, located opposite the x-ray source, collect the transmission projection data in the form of various data points. The data points are synthesized into a tomographic image, or imaged slice, of a patient. The variation in transmission data is indicative of tissue density and can be used to identify unusual masses-in the body.

A third possible diagnostic device is a positron emission tomography (PET) scan in which the patient is administered, through an intravenous injection, a positron-emitting radioactive substance comprising a form of glucose that reacts with tissues in the body, in proportion to metabolic activity. By measuring the different amounts of positrons released by healthy and cancerous tissues, a computer creates an image reflective of the biological activity occurring within the patient. Because cells from many cancers have a higher affinity for certain positron-emitting radioactive substances, such as F.sup.18 labeled glucose, the tumor area may be imaged. PET scans can be combined with x-ray based scans and MRI scans to confirm that an unusual structure may, in fact, be cancerous. More specifically, PET scans can be overlaid onto, or combined with, MRI or CT images to generate an integrated image that shows tissue structure associated with metabolic activity.

Output from one or more of the aforementioned diagnostic devices can be used by a medical practitioner, including technicians, nurses, radiologists, oncologists, and other medical professionals, to determine whether the patient has cancer and, if so, the location, extent, and stage of the cancer. In a preferred embodiment, shown in FIG. 12, at least one of the diagnostic scans from the PET scan 1305, MRI scan 1310, and/or CT scan 1315, is stored in an operator workstation 1320, transmitted to an antiproton treatment protocol station 1325, and used to assist in the development of an antiproton based treatment regimen. Alternatively, only the data representing key treatment parameters may be transmitted to the antiproton treatment protocol station.

Referring back to FIG. 11, the patient, once imaged, is taken to an antiproton treatment protocol station. The station can be co-located with the diagnostic machinery, placed in a separate office within the same building, or located in a completely separate facility. The schematic representation in FIG. 11 is provided for example purposes only.

Having identified and quantified the tumor location, a treatment protocol using antiproton radiation is developed. In a preferred approach, data representing the tumor size and location is transmitted from imaging technologies, as previously described, to an antiproton treatment protocol station. The treatment protocol station applies a set of analyses to determine the amount of antiprotons, antiproton energy sufficient for treatment, and preferred delivery pathways and communicates that protocol to an antiproton radiating and imaging station, as previously described. The antiproton treatment protocol station is in data communication with the imaging station used or, alternatively, is capable of receiving data stored on media, such as a disk or CD-ROM.

In one embodiment, shown in FIG. 12, the treatment protocol station comprises a display 1350, print-out device 1355, storage device 1360, modem or network control card 1365, and processor 1370 capable of communicating with the display (any type of monitor), print out device (any type of printer), storage device, and modem/network controller and of implementing a plurality of instruction sets for determining the amount of antiprotons, antiproton energy sufficient for treatment, and preferred delivery pathways given a tumor size and location. The amount of antproton radiation needed to terminate a mass is calculated, along with the amount of energy needed to deliver an antiproton to the mass depth. Using equations to determine the amount of energy deposited in collateral tissue and the residual energy plus annihilation event radiation effects, such as caused by the emission of particles like alpha particles, the energy deposited in the mass, along with the lateral spreads and Bragg Peak contours, can be determined. Once done, an energy deposition profile can be generated that covers the entire mass with sufficient antiproton induced radiation by summing multiple Bragg Peaks, assuming a plurality of spot scans performed at varying depths within the tumor region. The amount and energy level of antiprotons, for each location to be irradiated, defines the protocol, which is then sent to the antiproton radiation and imaging device, as previously discussed. During operation, a preferred embodiment monitors, through a beam monitoring system and range shifter or a delivery synchrotron, the actual dosage being delivered to insure it correlates with the desired calculated dosage. To the extent a range shifter is used, antiproton losses, caused by the degradation process, need to be calculated and incorporated into all beam monitoring calculations to insure accurate determination of actual antiprotons delivered to the patient.

As an example, a patient is diagnosed with a 1 cubic centimeter (cc) tumor located 10 centimeters below the skin surface. The diagnosis occurs through a combination of MRI and PET scans, which indicates a mass having a high metabolic rate in the patient's chest cavity. Using the location and tumor size data, the amount of antiprotons to be used to annihilate the target region is determined. One preferred method of determining the amount of antiprotons needed is by assuming the density of tissue to be around 1 gram per cc, assuming 500 rads will be sufficient to terminate the cancerous cells, and equating the relative biological effect (RBE) of antiproton radiation in the target volume to that of heavy ions having a 30 MeV recoil (RBE=5). This reflects the fact that at least one 30 MeV recoil heavy ion is produced for each antiproton annihilation event. Because 500 rads is approximately equivalent to 30.times.10.sup.9 MeV per gram, the total number of antiprotons needed to deliver 500 rads is 10.sup.9. It should be noted that, if the RBE of the chosen radiation were lower, as with photons, a greater amount of radiation, as measured in rads, will have to be delivered to the same target region in order to terminate the cancerous cells. For example, photon radiation has a RBE of 1, thereby requiring 2500 rads to have the same cell terminating effect as antiprotons, which, when equated to heavy ions, has a RBE of 5.

To determine the amount of energy 10.sup.9 antiprotons should have in order to reach 10 cm below a surface, one can use a TRIM calculation, as found in Zeigler J. F., Biersack J. P., and Littmark U., "Stopping and Range of Ions in Solids,", Vol. 1, 1985 (Pergamon Press, NY). Applying a TRIM calculation demonstrates that an antiproton beam energy of approximately 10.sup.8 MeV will achieve an end-of-range position that is 10 cm below the surface in a patient. Given that, like protons, antiprotons are low linear energy transfer particles and that only a small portion of antiprotons annihilate prior to reaching the target region, approximately 30 MeV of the 10.sup.8 MeV is deposited in the target region, while 78 MeV is deposited in collateral tissue. Assuming the volume of collateral tissue between the skin and target area is 9 cc (1 cm.times.1 cm.times.9 cm), the damage inflicted by traveling antiprotons can be defined by a RBE of 1.2 (20% greater than protons), and damage is uniformly spread across the collateral tissue, the collateral damage is equal to approximately 168 rads ((1.2.times.78 MeV/antiproton .times.10.sup.9 antiprotons)/9 cc), which is tolerable and therefore does not require a multiple pathway dosage profile (although it may be done if desired). Therefore, combined the protocol produces a recommended treatment plan: one exposure of 10.sup.9 antiprotons having an energy of 108 MeV.

In dealing with tumors having a volume greater than 1 cc, multiple doses, spread across a region, may be preferred to minimize collateral tissue damage in any single location. For example, some lung and prostate cancers are intermediate sized tumors and can range, on average, around 150 cc and 35 cc with average surface depths of 12 and 6 cm, respectively. Head and neck tumors may be irregularly shaped and in some embodiments, multiple doses may be utilized to cover the target region.

In either case, the high degree of localization provided by antiproton radiation therapy preferably allows for one or more of the following: (1) the termination of cancer cells with minimal fractionation requirements; (2) producing tumor cell injury by causing numerous double strand DNA breaks and by inducing cell membrane injury of trans-membranal surface proteins, i.e. by interfering with EGFR (epidermal growth factor receptor) and VEGF (vascular endothelial growth factor receptor) transduction signaling; (3) sparing injury to tumor-adjacent antigen serving macrophage dendritic cells, which facilitate tumor lysis by T-cells in the tumor microenvironment; (4) avoiding injury in the tumor microenvironment to lymphokine activated killer (LAK) T-cells, which become effector cells causing tumor lysis when served with tumor antigens by dendritic cells, an important immunologic activity in facilitating the body's natural defenses against tumor growth; (5) permitting the progeny of tumor sensitized effector LAK T-cells to provide cell lysis of distant microscopic tumor metastatic implants; and (6) causing less hematopoietic injury, which is common in photon regimens, since the bone marrow will be spared the effects of radiation exit dose and dose fall off. This is of particular importance with the increasing use of simultaneous chemotherapy-photon radiation therapy protocols in a variety of cancers, which often lead to blood count depressions that necessitate interruption of treatment. The highly conformal nature of antiproton radiation will avoid this adverse result.

In one preferred embodiment, the treatment protocol station will have a computer-implemented software program capable of taking the requisite input data, namely tumor size and location, and, as shown in FIG. 13, outputting impact graphs superimposed on the scanned images of the patient's tumor, as generated from conventional therapies. A tumor body 1305 is identified and located relative to a patient's anatomy. The tumor body 1305 is positioned in an area within the patient's brain 1310. A plurality of delineated antiproton dosage regions 1315 are defined relative to the tumor body 1305. The dose regions 1315 can be defined in numerous ways, including by percent dosage relative to calculated dose requirements or by absolute dosage amounts, with higher dose regions generally being centered within the plurality of dose regions 1315 and lower dose regions extending to the periphery.

It should be noted that, because of the ability to precisely deliver high amounts of energy into an area without high accompanying collateral damage, a medical practitioner does not need to cover an entire mass with antproton radiation, but rather, can selectively target highly sensitive areas within a tumor volume to achieve tumor mass destruction with minimal radiation. For example, because tumors rely on fragile blood vessel networks to fuel their rapid growth, it may be possible to kill an entire tumor mass through the directed application of antiproton radiation on areas responsible for providing primary blood supply. By irradiating critical blood vessels one can induce angiolysis, thereby shutting down essential blood supply to a tumor. Similarly, tumors may be killed using antiproton radiation by causing blood vessel swelling such as in AVM's (arterio-venous malformations) which will result in the eventual cut off of a tumor's blood supply. Tumors may also be killed by biologically isolating them through the application of antiproton radiation circumferentially and sparing normal structures interior to the tumor, such as the urethra coursing through a malignant prostate gland. Circumferential antiproton radiation may also induce fibrosis around a tumor mass isolating the tumor and causing it to necrose.

It should further be noted that a substantial number of repeated treatments is not required. Treatment fractionation is required in conventional therapies because of the inability to drive high enough radiation levels to target tissue without causing high collateral damage. Lower target radiation levels, though sufficient to kill dividing cells, are not sufficient to kill resting cells. As a result, multiple treatments have to be applied in order to kill the target cancer cells, and because of the rapid dividing nature of cancer cells, they are more impacted than the collateral cells which have time to repair after radiation exposure. The preferred methods and systems disclosed herein enable the delivery of high radiation levels in target tissue, thereby killing both resting and dividing cancer cells, without causing unacceptable levels of damage to healthy tissue.

Optionally, a patient may also be imaged using a PET scan after the antiproton radiation exposure is completed. Typically, to perform PET scanning, a patient is administered a glucose-tagged radioactive substance that decays inside the body and, in the process, releases positrons which, when detected, can be used to generate an image. Conventional PET scans are limited by the need to have the patient, PET imaging station, and radioactive isotope source (the radiopharmaceutical of appropriate activity) all proximate to each other.

Specifically, PET applications rely on the use of biologically active radiopharmaceuticals where radioactive isotopes in the radiopharmaceutical emit positrons. These isotopes are typically generated through the use of synchrotrons, such as the RDS cyclotron, manufactured by Siemens, which is a frequently used PET device. It incorporates a computer terminal to control the flow of production, and a biosynthesizer unit to carry out the chemical synthesis of radiopharmaceuticals. Using the synchrotron, a stream of charged particles, such as protons or deuterons, bombard a collection of stable, sometimes enriched, isotopes and interact with a subset of those isotopes. Three nuclear reactions are commonly used for the production of C-11 and F-18, the most common PET isotopes. These reactions are: $^{14}N(p, \alpha)^{11}C$, in which the interaction of $^{14}N$ with a proton is then followed by the emission of an alpha particle, resulting in $^{11}C$, $^{18}O(p,n)^{18}F$, in which the interaction of $^{18}O$ with a proton is then followed by the emission of a neutron, resulting in $^{18}F$, and $^{20}Ne(d, \alpha)^{18}F$, in which the interaction of $^{20}Ne$ with a deuteron is then followed by the emission of an alpha particle, resulting in $^{18}F$. Radiopharmaceuticals, made from these radioactive isotopes, are then introduced into a patient's body where the decay of the isotope is monitored.

While many radioactive isotopes can be produced in the cyclotron, the isotopes produced are preferably amenable to human PET use and, therefore; (1) are capable of emitting positrons when they undergo radioactive decay and transform from an unstable isotope into a stable one. (2) Because such isotopes tend to emit positrons relatively quickly, the isotope half-life is preferably long enough to allow for a patient to be administered the substance and placed in a position to be scanned. Furthermore, it is preferred that the isotopes are readily incorporated into a useful radio-pharmaceutical by chemical synthesis. The most commonly generated isotopes include carbon-11 (half-life 20 minutes), nitrogen-13 (half-life 10 minutes), oxygen-15 (half-life 2 minutes), and fluorine-18 (half-life 110 minutes). Because of these short half-lives, some PET installations have cyclotrons proximate to the PET machine. For example, at the University of Iowa, a compact medical cyclotron is used to generate high energy protons or deuterons by forcing the particles to traverse the cyclotron several hundred times and, during each orbit, receive about 90 keV of energy. When the energies are high enough, the particles are removed through electrostatic deflection and are made to impinge upon small volume hollow metallic cylinders filled with a non-radioactive gas or liquid, causing nuclear reactions to take place within the cylinder and generating the appropriate isotopes.

For certain applications, some of the preferred methods and systems disclosed herein complement the use of PET-specific cyclotron and biosynthesizing stations to perform a PET scan. Conventional PET systems are used to measure and study biological functions, such as glucose uptake. In one embodiment, PET administration is used in combination with certain preferred methods and systems disclosed herein to conduct PET scans. A patient is administered a PET-isotope labeled glucose molecule in order to identify enhanced glucose uptake areas in the body. The detector array incorporated into the antiproton delivery device can be used to monitor resulting decay, thereby repurposing detectors used for antiproton annihilation tracking and measurement for PET scanning. When treating with antiprotons, a medical practitioner can then directly compare PET scanning results with antiproton treatment results. One of ordinary skill in the art will appreciate that, in addition to the aforementioned characteristics, the antiproton delivery detector system for this embodiment should be sufficiently sensitive to differentiate between the decay generated by increased uptake areas of the radiopharmaceutical and the decay generated by the general uptake of the radiopharmaceutical throughout the body.

Additionally, one preferred embodiment enables the in-situ generation of PET isotopes. The exposure of human tissue to antiproton radiation generates a plurality of unstable isotopes, including, for example, oxygen-15, that are radioactive and emit a positron as a decay product. More specifically, when introduced into a target region, antiproton interactions generate oxygen-15, nitrogen-13, and carbon-11 as by-products. After the appropriate period of time (depending on the half life of the isotope), the generated isotopes decay, emitting positrons. The positrons travel a short distance in the target area before striking an electron. When this collision occurs, two gamma rays are simultaneously produced and travel away from each other at 180 degrees, toward the detector assembly already present for tracking gamma radiation generated from neutral pion decay. Each time two detectors detect a gamma ray simultaneously, the annihilation is recorded and the vertex, or point of gamma production, is determined. One of ordinary skill in the art will appreciate that, by reconstructing the location of the plurality of vertices, one can determine where the highest concentrations of isotope generation occurred, where the highest concentrations of tissue existed, and, by extrapolation, where cancerous tissue was located, assuming correlations between isotope generation, tissue density and cancerous tissue.

Further, because those radioactive by-products are generated through antiproton annihilations in the region of interest, they better image only the region of interest. A difference between conventional PET imaging and the PET imaging aspect of preferred embodiments is that the conventional PET image reveals regions of enhanced glucose uptake whereas the image in a preferred embodiment reveals a region where antiproton annihilations have occurred. Conventional PET scanning is dependent upon the uptake, by tissue, of radioactively tagged glucose, which may or may not be confined to a particular region of interest. As a result, a substantial amount of gamma radiation is emitted by positron-electron annihilations that are outside the region of interest and the result of the uptake of tagged glucose by healthy tissue elsewhere in the patient. These various emissions represent noise in the form of an undesired background signal relative to the gamma emissions from the areas of interest. In one preferred embodiment, the signal to noise ratio is greatly enhanced by the elimination of extraneous radiation emissions from areas outside the target region. It should be noted, however, that the intrinsic resolution of the conventional PET image and the resolution of the PET image produced by preferred embodiments are similar and that both images are degraded in absolute resolution due to diffusion and migration of the PET isotopes in tissue before the radioactive decay occurs that emits the positrons.

Another advantage of the PET imaging aspect of a preferred embodiment is that standard PET cameras can be used to collect the image and the same detectors used for conventional PET imaging can be used to detect antiproton-generated PET. As the radioactive decay of the PET isotope does not occur promptly with respect to the antiproton annihilations, computer modeling of the diffusion and migration of the PET isotopes in tissue should be done in order to reconstruct where the annihilation took place. A higher resolution image, relative to PET images, is obtainable by imaging the higher-energy gamma ray emissions that are associated with the decay of the neutral pions that are created in the antiproton annihilation event, as the neutral pions decay nearly instantaneously after the neutral pion is created. It should be noted that, as previously discussed, the detection of the gamma rays from neutral pion decays generally uses a different type of detector than the gamma ray detectors used in a standard PET camera.

A further aspect of a preferred embodiment is the use of the low background noise characteristic of antiproton-produced radioisotopes, coupled with the short half lives of the radioisotopes, to image flow and/or diffusion characteristics within vessels or through tissue. Antiproton annihilations in blood or other fluids create short-lived radioisotopes within the blood or fluids. The most common radioisotopes that are produced in human fluids are $^{11}C$, $^{13}N$, and $^{15}O$, which have half lives of 20, 10, and 2 minutes, respectively. Circulatory blockages or hemorrhages can be imaged using standard PET imaging equipment to follow the diffusion of small volumes of blood or fluid that is initially irradiated with a low-intensity, highly localized pulse of antiprotons. A low-intensity pulse of antiprotons creates a small volume of radioisotopes that will flow with the blood or fluid in the local region. The path of the flow is readily imaged from the emitted radiation because the background intensity is negligible, as described above, and the resulting signal-to-noise is high. The short half lives of the radioisotope species result in large signals relative to background levels for ease of detection and short total lifetimes for low residual effects.

The various methods and systems described above provide a number of ways to carry out the invention. The present invention contemplates the coverage of numerous variations of the disclosed embodiments, which, although not specifically detailed herein, are variants, examples, or species of the disclosed systems, devices, and processes. Of course, it is to be understood that not necessarily all objectives or advantages described may be achieved in accordance with any particular embodiment of the invention. Thus, for example, those skilled in the art will recognize that the methods may be performed and/or the systems built in a manner that achieves or optimizes one advantage or group of advantages as taught herein without necessarily achieving other objectives or advantages as may be taught or suggested herein.

Ser. No. 60/370,605; Titled: Antiproton Deceleration; Filed: Apr. 30, 2002

According to one aspect of embodiments of the present invention, a method decelerates antiprotons. The method comprises providing antiprotons to a particle accelerator ring. The antiprotons have a first momentum distribution with a first average momentum. The method further comprises operating the particle accelerator ring so as to apply electromagnetic fields to the antiprotons as the antiprotons travel around the ring. The method further comprises selectively applying the electromagnetic fields to the antiprotons as the antiprotons travel around the ring, such that the antiprotons have a second momentum distribution with a second average momentum less than the first average momentum.

Antiproton irradiation has utility in a variety of fields, including the treatment of cancerous tissue and the generation of radioisotopes within the body which are useful for imaging techniques and therapeutic treatment.

Currently, antiprotons are generated and used in experimental studies of elementary particles physics. These experiments are typically performed at large particle accelerators, such as the Tevatron at Fermi National Laboratory. The Tevatron includes various components which are designed to generate antiprotons, to accelerate these antiprotons to very high energies and momenta (typically to 1 TeV), and to collide these antiprotons together with other particles, such as protons. The results of the collisions can be analyzed to provide information regarding the physics of these and other elementary particles.

While these experimental studies of elementary particle physics require antiprotons with very high energies and momenta, other uses of antiprotons, such as the medical uses mentioned above, require relatively small energies and momenta. If the existing sources of antiprotons at such accelerators are to be used as sources of antiprotons for these other fields, the antiprotons have to be decelerated (i.e., the energy and momentum of the antiprotons will have to be reduced). In addition, to provide antiprotons to locations which are off-site from the particle accelerators, the antiprotons have to be decelerated sufficiently to enable them to be trapped in a container and transported to other locations. Because antiprotons are annihilated upon contacting matter, significant development has been performed to develop adequate containers (e.g., Penning traps) for transporting antiprotons.

Embodiments of the present invention decelerate the antiprotons by operating existing particle accelerators, which were designed to accelerate the antiprotons, under conditions which actually reduce the energy and momentum of the antiprotons.

A method of decelerating antiprotons, the method comprising: providing antiprotons to a particle accelerator ring, the antiprotons having a first momentum distribution with a first average momentum; operating the particle accelerator ring so as to apply electromagnetic fields to the antiprotons as the antiprotons travel around the ring; and selectively applying the electromagnetic fields to the antiprotons as the antiprotons travel around the ring, such that the antiprotons have a second momentum distribution with a second average momentum less than the first average momentum.

A method for decelerating antiprotons includes providing antiprotons to a particle accelerator ring. The antiprotons have a first momentum distribution with a first average momentum. The method further includes operating the particle accelerator ring so as to apply electromagnetic fields to the antiprotons as the antiprotons travel around the ring. The method further includes selectively applying the electromagnetic fields to the antiprotons as the antiprotons travel around the ring, such that the antiprotons have a second momentum distribution with a second average momentum less than the first average momentum.

Ser. No. 60/316,711; Titled: Non-Invasive Method of Cellular Termination Using Antiproton Reactions; Filed: Aug. 30, 2001

This invention relates to the field of the treatment of cancer and other diseases by using radiation. Specifically, it addresses the use of antiprotons to deliver the ionizing radiation to the body; the advantages of using antiprotons rather than x-rays, 10 gamma rays, electrons, protons, heavy ions, mesons, or any other particles; the method of delivering the radiation to the desired region of the body; methods of enhancing the energy deposition within the body; the production of antiprotons; the collection and storage of antiprotons; the transport of antiprotons; and the application of the therapy in centralized and dispersed facilities.

Radiation has been used to treat cancer and other diseases for many years. In general, radiation is used to kill cancer cells immediately or to damage cancer cells enough to prevent reproduction. The fundamental problems with all forms of conventional radiation therapy are the delivery of an adequate dose (micro-density of ionization) to the desired cells (localization) at the right time without damaging healthy surrounding tissue.

With conventional radiation therapies, delivery of a dose of radiation adequate to damage cancer cells within a tumor is balanced against the amount of collateral damage that that particular dose of radiation will cause to healthy tissue. The specific nature of the radiation determines what collateral damage is done to healthy tissue and also determines the number of treatments required to deliver a dose calculated to be sufficient to treat a tumor. Treatment planning typically involves detailed computer modeling for all incident forms of radiation. These exact calculational schemes are specific to a particular patient and treatment facility, but the mathematical principles underlying the calculations are generally applicable.

Localization, the deposition of ionizing radiation within the desired region of the body, is performed internally or externally. Radiation therapy performed internally can be administered by radiation implant or via radioimmunotherapy. The general term, brachytherapy, refers to the insertion of an implant containing radioactive material directly in the tumor. It requires both the invasive surgical insertion and surgical removal of the radioactive implant. It is limited in its ability to treat large tumors uniformly. Radioimmunotherapy is a radiation therapy that involves delivering radiation to the surface of a tumor via the use of monoclonal antibodies that are tagged with radioactive atoms. It is also limited in its ability to treat large tumors.

Radiation therapy performed externally uses different methods of localization depending on the nature of the radiation. Simple collimation using appropriate shielding is used to localize the radiation field in two dimensions. Controlling the depth distribution of the energy deposition depends on the specific nature of the radiation; whether it is electromagnetic, charged particle, or neutral particle. Again, the specific nature of the radiation also determines how well defined the localization can be and how much damage is done to adjacent and intervening healthy issue.

When the incident radiation is electromagnetic (e.g. x-rays), more ionizing radiation is produced near the surface than deeper within the body. Electromagnetic radiation, as opposed to charged particle radiation, always delivers some ionizing radiation at all depths in the body. Thus, localizing the depth distribution of ionizing radiation is inherently more difficult with electromagnetic radiation than with charged particle radiation. Complex methods for the enhancement of the three dimensional localization of ionization within the body are well developed. These methods involving the overlapping of intersecting radiation fields are known by such names as gamma knife, intensity modulated radiation therapy (IMRT), and dose sparing methods. All these techniques minimize the dose to healthy tissue by spreading out the entering dose over a large volume, but all of these techniques still lack a true capability for three-dimensional delivery.

When the incident radiation is in the form of high-energy charged particles, more energy is deposited at the end of range, that is, more energy is deposited just before the particle stops than when it enters the body. This is the Bragg peak effect and is the basis for localization in depth. The distance the charged particles travel in the body is approximately the same for all similar charged particles of the same energy. Higher energy particles travel further in the body than lower energy particles. Well developed techniques exist for delivering different energy protons (positively charged particles) to various locations in the body using a fixed or variable energy accelerator, beam transport systems, variable thickness degraders, scanning systems, patient positioning, and methods for correlating ionizing energy deposition with various methods of imaging the internal structures of the body. The choice of ionizing particle determines the density of ionization (dose to the tumor) versus position along the path of the particle.

Neutral particle therapy (neutron therapy) achieves localization with overlapping fields and or the use of pharmaceuticals containing an isotope that captures the neutron and subsequently decays into ionizing particles. This combined method known as boron neutron capture therapy (BNCT) requires the development of special boron containing pharmaceuticals preferentially absorbed by the cancerous tumor.

A second problem with all forms of radiation therapy is delivering the correct density of ionizing radiation to the individual cells to either destroy the cells immediately or damage them enough to induce programmed cell death. On the microscopic scale, there are significant differences in the density of ionization and the nature of the damage produced by the various forms of radiation. These differences are accounted for by the concepts of the radiation adsorbed dose (Rad) and the relative biological effect (RBE). Radiation oncologists use these known concepts to plan the treatments using photons, neutrons, protons, heavy ions, or other charged particles. A significant improvement over the state-of-the-art would be the ability to change the density of ionization depending on the location (low density in healthy tissue and high density in diseased tissue).

Another problem with all forms of radiation therapy is the timing of the radiation treatments. Because the cells have repair mechanisms, they are able to recover from sub-lethal doses of radiation. Cells have variable sensitivity to radiation depending on whether they are actively reproducing or are in the resting state. Radiation oncologists typically administer many sub-lethal doses of radiation delivered over several weeks to destroy all the diseased cells when they are most vulnerable to radiation and to allow the healthy cells to recover between irradiations. This fractionation of the treatment is a significant inconvenience to the patient and is a major cost factor. A significant improvement over the state-of-the-art would be the ability to deliver a single dose of radiation to a tumor that is capable of destroying resting cells (cells that are not in the process of dividing) as well as those which are actively 5 dividing.

Brief Description of the Drawings

There is an early publication that discusses the possibility of using antiprotons for biomedical applications. (L. Gray and T. E. Kalogeropoulos, "Possible Biomedical Applications of Antiproton Beams: Focused Radiation Transfer." Radiation Research 97, 246-252 (1984).) The paper specifically mentions the "focusing" of radiation due to heavily ionizing particles emitted from annihilation. The sharpness of radiation transfer combined with antiprotonic radiography is considered attractive for special applications. The paper mentions simultaneous viewing (imaging) and treatment of areas of interest. The paper correctly identifies "the emission of low velocity nuclear fragments from the annihilation" as "responsible for the high concentration of energy transfer at the stopping point."

The direct comparison of charged beams of ions such as protons, e12, and Ne20 is in error with respect to the ratio of ionization energy deposited inside a tumor to that deposited outside a tumor versus the mass of the incident beam. The paper contains a figure comparing proton, heavy ion, and antiproton ratios of energy deposited inside a tumor, to that deposited outside the tumor for various size tumors below the surface. The figure appears to be onceptually correct. The paper does not discuss the concepts of the differing density of ionization for heavy ions versus protons or antiprotons, the relative biological effect, or the concept of reducing the fractionation of treatment required in the use of conventional radiation therapy. The only tumors specifically mentioned in the paper are pituitary and ocular.

Figure 1:
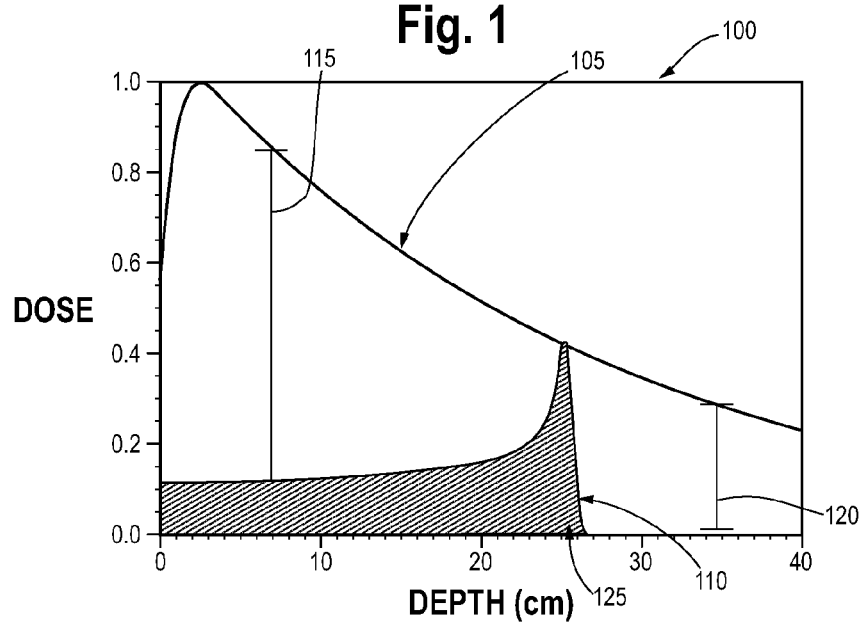
Figure 1A:
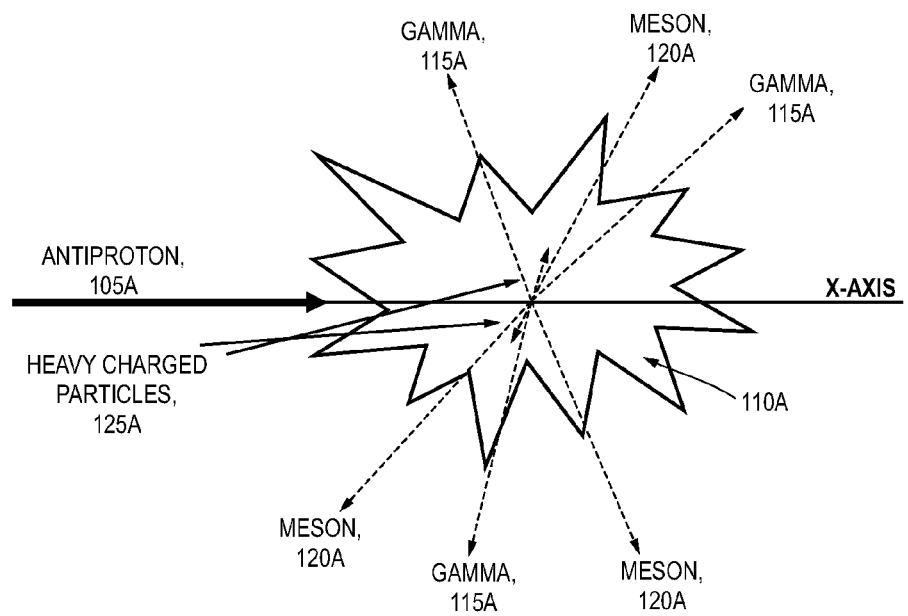
Figure 2:
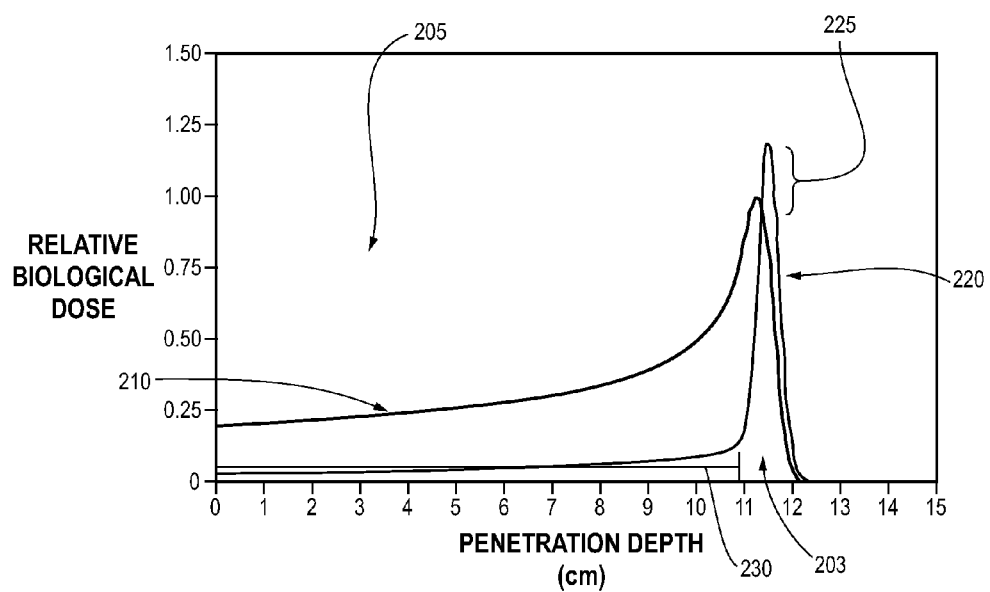
Figure 7:
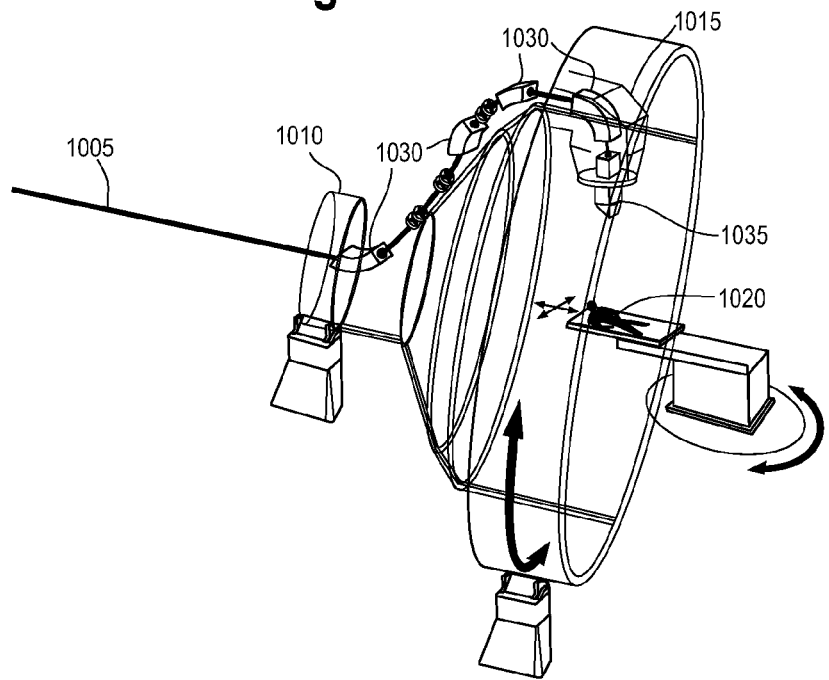
Figure 8:
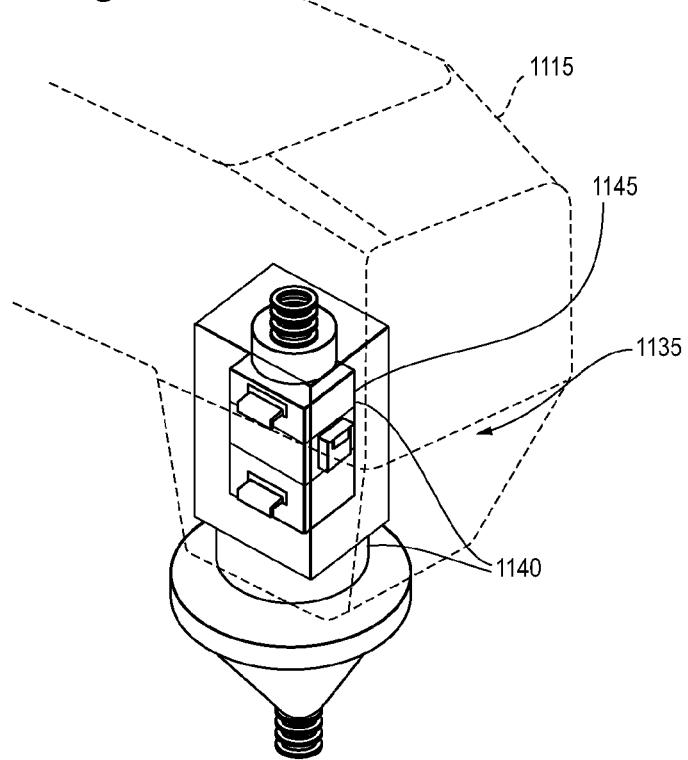
Figure 9:
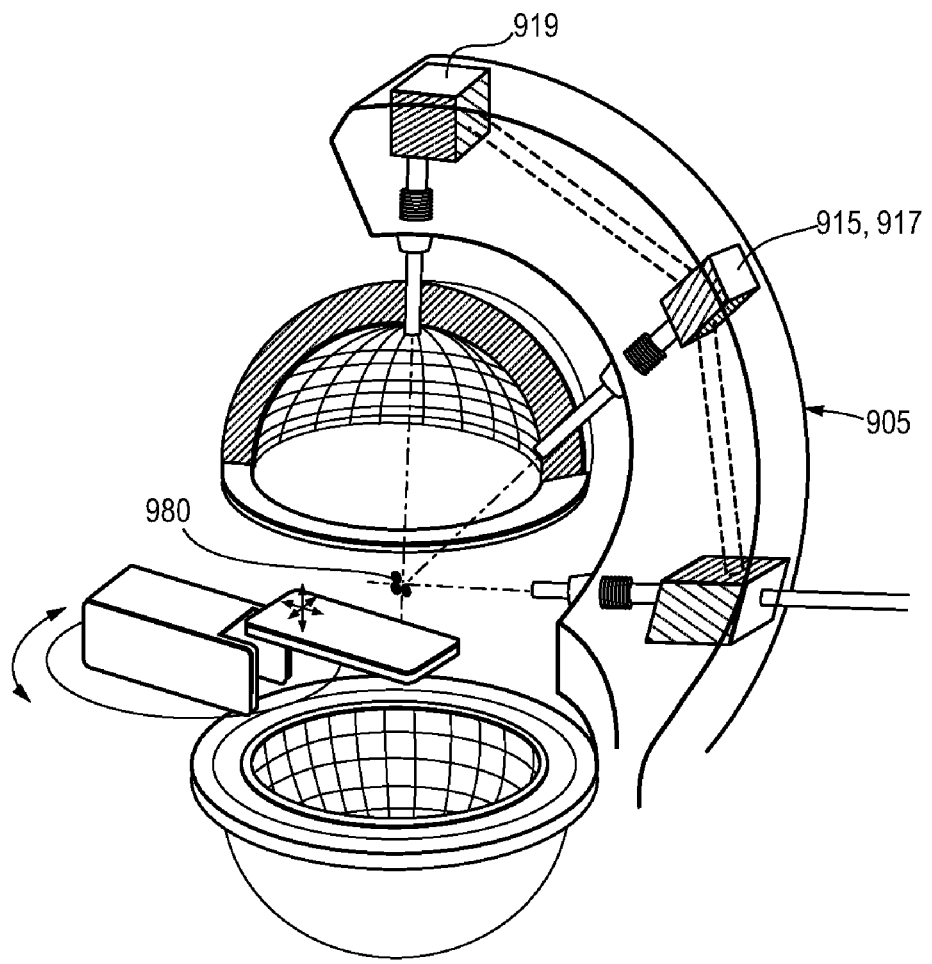
Figure 10A:
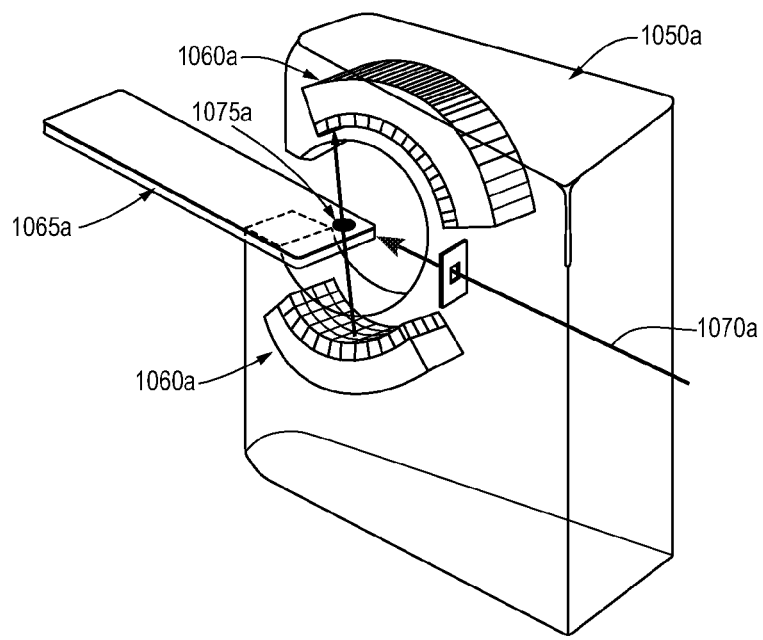
Figure 10B:
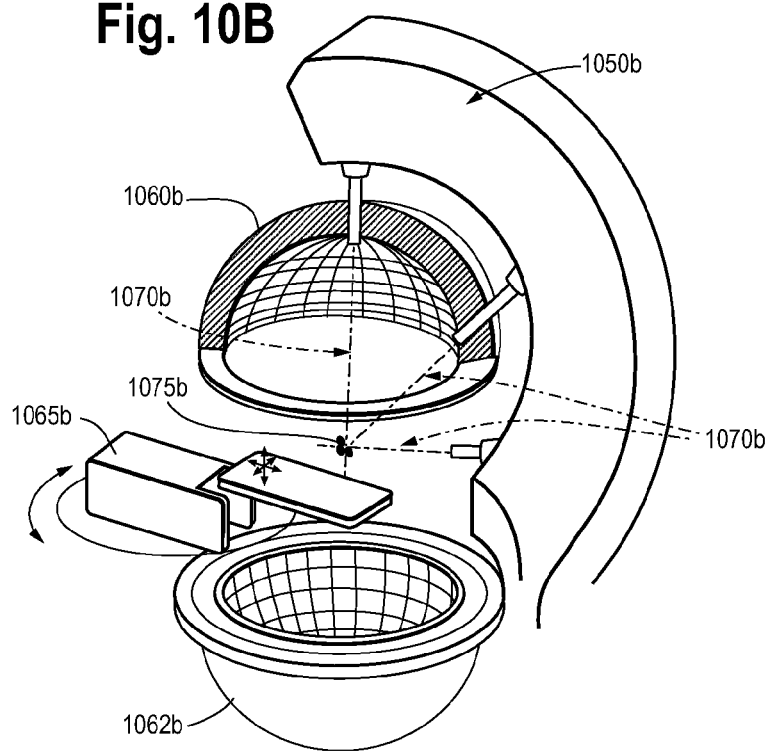
Figure 10C:
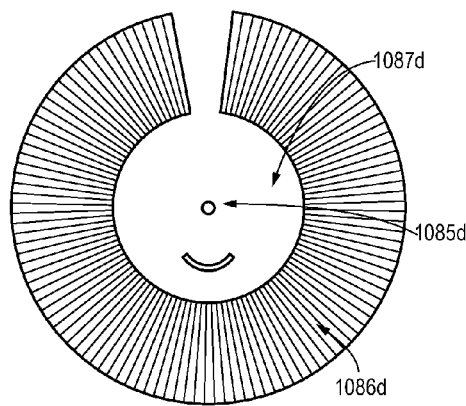
Figure 10D:
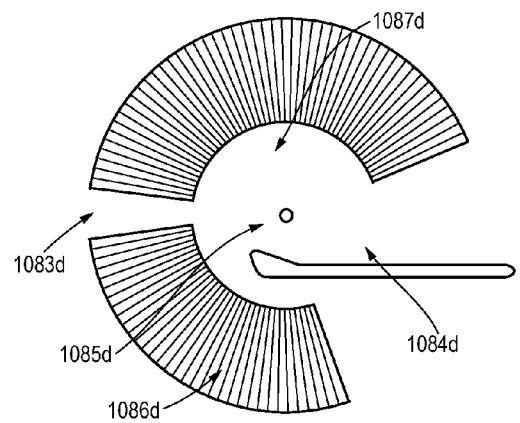
Figure 10E:
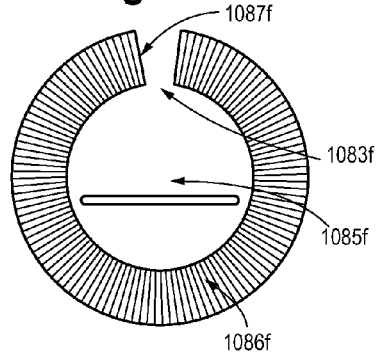
Figure 10F:
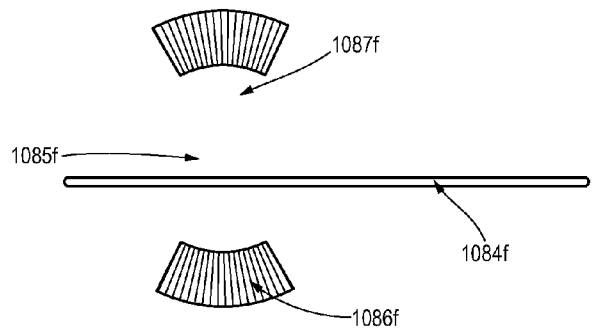
Figure 10G:
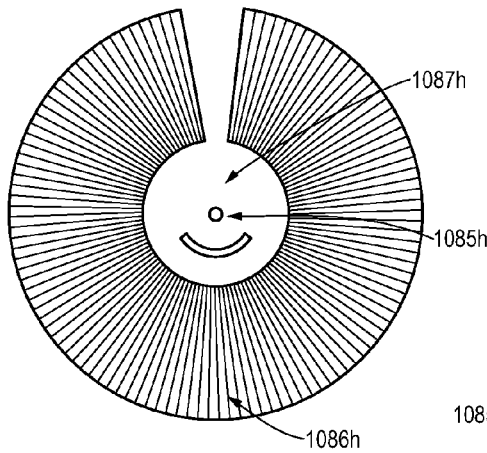
Figure 10H:
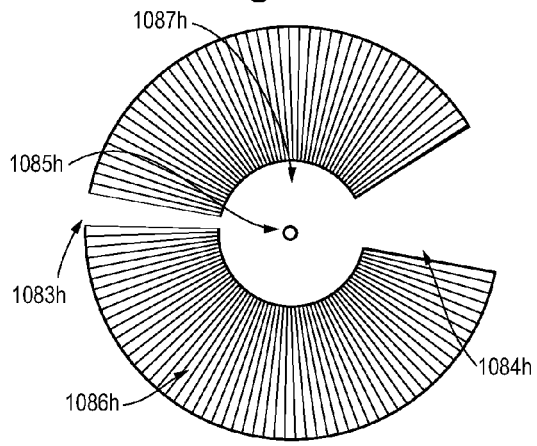
Figure 10I:
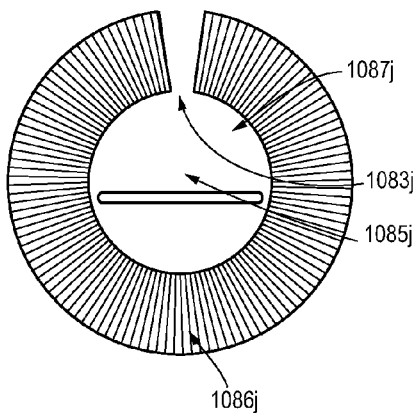
Figure 10J:
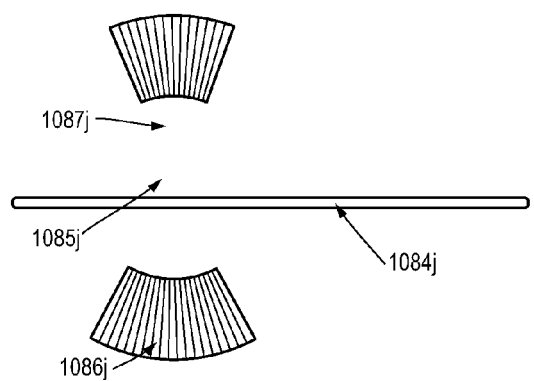
Figure 10K:
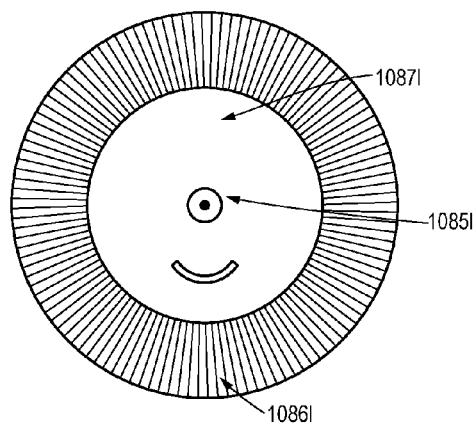
Figure 10L:
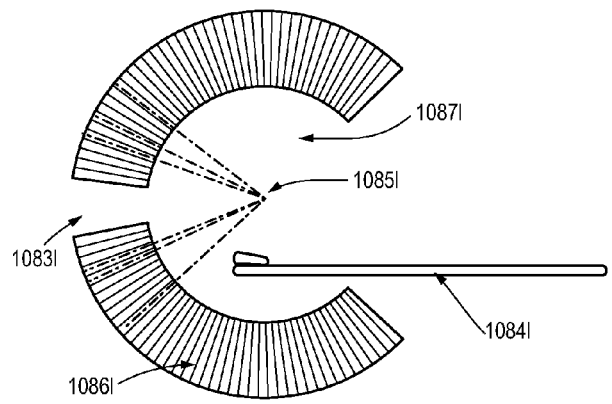
Figure 10M:
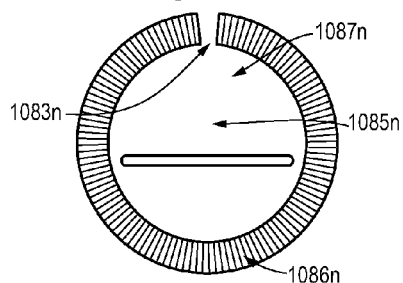
Figure 10N:
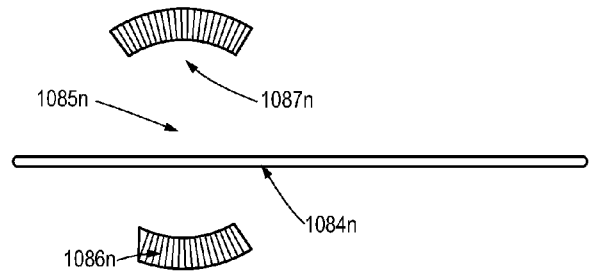
Figure 10O:
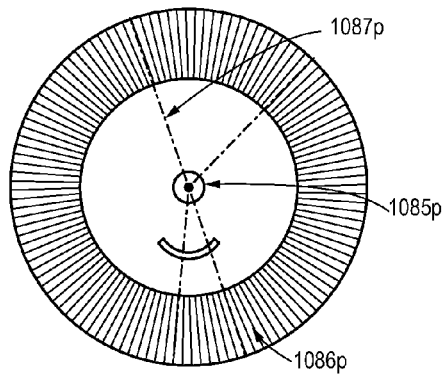
Figure 10P:
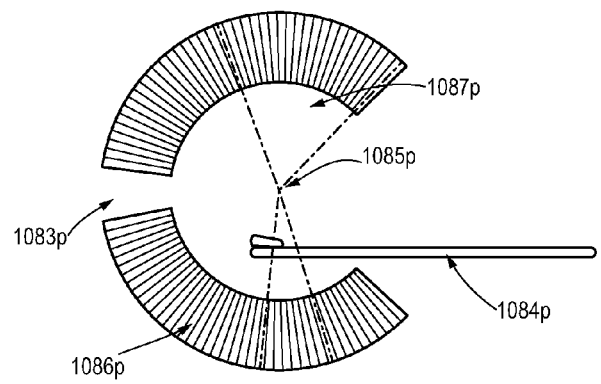
Figure 10Q:
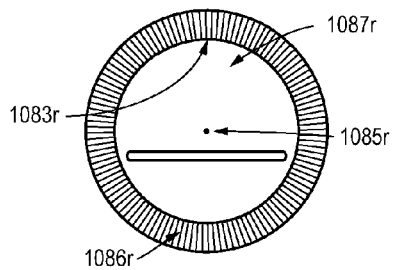
Figure 10R:
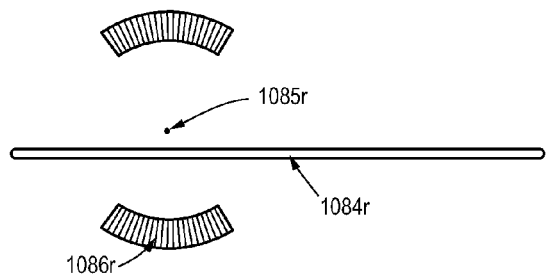
Figure 11:
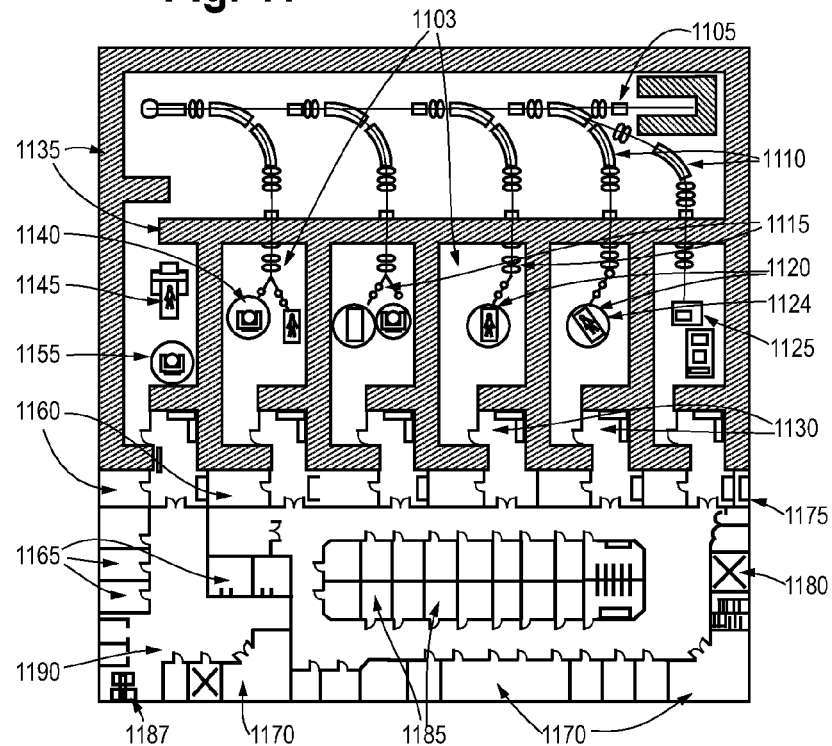
Figure 11A:
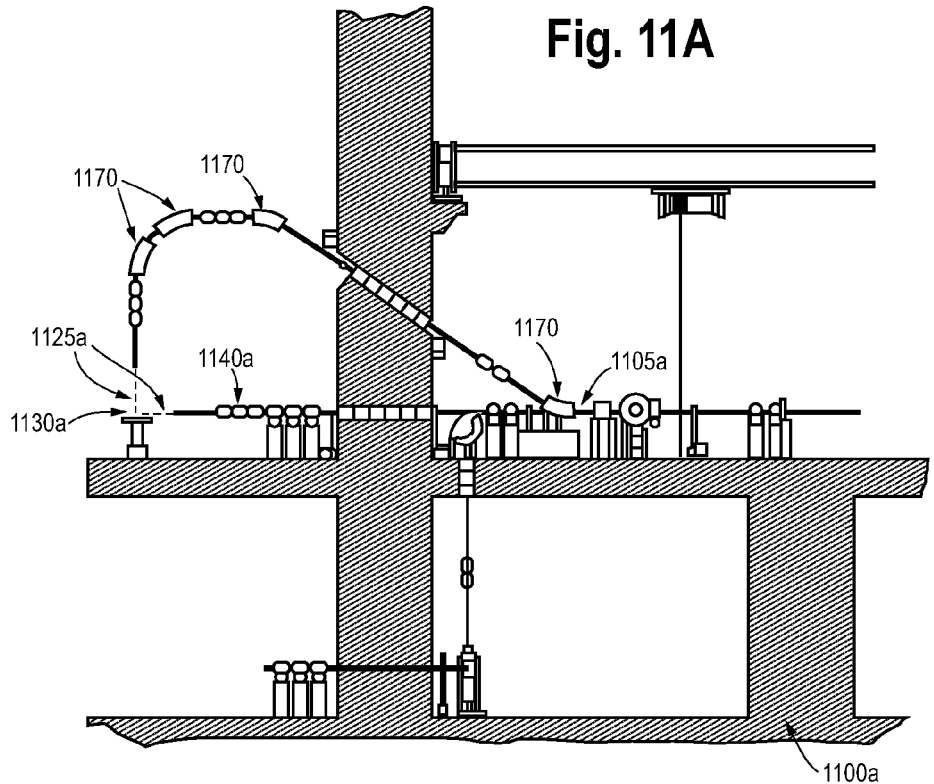
Figure 12:
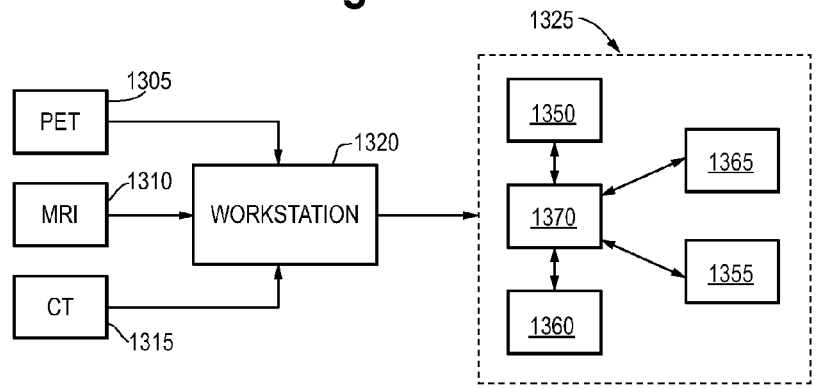
Figure 13:
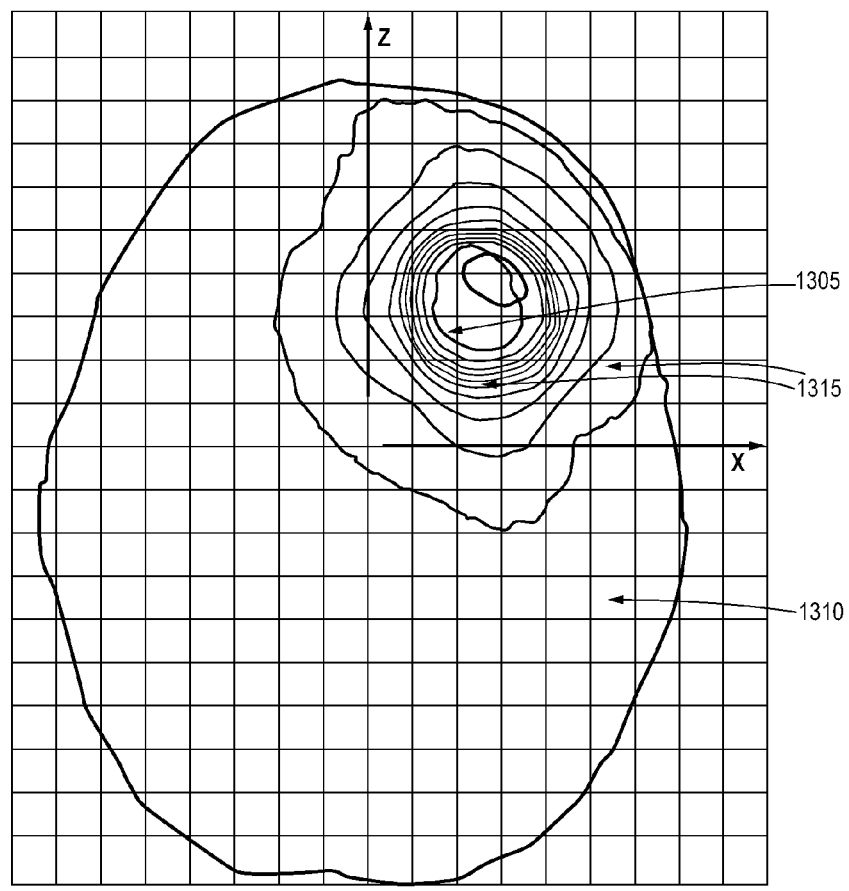

The lack of any discussion of possible methods of implementation, the lack of details regarding the differing biological effect for antiproton annihilation products and heavy ions, and the lack of any mention of reduced need for fractionation of dose delivery demonstrate that the combination of ideas involved in this patent disclosure has not been previously disclosed in this paper.

A subsequent publication (T. E. Kalogeropoulos and R. Muratore, "Antiprotons for Imaging and Therapy" Nuclear Instruments and Methods in Physics Research B40/41 (1989) 1322-1325), discusses the use of antiprotons for stereographic imaging. It only mentions the possibility of maximizing radiation to a tumor and minimizing radiation delivered to tissues outside the tumor. There is no specific mention of methods of implementation or detailed discussion of the advantages.

A later publication (R. A. Lewis, G. A. Smith, and S. D. Howe, "Antiproton Portable Traps and Medical Applications", Hyperfine Interactions (1997) 109) describes some advantages of antiproton therapy over proton therapy in the enhanced energy deposition at end of range and in the value of external pion detection for imaging of the stopping point of the antiproton beam.

A relative biological dose was estimated, but was acknowledged to be an underestimation since "charged pions, gamma rays, and nuclear fragments also deposit energy into the tumor." Also described is the fact that certain features would enhance accurate placement of dose. The concept of precise deposition of high linear energy transfer radiation into breast tumor masses was proposed by S. D. Howe (Synergistic Technologies) in a 1997 response to a Department of Defense Small Business Innovation Research request for proposals.

The disclosed method comprises a new method of delivering heavy ion irradiation to a localized region of the body for therapeutic purposes. The means to do this involves the production, deceleration, storage, acceleration, transport, and delivery of a beam of antiprotons to the desired region of the body. After delivery, upon stopping in the body, the antiprotons undergo nuclear reactions with atomic nuclei in the body. Because of these nuclear reactions, energetic heavy ions with the optimum total energy are created and delivered at the desired location within the body producing the correct density of ionization and therapeutic effects. The conversion of relatively low density ionizing particles of variable energy on entry (the antiprotons) to high density ionizing particles (the heavy ion recoils) at the end of range is a process that occurs naturally.

This new method of delivering heavy ion irradiation also has the added benefit of real-time imaging to confirm correct localization of the therapy within a patient. This disclosure addresses the applications and means of implementing the use of antiprotons for therapy.

Details of the Method

The particular and preferred embodiments and implementations of technologies related to production, deceleration, storage, acceleration, transport, and delivery of antiprotons to the creation and delivery of heavy ions within the body for therapeutic purposes depend on optimization of engineering choices. Several ways of assembling a working system are outlined below.

The production of antiprotons is routinely performed at large accelerator facilities such as Fermi National Accelerator Laboratory. The antiprotons are produced at velocities close to the speed of light and are accumulated in a storage ring where the spread in velocities is reduced and the velocity is adjusted by deceleration to an appropriate velocity to prepare for further deceleration. If the antiprotons are to be used immediately, the deceleration is halted at the required energy and the beam of antiprotons is transported to the patient via a beamline. Variable energies of antiprotons can be delivered in a single sitting to a single patient so that the range of the antiprotons within the body will be sufficient to reach all parts of the tumor.

An alternate implementation consists of continued deceleration of the antiprotons to almost zero velocity (<20 keV) for long-term storage in a portable magnetic trap such as a Penning trap. Long-term accumulation and storage of significant numbers of antiprotons (>10e8) can be performed in a portable device consisting of an arrangement of magnetic and electrostatic fields known as a Penning trap or variation of it. The antiprotons stored in a trap are not useful for immediate therapy, but they can be transported to another physical location for acceleration and use.

The Penning trap implementation for therapeutic delivery of antiprotons comprises using the trap as an ion source for an accelerator such as a linear accelerator, a cyclotron, or a synchrotron. The accelerator can be either of fixed or variable energy. The preferred implementation is a variable energy accelerator capable of increasing the energy of the antiprotons such that their ranges in the body are sufficient to reach all parts of the tumor within the body. The fixed energy implementation comprises accelerating the antiprotons to an energy greater than that required to reach the tumor and then using a variable thickness degrader to adjust the energy and range appropriately. This second method requires the fabrication of multiple specialized boluses (typically fabricated from paraffin or polyethylene) for each patient.

The accelerator, beam transport, and beam handling systems are preferably modifications and extensions of existing technology, but newer technologies may be used as well. Except for the ion source, the accelerator, beam transport, and beam handling systems for antiprotons are essentially the same as for protons. Antiprotons have the opposite charge from protons, which means that reversing the magnetic and electric fields will produce the same behavior for antiprotons as for protons. A normal RF, sputter, or duoplasmatron ion source for protons could be replaced with a Penning Trap (a Penning Trap is described in the U.S. Pat. Nos. 5,977,554 and 6,160,263).

Implementation of the method under either implementation scenario requires the calculation of the incident energy of the antiprotons to reach the various parts of the tumor. The energy depends on the total path length and the composition and density of the intervening healthy tissue. The methods for performing such calculations are well understood, but limited in accuracy by the prior knowledge of exact composition and densities of all intervening materials along the antiproton path. The exact overlap of the heavy ion irradiated volume with the tumor can be confirmed in real time by using position sensitive detectors for the pi mesons and/or gamma rays which result from annihilation to reconstruct the location of the annihilation radiation, i.e., the spatial location of the point of creation of the heavy ion. An alternative implementation of this idea is to use Positron Emission Tomography (PET) or Single Positron Emission Computed Tomography (SPECT) imaging to locate the position of the short-lived positron emitting isotopes created at the point of annihilation in real time.

The dose calculation methods used for x-ray, proton, or heavy ion therapy are not adequate for antiproton therapy outlined in this disclosure. The total radiation dose to various locations in the body and the resulting biological effects depend on the energy of the antiproton as it slows down in the body before annihilation and the dense ionization from the heavy ions produced subsequently. The motions of the antiprotons on entry produce a relatively low density of ionization and a biological effect that is the same or very similar to that of protons. The energetic heavy ions created within the body have very short ranges and produce dense ionization with a much greater biological effect relative to protons. The calculations needed for treatment planning will take into account the differences in the primary radiations (antiprotons and heavy ions) and their differing biological effects. The new combination of high-density ionization, (with heavy ions and the potential to kill resting cells with a single irradiation), and low-density ionization on entry (antiproton irradiation) is the basis for antiproton therapy. The detailed treatment protocols are patient specific, but the basic requirements are the same in almost all cases:

1) Create uniform, localized damage to the tumor sufficient to induce immediate or programmed cell death.
2) Minimize the incident radiation to healthy tissue and reduction of the total body dose to minimize the side effects to the patient.
3) Avoid severe inflammatory or necrotic tissue response
4) Eliminate or minimize the need for fractionated dose delivery.

These requirements place severe constraints on the absolute accuracy of dose localization, dose delivery, and dosimetry at all locations within the tumor.

Dosimetry, the measurement of the integrated radiation dose at each location in the body, can be obtained in several different ways. One possible implementation involves measuring the number of incident particles using an induction pick-off or a thin transmission detector. Such implementations are well understood and operate on the same principles as those used at a proton or heavy ion irradiation facility. A second possible implementation is to measure the total incident dose by detecting the mesons and/or gamma rays produced on annihilation of the incident antiprotons. This is also a real-time measurement that can be tied back to the beam rastering and/or beam blanking for precise dosimetry control of individual voxels. A third possible implementation is to measure the short-lived positron emitting isotopes produced at the time of incident antiproton annihilation. This third implementation is not performed in real time and is not amenable to active beam control during irradiation.

The methods for positioning the patient and the beam are the same or similar to those used for proton or heavy ion therapy. These methods include horizontal positioning of the patient with either fixed or rotating gantry and fixed or scanned beam. An alternate method uses a horizontal fixed or scanned beam with the patient in a standing position on a rotatable platform. Pulsed beam operation correlated to the patient's breathing is preferable for all possible implementations.

The correlation and calibration of the beam delivery system with the imaging of the tumor can be implemented with either fixed or moveable imaging detectors and the use of appropriate phantoms. Antiproton therapy has the added benefit of real-time imaging to confirm correct localization of the therapy within a patient. The possible combinations of imaging techniques include but are not limited to the following: moveable or fixed MRI, CT, PET, or SPECT imaging of the tumor with fixed or moveable PET or SPECT detectors for imaging the delivered dose or fixed or moveable meson detectors for reconstruction of the annihilation vertices.

Antiproton Therapy offers significant advantages when compared to both surgery and traditional radiation therapies in the treatment of certain cancers. Antiproton Therapy offers the targeting advantages of the most technically advanced beam therapies associated with the immense benefits of increased lethality to cancer cells, decreased damaged to healthy, adjacent tissue, and the ability to kill cancerous tumors in 1-2 visits rather than the 30+ treatments required by other radiation treatment 30 regimes.

With regard to antiproton therapy, we have had several insights concerning the therapeutic effects of directing a beam of antiprotons onto a cancerous tumor. Seven of the most important of these insights are as follows:

Insight 1—In the irradiation process, antiprotons will behave very similarly to protons in that they can be targeted in three dimensions to be focused on a tumor, and that they cause very little collateral damage to healthy tissue as they enter a body. Proton beam therapy is a commercially available treatment that is approved by the Food and Drug Administration (FDA) and is reimbursed by Medicare and many health-care plans. It will be possible to retrofit facilities currently used to deliver proton beam therapy to deliver antiprotons to patients.

Insight 2—In the irradiation process, antiprotons will behave very similarly to protons in that as they slow within a tumor, they will release the bulk of their energy in a localized end-of-range ionization zone, followed by a rapid decline in their dose energy. This is known as the "Bragg Peak" phenomenon. The Bragg Peak Phenomenon enables a delivery of a full, localized, and uniform dose of energy to the tumor.

Insight 3—Antiprotons are very different from protons in that, after they slow and all of their kinetic is deposited into the tumor, they will then annihilate in the nucleus (on a neutron or a proton) of the nearest, largest atom, thus depositing an extra, very localized burst of cancer cell-killing energy in addition to what could be delivered by a proton. (See FIG. 14) This energy is in the form of the nucleus of the atom (a heavy ion), upon which the antiproton annihilation occurred, moving through tissue at high speed and destroying cancer cells in a very localized region (~30 microns or approximately the width of a cell). This extra burst of energy allows for the effective destruction of both "resting" cancer cells (i.e. cells that are not currently dividing) as well as "non-resting" cancer cells (cells that are in the process of dividing or replicating). Depending on the type of cancer, replication cycles vary from days to months. A cell is replicating, and therefore is the most vulnerable, only 1-7% of the time. The fact that this "replication cycle" exists, dictates the need for the 25-40 visits extending over many weeks being required for patients who are treated with traditional radiation therapy and chemotherapy. Antiproton Therapy thus eliminates the need for many multiples of doses of radiation therapy. This fact, in turn, means that antiproton therapy will not need the expensive delivery systems and complicated methods designed to ensure reproduceability of a three-dimensional dose profile over a great number of patient visits.

Insight 4—In Antiproton Therapy, the annihilation event creates a heavy ion 5 within the tumor. Heavy ion therapy is a cancer therapy in that is under experimental development in Europe and Japan. Heavy ions cause more damage to a tumor than do protons, but dosing a patient with heavy ions causes significant damage to the healthy tissue between the surface of the body and the tumor. In some cases, heavy ions can cause as much damage to the healthy intervening tissue as do protons to the cancer cells. (See FIG. 15 for a comparison of heavy ion and proton therapies.)

Figure 16:
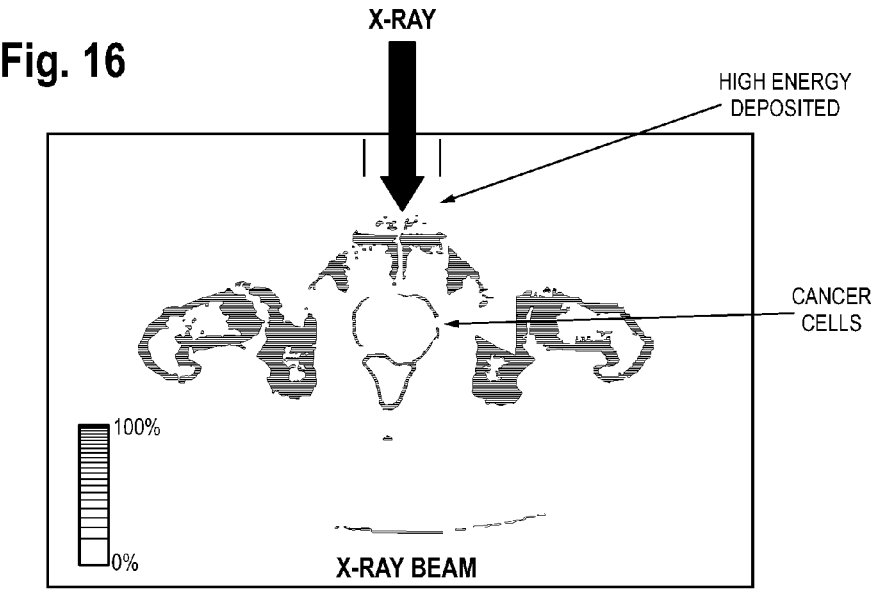

Insight 5—Antiproton therapy creates a heavy ion within a tumor, but it is very different than heavy ion beam therapy in that the surface of the body is not subjected to the high relative dose of heavy ions. Antiprotons thus exhibit the low entrance dose of protons coupled with the high cancer-killing energy transfer of heavy ions. The chart in FIG. 16 shows a comparison of ionization tracks of protons and heavy ions in water (humans are mostly water). Antiproton therapy offers the best of both worlds, having increased lethality to cancer cells with decreased collateral damage to healthy cells, shown in the shaded boxes. In addition, antiproton therapy offers an oncologist the ability to treat radiation-resistant cancer cells.

Insight 6—The particles formed by the annihilation event (pions and gamma rays) are useful species in that they could be used to image the tumor even as the treatment is taking place, using specialized detectors currently used in physics research applications. More attractively, when the antiproton annihilates on a neutron in a carbon, oxygen, or nitrogen atom, that annihilation event will create certain short-lived radioactive isotopes (lie, 150, 13N) within the tumor. These are exactly the same isotopes currently used to image patients with PET techniques. Accordingly, through antiproton therapy, these isotopes can be generated in situ as opposed to being delivered to the patient via injection of radiopharmaceutical compounds as is presently done for PET.

Insight 7—All infrastructure components for the most basic method for delivery of antiproton therapy now exist. Antiproton therapy can be delivered using methodologies very similar to those used for the delivery of proton beam therapy or it can be delivered with a much simplified and cheaper infrastructure. Alternatively, new systems and components may be developed and used for antiproton therapy.

Although several researchers have published articles (primarily in the 1980s) mentioning the feasibility of using antiprotons in the treatment of cancerous tumors, . . . scientists have connected these original feasibility observations with many new insights, including those noted above, to create a unique process for the treatment of cancerous tumors.

Comparative Advantages of the Preferred Method

Cancer is the second leading cause of death of Americans; nearly a million new cases of cancer are diagnosed just in the United States every year. Eighty percent of all cancers are diagnosed in persons aged 55 and older and so as the population of the United States ages, the prevalence of cancer is expected to rise. Current treatments are focused in three areas: surgery, radiation therapies, and chemotherapies. Forty three percent of all cancers can be effectively treated with surgery, eighteen percent of all cancers can be effectively treated with radiation, and three percent of all cancers can be effectively treated with chemotherapy but the success factors are so low for individual treatments that combination treatments are used to treat the majority of cancers.

Antiproton therapy will replace common radiation treatments for many specific cancers and may replace surgery and chemotherapy in specific cases. Antiproton Therapy offers the ability to eliminate a tumor deep within a body without the trauma of surgery, without the collateral damage of many radiation therapies, and without the multiple treatments required by some beam therapies.

1. Advantages Over Surgery

While surgery is used as a primary treatment in many cancers, cancer that can be cured with radical surgery must be in an early stage of development and must be localized. Radical surgery removes additional surrounding uninvolved healthy tissue in order to be able to ensure that the cancerous tissue is completely excised. Surgery for the removal of cancer is invasive and thus causes significant physical trauma to the patient. In addition, surgery must often be coupled with other harsh treatment methodologies, such as chemotherapy or radiation therapy in order to improve the patient's odds of being cured. In these cases, surgery is only the initial step in a regime.

Unlike surgery, antiproton therapy will cause no significant damage to the tissue in between the surface of the patient's skin and the tumor. Unlike surgery, antiproton therapy will be able to target the tumor in three dimensions so the destruction of local, uninvolved tissue will be minimized. Unlike surgery, antiproton therapy is noninvasive; the post-treatment process associated with antiproton therapy will not require the healing of a surgical incision. Infections associated with an incision will be eliminated; there will be no painful healing process.

2. Advantages Over Chemotherapy

Chemotherapy is a common treatment for cancer—both those cancers that are localized and those that have metastasized throughout the body of the patient. Chemotherapy is essentially the controlled whole-body delivery of a substance that is toxic to dividing cells, thus chemotherapy kills both healthy and cancerous replicating cells throughout the body indiscriminately. Normal cells most likely to be affected are the blood cells that are forming in the bone marrow and cells in the mouth, digestive tract, reproductive system, and hair follicles. Chemotherapy drugs can also damage cells of the heart, kidneys, bladder, lungs, and nervous system. A chemotherapy regime is carefully chosen to target certain chemotherapy drugs against those cancer cells that are not resistant to those drugs.

As chemotherapy is typically effective only against replicating cells, it must be delivered to a patient in doses lasting over a period of many weeks. Patients may receive treatments daily, weekly, or monthly, and treatments are usually given in on and-off cycles that allow rest periods so that normal cells can be rebuilt and the patient can regain strength for the next dose of chemotherapy. While the most common short lived side affects are nausea, vomiting, hair loss, and fatigue, there are significant side effects that can last a lifetime, such as potential damage to bone marrow and permanent damage to the heart, lungs, kidneys and reproductive organs. Delayed side effects, such as a second cancer, may show up years later.

Unlike chemotherapy, antiproton therapy is a beam therapy that will be targeted in three dimensions and as such will impact only the cancerous tumor. As a targeted beam therapy, it will not cause damage either to the healthy cells in between the surface of the skin and the tumor or to the healthy cells surrounding the tumor.

Unlike chemotherapy, antiproton therapy is effective against resting cells (those cells that are not actively in the process of dividing). As it is effective against these resting cells in addition to those cells that are actively dividing, doses may be delivered over a period of one or more days rather than weeks or months. Antiproton therapy is effective against the cancer cells that it is targeted against—there will be no resistance to antiproton therapy.

With antiproton therapy, a patient will feel nothing during the treatment. Unlike chemotherapy, after an antiproton therapy treatment, patients will be able to continue their normal activities, with few or no side effects from the treatment. The patient will experience a much better quality of life during and after the antiproton therapy treatment than they will with chemotherapy treatments.

3. Advantages Over Immunotherapy

Immunotherapy has been used as a treatment for cancer in various ways for a number of years but only recently has the concept of immunotherapy treatment been augmented by biotechnology research and development. Theoretically it is the perfect treatment; immunotherapy is aimed at mobilizing the body's own weapons (antibodies) to kill cancer cells. Immunotherapy uses drugs (for example, bacterial vaccines) to stimulate the production of antibodies. However, cancer cells can develop resistance to these antibodies. Recent developments in the biotechnology and genomic fields have been showing some progress in this treatment modality, but except for a very small number of cancer types and cases, immunotherapy is not a typical treatment. Radioimmunotherapy is a variation of immunotherapy where radiation is delivered to the surface of a tumor via the use of monoclonal antibodies (or other molecules) that are tagged with radioactive atoms. Both immunotherapy and radioimmunotherapy typically manage cancer rather than curing it.

Unlike immunotherapy or radioimmunotherapy, antiproton therapy is not limited to those cases where antibodies could potentially be stimulated to attack a cancerous growth. Antiproton therapy can be used against any type of tumor. Unlike immunotherapy or radioimmunotherapy, antiproton therapy treatments can be delivered in days rather than weeks and will be effective against the whole tumor. Antiproton therapy is always effective against the cancer cells that it is targeted against—there will be no resistance to antiproton therapy.

4. Advantages Over Conventional Radiation Therapies

Conventional radiation therapy (x-ray) is a common technique to treat cancer and is used in hospitals all over the world. The surface of a body is exposed to x-rays in order to treat a tumor deep within the body. Radiation therapies generally cost more than chemotherapy, but are effective (i.e., exhibit high response rates) for many types of cancer. However, because radiation is not effective at killing non-replicating cancer cells, a lengthy, sustained schedule of treatments is required in order to target cells during their most vulnerable replicating state. The large doses that often are necessary to treat tumors also cannot be given at one time because of the severe side effects they would cause. On average, the course of treatment for radiation therapy takes 5 to 7 weeks. Typically, radiation oncologists try to avoid exposure of large parts of the body to radiation because this can cause serious side effects like a secondary cancer—one that develops after treatment for the initial cancer.

As with chemotherapy, there are cancer cells that are resistant to radiation, but the most serious shortcoming of X-ray radiation is that it can only be targeted in 2-20 dimensions. The picture in FIG. 16 (from the Lorna Linda University Medical Center web site, http://www.llu.edu/proton/) shows that the highest energy deposition from X-ray radiation is near the surface of the skin, and is not targeted onto the actual tumor cells. X-ray radiation can result in major side effects, including the shutdown or failure of normal body functions. X-ray radiation thus cannot be used near any sensitive organs such as the liver or kidneys.

Unlike conventional x-ray radiation therapy, antiproton therapy is effective against resting cells (those cells that are not actively in the process of dividing). As it is effective against these resting cells in addition to those cells that are actively dividing, doses may be delivered over a period of one or more days rather than weeks or months without the side effects that would be associated with a massive dose of x-ray radiation. Antiproton therapy can be targeted in three dimensions and so will both eliminate dose to healthy tissue and eliminate radiation-associated effects such as a secondary cancer. Antiproton therapy will be able to kill cancerous cells that are x-ray radiation resistant.

5. Advantages Over Proton Beam Therapy

Figure 17:
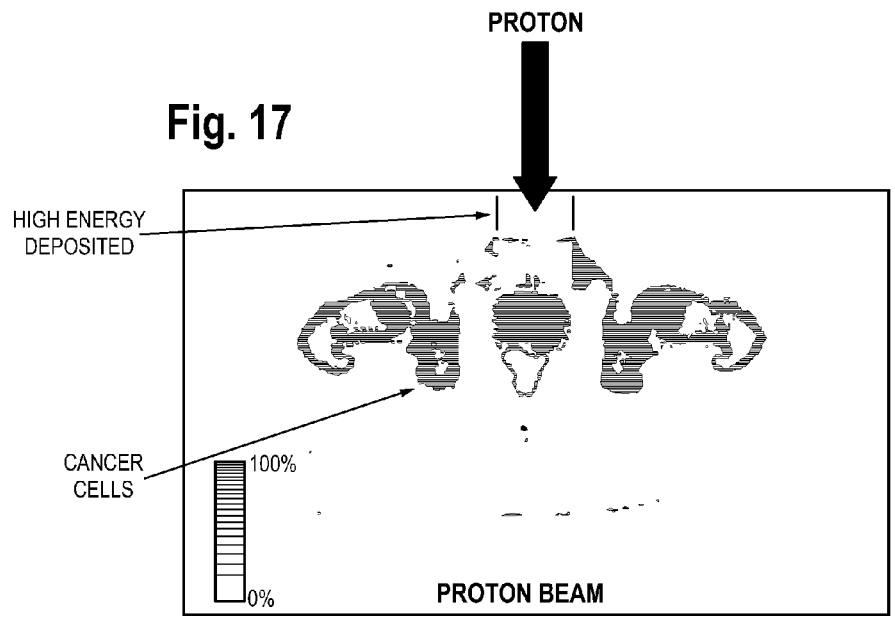
Figure 18:
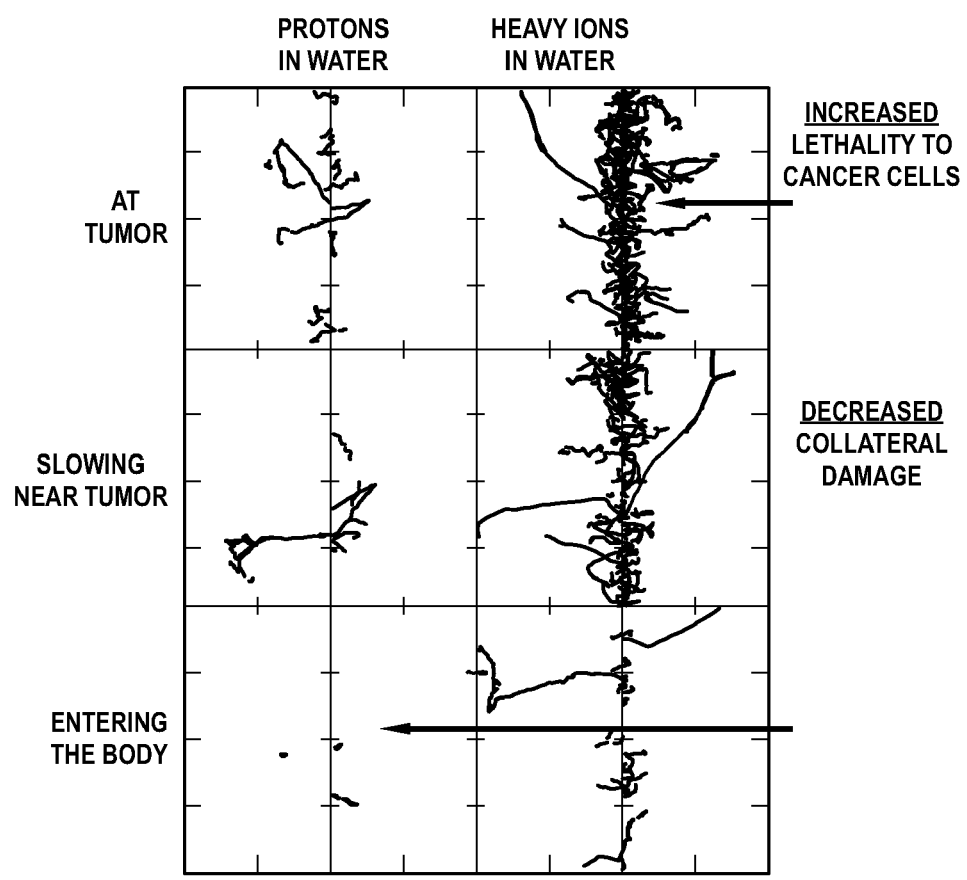

Proton beam therapy solves the problem of treating a tumor in two dimensions—it adds the third dimension by controlling radiation depth. Adjustment of the beam energy controls penetration depth. In proton beam therapy, beams of positively charged particles (protons) are directed at cancerous cells. Protons slow down as they interact with matter. As they slow within the tumor, protons release the bulk of their energy in a localized end-of-range ionization zone, followed by a rapid decline in their dose energy. Virtually no radiation is expended beyond this point. This is known as the Bragg Peak phenomenon (see Insight 2 above), and it enables a delivery of a full, localized, and uniform dose of energy to the tumor. As a consequence, very little radiation is deposited on peripheral tissue and collateral damage is minimized. Side effects are also thus fewer and milder than those experienced with chemotherapy or conventional radiation therapy. The picture in FIG. 17 (from the Lorna Linda University Medical Center web site, http://www.llu.edu/proton/) shows that the highest energy deposition from proton beam therapy is targeted onto the actual tumor cells.

Proton beam therapy is not effective against resting cells and hence requires multiple treatments just as chemotherapy and conventional radiation therapy. A rotating gantry system is used that is designed to emit charged particle beams from different angles to lower the potential of collateral damage from multiple treatments entering the patient at the same location. The patient is fitted with a body cast to insure precise positioning from treatment to treatment. These measures dramatically increase the cost of the therapies.

Like proton beam therapy, antiproton therapy can be targeted in three dimensions and causes minimal damage to peripheral tissue. Unlike proton beam therapy, antiproton therapy is effective against resting cells (those cells that are not actively in the process of dividing). As it is effective against these resting cells in addition to those cells that are actively dividing, antiproton therapy may be delivered over a period of days rather than weeks or months without the need for expensive delivery systems that are designed to deliver designed proton flux to specific locations in a patient over a period of several weeks.

6. Advantages Over Heavy Ion Therapy

Heavy ion therapy is another beam therapy that has been gaining popularity worldwide. In this context, a heavy ion is an atom (e.g., a carbon atom) that has been stripped of its electrons. Like proton beam therapy, heavy ion therapy has the ability to deposit energy directly into the cancerous tumor in three dimensions and like proton beam therapy, heavy ions deposit most of their energy at their end of range (Bragg Peak phenomenon). Heavy ions deposit more energy into a tumor than do protons and hence have more cancer cell killing capability than do protons. Heavy ions do have the capability of killing resting cells, but while the killing power deposited on the tumor for ion therapy is dramatically greater, the collateral damage to healthy intervening tissue (that tissue between the skin surface and the tumor) is likewise greater—even greater collateral damage than for conventional radiation. The collateral damage for ion therapy can be even greater than the direct damage to the tumor with proton therapy. (see FIG. 15).

Like heavy ion therapy, antiproton therapy can be targeted in a three dimensional fashion directly onto a tumor, and like heavy ion therapy, antiproton therapy has the ability to kill resting cancer cells via a heavy ion mechanism. Unlike heavy ion therapy though, where the patient endures a direct dose of heavy ions to all tissue in between the surface of their skin and the tumor, the heavy ion in antiproton therapy is created within the tumor. Thus in antiproton therapy, the antiprotons enter the body depositing the low energies associated with single-charged, lightweight protons. At the tumor site, through the annihilation event, those antiprotons transform some of the atoms of the tumor into heavy, multiply-charged ions that are capable of killing resting cells in a very localized fashion.

7. Other Advantages of Antiproton Therapy

Pion Detection: Antiproton therapy has an additional advantage offered by the annihilation event. As an antiproton annihilates on a proton or a neutron of an atom within a tumor, other energetic particles are created in addition to the heavy ion. In particular, gamma rays and pions are emitted by this event. The direction and energy of the pions that exit a patient's body can be measured using a high-energy particle detector. In this way, the direction and the origin of the pions can be used to image where the annihilation event took place within the patient and can be used to determine the dose delivered to the tumor.

In Situ creation of PET Isotopes: PET is used to perform early detection of cancer, to monitor brain activity in Alzheimer's patients, and to and measure blood flow in heart disease cases. The particular short-lived radioactive isotopes used in PET ($^{11}C$, $^{15}O$, $^{13}N$) are currently delivered to patients via injection of radiopharmaceutical compounds. The procedure is FDA-approved and is widely accepted. In the employment of antiproton therapy, the annihilation event will create PET isotopes within the cancerous tumor, allowing for the real-time imaging of that tumor even as treatment is taking place.

Disclosed are methods relating to the field of the treatment of cancer and other diseases by using radiation. Specifically, it addresses the use of antiprotons to deliver the ionizing radiation and heavy particles to cancerous tissues, as well as the advantages of using antiprotons rather than x-rays, gamma rays, electrons, protons, heavy ions, mesons, or any other particles, as well as methods of delivering the radiation to the desired region of the body. In preferred embodiments, the incident antiprotons are used to destroy the cancerous cells and also to generate, in situ, PET isotopes, gamma rays and pi mesons which may be used to create real-time images the treatment site during treatment.

Ser. No. 60/382,042; Titled: Method for Investigating Use of Antiproton Beams in Clinical Radiotherapy; Filed: May 2, 2002

This invention relates to the field of the treatment of cancer and other diseases by using radiation. Specifically, it addresses methods of investigating the use of antiprotons in clinical radiotherapy.

Radiation has been used to treat cancer and other diseases for many years. In general, radiation is used to kill cancer cells immediately or to damage cancer cells enough to prevent reproduction. The fundamental problems with all forms of conventional radiation therapy are the delivery of an adequate dose (micro-density of ionization) to the desired cells (localization) at the right time without damaging healthy surrounding tissue.

With conventional radiation therapies, delivery of a dose of radiation adequate to damage cancer cells within a tumor is balanced against the amount of collateral damage that that particular dose of radiation will cause to healthy tissue. The specific nature of the radiation determines what collateral damage is done to healthy tissue and also determines the number of treatments required to deliver a dose calculated to be sufficient to treat a tumor. Treatment planning typically involves detailed computer modeling for all incident forms of radiation. These exact calculational schemes are specific to a particular patient and treatment facility, but the mathematical principles underlying the calculations are generally applicable.

Localization, the deposition of ionizing radiation within the desired region of the body, is performed internally or externally. Radiation therapy performed internally can be administered by radiation implant or via radioimmunotherapy. The general term, brachytherapy, refers to the insertion of an implant containing radioactive material directly in the tumor. It requires both the invasive surgical insertion and surgical removal of the radioactive implant. It is limited in its ability to treat large tumors uniformly. Radioimmunotherapy is a radiation therapy that involves delivering radiation to the surface of a tumor via the use of monoclonal antibodies that are tagged with radioactive atoms. It is also limited in its ability to treat large tumors.

Radiation therapy performed externally uses different methods of localization depending on the nature of the radiation. Simple collimation using appropriate shielding is used to localize the radiation field in two dimensions. Controlling the depth distribution of the energy deposition depends on the specific nature of the radiation; whether it is electromagnetic, charged particle, or neutral particle. Again, the specific nature of the radiation also determines how well defined the localization can be and how much damage is done to adjacent and intervening healthy tissue.

When the incident radiation is electromagnetic (e.g., x-rays), more ionizing radiation is produced near the surface than deeper within the body. Electromagnetic radiation, as opposed to charged particle radiation, always delivers some ionizing radiation at all depths in the body. Thus, localizing the depth distribution of ionizing radiation is inherently more difficult with electromagnetic radiation than with charged particle radiation. Complex methods for the enhancement of the three dimensional localization of ionization within the body are well developed. These methods involving the overlapping of intersecting radiation fields are known by such names as gamma knife, intensity modulated radiation therapy (IMRT), and dose sparing methods. All these techniques minimize the dose to healthy tissue by spreading out the entering dose over a large volume, but all of these techniques still lack a true capability for three-dimensional delivery.

When the incident radiation is in the form of high-energy charged particles, more energy is deposited at the end of range, that is, more energy is deposited just before the particle stops than when it enters the body. This is the Bragg peak effect and is the basis for localization in depth. The distance the charged particles travel in the body is approximately the same for all similar charged particles of the same energy. Higher energy particles travel further in the body than lower energy particles. Well-developed techniques exist for delivering different energy protons (positively charged particles) to various locations in the body using a fixed or variable energy accelerator, beam transport systems, variable thickness degraders, scanning systems, patient positioning, and methods for correlating ionizing energy deposition with various methods of imaging the internal structures of the body. The choice of ionizing particle determines the density of ionization (dose to the tumor) versus position along the path of the particle.

Neutral particle therapy (neutron therapy) achieves localization with overlapping fields and/or the use of pharmaceuticals containing an isotope that captures the neutron and subsequently decays into ionizing particles. This combined method known as boron neutron capture therapy (BNCT) requires the development of special boron containing pharmaceuticals preferentially absorbed by the cancerous tumor.

A second problem with all forms of radiation therapy is delivering the correct density of ionizing radiation to the individual cells to either destroy the cells immediately or damage them enough to induce programmed cell death. On the microscopic scale, there are significant differences in the density of ionization and the nature of the damage produced by the various forms of radiation. These differences are accounted for by the concepts of the radiation adsorbed dose (Rad) and the relative biological effect (RBE). Radiation oncologists use these known concepts to plan the treatments using photons, neutrons, protons, heavy ions, or other charged particles. A significant improvement over the state-of-the-art would be the ability to change the density of ionization depending on the location (low density in healthy tissue and high density in diseased tissue).

Another problem with all forms of radiation therapy is the timing of the radiation treatments. Because the cells have repair mechanisms, they are able to recover from sublethal doses of radiation. Cells have variable sensitivity to radiation depending on whether they are actively reproducing or are in the resting state. Radiation oncologists typically administer many sub-lethal doses of radiation delivered over several weeks to destroy all the diseased cells when they are most vulnerable to radiation and to allow the healthy cells to recover between irradiations. This fractionation of the treatment is a significant inconvenience to the patient and is a major cost factor. A significant improvement over the state-of-the-art would be the ability to deliver a single dose of radiation to a tumor that is capable of destroying resting cells (cells that are not in the process of dividing) as well as those which are actively dividing.

Detailed Description of the Preferred Embodiment

We have begun an investigation into the potential use of antiproton beams in clinical radiotherapy. Observed experimentally for the first time in 1955, antiprotons are the antimatter counterpart to protons, with a negative charge and parity and rest mass of 938 MeV/c2. Antiprotons have depth dose characteristics similar to protons in that they exhibit an energy dependent Bragg peak. The matter-antimatter annihilation event at the end of range is accompanied by the release of nearly 2 GeV, primarily in the form of energetic pimesons, but also neutrons, K-mesons and gammas, and of particular interest for therapeutic applications, charged nuclear fragments. Characteristics of antiprotons and methods for using antiprotons for treatment of cancer and. other diseases are discussed in more detail in Applicant's U.S. Provisional Application No. 60/316,711, filed on Aug. 30, 2001, entitled NON-INVASIVE METHOD OF CELLULAR TERMINATION USING ANTIPROTON REACTIONS, the entire disclosure of which is hereby incorporated by reference and made apart of this specification.

We are using the Extension of Monte Carlo N-Particle (MCNPX) code developed at Los Alamos National laboratory to evaluate the feasibility of clinical antiproton therapy and in the design of physical experiments. MCNPX combines the traditional Monte Carlo NParticle (MCNP) particles (neutrons, photons, and electrons) with the high-energy, multiparticle transport features of the Los Alamos High Energy Transport (LAHET) code package. The intermediate energy model in MCNPX simulates antiproton annihilation and accompanying secondary particle production. The de-excitation of the residual nucleus after proton-antiproton annihilation is modeled using the multistage pre-equilibrium model and multifragmentation of light nuclei is based upon the Fenni-Breakup model.

Monte Carlo calculations confirm that the annihilation event produces a significantly larger Bragg peak relative to a proton dose deposition curve. For 150 MeV incident antiprotons; the peak-to-plateau ratio is approximately twice that for protons of a similar energy. The antiproton peak-to-plateau advantage over protons increases as the incident energy is decreased. Perhaps more significantly, a further potential clinical advantage exists in the form of the high relative biological effectiveness (RBE) of the charged nuclear fragments produced in-situ at the end of range.

While gammas resulting from the prompt neutral pion decay have sufficient energy to exit a human, roughly half of the charged pions produced will contribute to a relatively isotropic background dose. Nevertheless, this background is inconsequential relative to the clear physical and biological advantages.

Ser. No. 60/388,428; Titled: Real Time Detection of Delivery of Antiprotons for Therapeutic Uses; Filed: May 29, 2002

This invention relates generally to the field of treating cancer, diseases, or any other conditions by the use of antiprotons and, more specifically, to an ability to detect, through measurement of energy and/or position of nuclear particles generated as a result of the treatment process, both the location of radiation delivered and the dose of radiation delivered, in real time.

Radiation Therapy

Radiation has been used to treat cancer and other diseases for many years. In general, radiation is used to kill cancer cells immediately or to damage cancer cells enough to prevent reproduction. The fundamental problems with all forms of conventional radiation therapy are the delivery of an adequate dose (micro-density of ionization) to the desired cells (localization) at the right time without damaging healthy surrounding tissue. There are two separate concerns that the radiation therapy industry has been trying to solve to optimize conditions for safe delivery of radiation therapy: 1) ensuring proper location of the energy deposition in real time; 2) ensuring proper amount (dosimetry) of radiation at each location in real time.

Radiotherapy or radiation therapy is the use of penetrating beams of high-energy x-rays or gamma rays or streams of particles to treat various diseases such as cancer. The goal of a radiotherapy treatment protocol is to use radiation kill abnormal or unwanted cells with as little damage as possible to the normal surrounding cells. In conventional radiotherapy treatments, medical equipment is used to deliver high energy radiation to tumorous tissue (or other tissue to be irradiated). The placement of the radiation must be accurately controlled to ensure that the tissue to be treated receives sufficient radiation (dose) to be destroyed and the damage to the surrounding and adjacent non-diseased tissue is minimized. Currently, patient absorption of radiation is simulated and modeled before a patient is treated.

The simulation and modeling for external radiation delivery typically relies on computational methods to attempt to ensure localization of radiation delivery for all incident forms of radiation. The exact computational schemes are specific to a particular patient, to a particular type of radiation, and to a particular treatment facility. They are based on physical patient data, known radiation penetration data, and the intensity of the radiation to be delivered to a particular point in a patient. The correct density of ionizing radiation must be delivered to the individual cells to either destroy them immediately or to damage them enough to induce programmed cell death. On the microscopic scale, there are significant differences in the density of ionization and the nature of the damage produced by the various forms of radiation. These differences are accounted for by the concepts of the radiation adsorbed dose (Rad) and the relative biological effect (RBE). Radiation oncologists use these known concepts to plan the treatments using photons, neutrons, protons, heavy ions, or other charged particles.

After the treatment is planned, additional simulations with a patient are typically conducted. These could involve special x-ray or Computer Aided Tomography images as well as the construction of immobilization devices that permit some uniformity of patient positioning throughout a course of treatments. Computers are used to calculate the planned locale and dose distribution of the radiation. Location is presumed by delivery of a beam of radiation to marked skin and dosimetry is presumed by calibration of the instrument that delivers radiation to a patient. Medical practitioners cannot independently verify accuracy of "either variable in real time (i.e. during a particular radiotherapy session).

Typically treatment regimes last between two and five weeks. This fractionation of radiation delivery allows for intervening irradiated tissue to recover and also provides some assurance that the area planned to be irradiated receives some measure of radiation over the many treatment sessions. During the course of treatment, new images of the area irradiated are required (such as x-ray port films). These are used to ascertain the correctness of the location delivery model for the treatment plan, but do not provide either location or dose delivery information on a real-time basis.

Techniques exist for delivering certain types of charged particles to specific locations in the body using a fixed or variable energy accelerator, beam transport systems, variable thickness degraders, scanning systems, patient positioning, and methods for correlating ionizing energy deposition with various methods of imaging the internal structures of the body. In many cases, the use of collimation equipment or the use of techniques involving the overlapping of intersecting radiation fields are required. There is a complete reliance on patient models to calculate the location of where the radiation should be delivered. None of these techniques allow for a health care professional to actually measure or detect in real time where radiation is being delivered within a patient. These techniques do not allow for the detection of dose delivered in real time.

Other external radiation techniques such as neutral particle therapy (neutron therapy) attempt to attain localization with overlapping fields or the use of pharmaceuticals containing an isotope that captures the neutron and subsequently decays into ionizing particles. This combined method known as boron neutron capture therapy (BNCT) requires the development of special boron containing pharmaceuticals preferentially absorbed by the cancerous tumor. Again this technique also does not allow for a health care professional to actually measure or detect in real time where radiation is being delivered within a patient and does not provide any information regarding the actual dose delivered.

Localization, the deposition of ionizing radiation within the desired region of the body, can also be performed internally. Radiation therapy performed internally is administered by a radiation implant. The general term brachytherapy refers to the insertion of an implant containing radioactive material directly into the area to be treated. Use of this technique has the advantage of allowing a health care professional to know exactly where and how much radiation is being delivered, but requires both the invasive surgical insertion and surgical removal of the radioactive implant. Real time detection of the placement of the brachytherapy unit can carried out using fluoroscopic detection techniques.

A significant improvement over the state-of-the-art would be the ability to change the density of ionization (the dose delivered) depending on the location (low density in healthy tissue and high density in diseased tissue). This would require the ability to detect, in real time, both the location and the intensity of the radiation delivered at that particular time to a patient. Currently, there are no techniques that allow for the real time detection of dose delivered to a particular point within a patient.

The use of antiprotons for radiation therapy would, as a result of the antiproton annihilation event at a targeted site, generate characteristic particles at that target site. These characteristic particles would then be used to conduct real-time measurement of both the position and dose of radiation delivered to a target within a body. This would ensure both proper location of the energy deposition in real time and proper amount (dose) of radiation at each location in real time.

Positron Emission Tomography

In Positron Emission Tomography (PET), images of metabolic, biochemical, and functional activities in living tissue are produced. A patient is injected with a radiopharmaceutical (a pharmacologically active agent that is tagged with a positron emitting isotope such as $^{11}C$, $^{15}O$, and $^{13}N$) and the area of interest is then imaged with a special device that measures the gamma radiation from the radioactive decay of that isotope. As the radiopharmaceutical travels throughout a patient, the computers and series of gamma detectors that constitute a PET camera are programmed to differentiate between the background radiation created by the general dispersal of the radiopharmaceutical in a body and the radiation from the area targeted by the pharmacologically active carrier. Three-dimensional images are created by the programmed movement of the patient and the detector array.

Positron Emission Tomography (PET) is used to perform early detection of cancer, to monitor brain activity in Alzheimer's patients, and to and measure blood flow in heart disease cases. The procedure is Food and Drug Administration-approved for many applications and is widely accepted.

A limitation to PET is the requirement for the use of relatively short-lived radioisotopes. Facilities that offer PET imaging must be located near a particle accelerator that produces the radioisotopes or must be able to use those radioisotopes that can be shipped. There is a patent (U.S. Pat. No. 5,977,554) that claims a system to generate biomedically useful radioisotopes using antiprotons. The concept is also reviewed in the paper "Antiproton Portable Traps and Medical Applications" (R. A. Lewis, G. A. Smith, and S. D. Howe Hyperfine Interactions 109 (1997) 155-164). These biomedically useful radioisotopes would always be generated outside of the body of a patient and administered by injection for ultimate use in standard three-dimensional PET imaging.

The concept discussed in this document of using PET isotopes generated by an antiproton annihilation event to carry out an in situ imaging process is a completely different. In the employment of antiproton therapy, when the antiproton annihilates on a neutron in a carbon, oxygen, or nitrogen atom, that annihilation event will create certain short-lived radioactive isotopes ($^{11}C$, $^{15}O$, $^{13}N$) within a patient's body at the point of the annihilation event. While these are exactly the same isotopes currently used to image patients with Positron Emission Tomography (PET) techniques, they are currently delivered to the patient via injection of radiopharmaceutical compounds. There is no technique known that can create PET isotopes within a patient.

This creation and subsequent detection of the PET isotopes created as a result of the antiproton annihilation event will allow for real-time detection of the location of the antiproton beam delivery even as treatment is taking place. This will ensure proper location of beam delivery in real time and will help limit injury to normal, untargeted tissue by allowing medical practitioners the ability to change the dose of radiation delivered to a specific location even as a treatment is taking place.

Positionality and Dosimetry

The desire of medical practitioners to verify beam delivery is demonstrated by the complexity of some of the methods used to confirm beam localization. Jose R. Alonso of Lawrence Berkeley National Laboratory reviewed in two papers ("Review of Ion Beam Therapy", Invited paper, presented at the 7th European Particle Accelerator Conference, "Austria Center, Vienna, Austria, Jun. 26-30, 2000, and "Medical Applications of Nuclear Physics and Heavy-Ion Beams" Invited paper, presented at the 7th International Conference on Nucleus-Nucleus collisions, Palais de la Musique et des Congres, Strasbourg, France, Jul. 3-7, 2002) the use of radioactive beams for treatment verification that was pioneered at the Bevalac at Berkeley, Calif.. At the Bevalac, external beams of $^{19}Ne^+$ (a positron emitter and potential PET isotope) have been produced and used to verify accuracy of treatment plans. At the Heavy Ion Medical Accelerator in Chiba Japan (RIMAC), researchers are using an external beam of $^{11}C^+$ (another positron emitter and a PET isotope) to treat patients. Intensities at the HIMAC are sufficient for both PET imaging and treatment.

At the Gesellschaft fur Schwerionerforschung mbH (GSI) in Darmstadt, Germany, PET imaging with $^{11}C$ has been fully integrated into their treatment protocols. The $^{11}C$ has essentially the same range as the $^{12}C$ used as the primary beam for the heavy ion beam treatment so that imaging the positron annihilation radiation from the $^{11}C$ gives a direct measure of the stopping point of the beam. This allows for verification that the beam has actually reached the planned treatment volume. At GSI, treatment plans are modified based on measurements conducted during early treatment delivery to ensure accurate overall treatments.

In both of these cases, the positron-emitting species is administered to a patient by means of impinging the beam of that particular radioisotope onto a patient. The positron-emitting radioisotope can be used as the external treatment beam (as at HIMAC) or as a calibration to an external heavy ion beam (as at GSI). Antiprotons have also been proposed as simulators for the delivery of charged particle beams. This external application was proposed by Kalogeropoulos and Muratore in their publication "Antiprotons for Imaging and Therapy" (*Nuclear Instruments and Methods in Physics Research* B40/41 (1989) 13221325)). This particular technique however, would require much more than the "few" antiprotons said to be needed by Kalogeropoulos.

Antiprotons have been proposed for therapy-independent imaging applications. Antiprotonic Stereography was proposed by Gray and Kalogeropoulos (*IEEE Transactions on Nuclear Science*, NS-29; 1051; 1982). This technique was reviewed by Kalogeropolous, et al in other publications (*Nuclear Instruments and Methods in Physics Research* B40/41 (1989) 1322-1325). Kalogeropoulos and Muratore proposed administering antiprotons to a tumor to obtain an image after which the tumor could be treated ("Antiprotons for Imaging and Therapy" *Nuclear Instruments and Methods in Physics Research* B40/41; 1989, 13221325).

The use of charged pions for the diagnosis of tumor development was proposed by R. A. Lewis, G. A. Smith and S. D. Howe in their publications "Antiproton Portable Traps and Medical Applications" (*Hyperfine Interactions* 109 (1997) 155-164).

With regard to the employment antiprotonic annihilation products to detect the endpoint of an antiproton beam used in treatment, Gray and Kalogeropoulos proposed simultaneous treatment and viewing via the use of energetic charged mesons in their paper "Possible Biomedical Applications of Antiproton Beams: Focused Radiation Transfer." *Radiation Research* 97, 246-252 (1984)). Again, this particular technique would require many more than the "few hundred" antiprotons said to be needed by Kalogeropoulos.

Kalogeropoulos, et al proposed use of the same charged pions in their paper "Biomedical Potential of Antiprotons" (RAND Workshop on Antimatter Science and Technology, eds. B W Augenstein, World Scientific Singapore, Oct. 6-9, 1987 p. 640). They mentioned that energetic gammas produced from neutral pions are in principle more accurate but that measurement errors for charged particles are smaller.

The present invention covers methods and systems for generating positron-emitting or other radioisotopes in a body through the administration of antiprotons to a target site. The proper administration of antiprotons to a target site results in a series of complex annihilation events in which characteristic particles are generated and released. The present invention uses certain characteristic particles, such as neutral pions, emitted by antiproton annihilation to conduct real-time measurement of both the position and dose of radiation delivered to a target within a body. This application incorporates by reference U.S. provisional patent application 60/316,711 "Noninvasive Method of Cellular Termination using Antiproton Reactions".

Determination of the point of annihilation in real time will allow for an immediate feedback of beam positioning throughout a patient's treatment regime, that can be used to improve, for example, beam targeting in an area of interest. Determination of the number of annihilations in real time will allow for immediate feedback on the dose delivered to a particular target at any point in time. Comparison of the beam endpoint position with any imaging data taken prior to an antiproton treatment regime will provide verification of the extent of the area treated and information for future treatment planning, including additional areas that need to be treated (targeting), and calculations of duration of treatment and number of antiprotons to be delivered (dosage).

The localization of the energy deposition within the body when using antiprotons places strict requirements on the accuracy of positioning the beam and the locating the region of annihilation. This patent directly addresses the methods of implementing position sensitive detectors, tomographic reconstruction, two dimensional and three dimensional image reconstruction, vertex reconstruction, and multiple overlapping imaging techniques for visualization of antiproton irradiation procedures in approximate real time. The information generated can be used for confirmation of planned location and dose of radiation during and immediately after application of said radiation.

In principle, each incident antiproton will produce one or more possible events that can be used to determine the location in physical space of the annihilation of the antiproton. In this description, an event consists of several pieces of information that are correlated in time and can be combined to determine the location of the annihilation of the incident antiproton. In the preferred embodiment of this patent, the event may consist of, but not be limited to one of the following: (1) known incident energy, direction, and position of the antiproton; pion production at the time of annihilation; measurement of the position and direction of one or more of the pions and or other decay products; (2) annihilation of an antiproton on a stable nucleus in the body resulting in creation of a PET (positron emission tomography) isotope; decay of the nucleus (including but not necessarily limited to $^{11}$C, $^{13}$N, or $^{15}$O) by emission of a positron; annihilation of the positron on an electron in the vicinity (~1-2 mm.) of the antiproton annihilation; detection of the positron annihilation by coincident back-to-back 511 keV gamma rays. In the case of event (1) above, the location of the annihilation would be determined by vertex reconstruction. In the case of event (2) above, normal tomographic image reconstruction would be implemented. Other possible implementations may include such technologies as, but not necessarily limited to, SPECT (single photon emission computed tomography) or combinations of the above.

The correlation of the reconstructed image with the predetermined position for deposition of energy with antiprotons is also part of the preferred embodiment of the patent. The initial determination of the region to be irradiated can be made by one or more of several imaging technologies such as PET, MRI (magnetic resonance imaging), CAT (computer assisted tomography), or multiple x-ray projection. The first three methods mentioned above lend themselves to two and three dimensional reconstruction methods and virtual reality presentations. The overlap of such three dimensional images with the antiproton annihilation generated images described above can be accomplished in one or more ways such as immobilization in a reference cast and patient transfer, sequential imaging at the time of treatment with moveable detectors, or simultaneous imaging with multiple purpose detectors. Certification and calibration of the images and the overlap and correlation between images can be implemented with the use of known phantoms.

The preferred method of administering radiation with antiprotons consists of planning a particular treatment protocol based on the measured positions to be irradiated, the assumed compositions of the intervening materials, the distances to be traversed, and Monte Carlo simulations of the energy loss of the antiprotons on entering the body. The result of these calculations is a prediction of the three dimensional distribution of the end of range of the administered antiprotons. This preliminary simulation is a model calculation enabling an optimized treatment protocol to be planned. The important point to remember is that this treatment plan is only a best estimate. The result of this calculation is no better than the assumptions on which it is based. There are many possible errors that can produce an incorrect prediction. Among the most important are incorrect assumed composition, incorrect assumed density, and incorrect knowledge of the stopping power of the incident antiprotons as a function of composition and energy. This patent specifically provides a method for correcting the accumulated errors in the model treatment plan at the time the radiation is delivered.

A possible implementation of the method is to deposit a known, small amount of antiproton radiation at one or more fixed positions within the tumor. The locations of the fixed antiproton deposits would be determined by either the vertex reconstruction mentioned above and or positron emission tomography as previously described. These antiproton-generated fiducials produced within the tumor by the beam are then compared to the initial model dependent treatment plan calculations. Any differences between the calculated and measured positions would be used immediately to correct the total errors in the model. This updated treatment plan would then be used or the process could be iterated until convergence to the desired accuracy is achieved. The ability to create the model, calculate the dose to be delivered, measure the delivered dose, modify of the model, and iterate the process to the desired degree of accuracy spans many different professions.

This process of detection of various characteristic particles generated as a result of the antiproton annihilation process will provide, in the course of therapy, simultaneous verification of both the location and dose of radiation delivered by antiprotons and thus will allow for modification and optimization of a treatment even as it is taking place. A medical practitioner can therefore choose whether to measure location, or dose, or both simultaneously.

Real-Time Beam Delivery Detection: Confirmation of Planned Location of Beam Delivery The specific mechanism by which antiproton therapy would destroy any targeted tissue will also enable the detection of the location of the delivered antiproton in real time i.e. during the treatment of a patient. In the irradiation process, as antiprotons slow within the targeted tissue, they release the bulk of their kinetic energy in a localized end-of-range ionization zone. After they slow and all of their kinetic energy is deposited, they then annihilate in the nucleus (on a neutron or a proton) of the nearest, largest atom, thus depositing an extra, very localized burst of energy. When an antiproton annihilates at rest on a proton it produces a number of energetic pions, charged particles, and gamma rays. These pions, particles and gamma rays all move away radially from the annihilation site. It is possible to track these species, which all point back to a common point, to the vertex of the annihilation event. Locating the vertex allows for the removal of certain types of backgrounds and the reconstruction of the physics of the event, thereby allowing for the visualization of a distributed source of annihilation radiation.

Another attractive option is to use the particles generated from decay of any radioisotopes generated in-situ as a result of the antiproton annihilation event. For example, when the antiproton annihilates on a neutron in a carbon, oxygen, or nitrogen atom in a body, that annihilation event will create certain short-lived radioactive isotopes (e.g. $^{11}C$, $^{15}O$, $^{13}N$) at the point of annihilation. These particular isotopes are the same isotopes currently used to image patients with Positron Emission Tomography (PET) techniques. In the current usage of PET imaging, these isotopes are delivered to a patient via injection of a radiopharmaceutical compound and infiltration of that compound to a specific site within a body where they are used to image functionality of a particular organ or site. When they are generated in-situ by the impingement of antiprotons, they do not provide information on organ functionality, but they can be used to pinpoint the location of delivered antiprotons within a patient. This would allow for real time determination that the radiation delivered is on-target within a patient, using familiar techniques and equipment equivalent to those currently being used for PET, but in a different modality.

Real-Time Dosimetry: Confinnation of Planned Dosage Delivery

Dosimetry is the measurement of the number of antiprotons delivered in each location of the body and is an important part of any treatment protocol. The annihilation of an antiproton in living tissue creates a heavy ion that destroys that living tissue (cancerous tissue or any other targeted tissue) in a one or two cell radius. The annihilation event simultaneously produces several high-energy particles—pions and gamma rays—that enable the detection of the antiproton delivery in real time—i.e. during the treatment of a patient. The pions and prompt gamma rays can also be used to provide concurrent information on the dose of radiation being delivered, even as the treatment is taking place.

There are at least three possible ways to perform dosimetry: 1) count the number of incident particles by well known detection methods or integrate the incident charge; 2) measure the prompt radiation associated with the annihilation of the antiprotons; 3) measure the delayed activity induced by irradiation with antiprotons. The first two methods have the advantage of real time measurement for active control of the beam. The third method is based on positron activity and has the advantage of measuring the spatial uniformity and extent of the delivered dose in the body. When combined with the other imaging methods used for treatment planning, this third method is useful for confirming the actual received dose.

For methods 1 and 2, the number of gamma rays and pions that are detected outside of the body is directly proportional to the number of antiproton annihilations that have occurred inside the target volume and, therefore, the number is also directly proportional to the physical dose of radiation that has been delivered to the target volume. Accurate dosimetry requires coupling the image of the irradiated volume with the number of external particles that are detected, as dose is defined as the amount of energy delivered per unit mass of target irradiated. Given a knowledge of both the irradiated volume and the total number of annihilations that have occurred within the volume, one could determine the dose delivered to a patient as a treatment is taking place.

For method 3, the dose delivered could be measured by measuring the radioactive decay of any radioisotopes generated in-situ as a result of the antiproton annihilation event. Again, when the antiproton annihilates on a neutron in a carbon, oxygen, or nitrogen atom in a body, that annihilation event will create certain short-lived radioactive isotopes (e.g. $^{11}C$, $^{15}O$, $^{13}N$) at the point of annihilation. These particular isotopes are the same isotopes currently used to image patients with Positron Emission Tomography (PET) techniques. When they are generated in-situ by the impingement of antiprotons, they do not provide information on organ functionality, but they can be used to calculate the dose of delivered antiprotons within a patient. This would allow for a determination that the correct dose of antiproton therapy is being delivered to a patient during treatment, using the familiar techniques and equipment equivalent to that currently being used for PET. Again, the data obtained from the PET instruments would be used in a different fashion than is known in the field today, and computational capabilities would have to be added in order to be able to compensate for the timing of the radioactive decay from the isotopes generated.

A preferred embodiment of the idea consists of a beam delivery system compatible with a high efficiency, high spatial resolution detector system in close proximity to the patient. The beam delivery system consists of either a fixed beam and moveable patient or a fixed patient and a moveable beam or a combination of the two. The moveable beam is implemented with magnetic and or electrostatic steering, techniques that are well understood.

In current radiation therapy techniques, the desired dose to be dispensed to a patient is calculated before delivery of the radiation. Simulations and calculations are done based on physical examinations, laboratory tests, and imaging studies. Information from the simulations and calculations is used to determine how much radiation is needed, how it is to be delivered, and the number of treatments required. Researchers are now testing various Monte Carlo simulations to clinically improve the accuracy of radiotherapy dose calculations. Dose distributions in experimental phantoms and in test patients are used to verify optimized treatment plans based on these Monte Carlo calculations.

The current radiation techniques thus treat a patient to deliver radiation as predicted by a model, but the model may not accurately portray the patient. Real time verification of radiation delivery (location and dose) will be able to validate a treatment plan even as a patient is being treated. Updates can take place during the delivery of therapeutic radiation.

Radiation overexposures are not unknown using current radiation therapy techniques. Overexposures of radiation therapy patients in Panama were attributed to lack of treatment plan verification and to the method of entering beam block data into radiation treatment planning software. Use of a radiation therapy procedure that provides real-time imaging and dose feedback would not allow these radiation overexposures.

The importance of a post-treatment verification system for dose and placement of radiation therapy is described in U.S. Pat. No. 5,394,542 "Verification System for Radiation Therapy". This patent provides for "a verification system that can be used in conjunction with a radiation intensity compensator to minimize the possibility of an uncontrolled beam ray irradiating nontumorous tissue. In one embodiment, the verification system may collect tomographic data on absorbed radiation within the patient and generate tomographic absorption images therefrom. These images may be used for radiation dose verification as well as for planning subsequent therapy sessions." Again, this technique is a post-radiation technique that does not provide real-time feedback on location or dose.

A substantial advantage of the PET image created using antiprotons as described above is that the signal-to-noise characteristic of the resulting image is much improved over standard Positron Emission Tomography images. This is due to the fact that essentially no background signal is produced using antiprotons to create the radioisotopes at the end-of range positions, whereas a large background signal is produced in standard PET imaging due to incomplete selectivity of the infiltration process of diffusing the radioisotopes to the targeted regions of the body. Radioisotopes that don't migrate to the targeted regions will emit radiation that tends to obscure the desired PET image by creating an undesirable background of emitted intensity of radiation. The image created from the annihilation of antiprotons contains no such background as the radioisotopes that are created by antiproton annihilations are created only at the end-of-range positions within the target. The signal-to noise improvement using antiproton annihilations to create the positron-emitting radioisotopes would be perfect except that occasionally a few antiprotons of the incident beam of antiprotons will annihilate prematurely before reaching the targeted volume, due to direct nuclear collisions of the incident antiprotons with nuclei of intervening tissue in the body. The premature annihilation events are relatively rare and result in a low-intensity signal that illuminates the track of the incident path in the final PET image.

Another inventive aspect of the present invention is the use of the low-background characteristic of antiproton-produced radioisotopes coupled with the short half lives of the radioisotopes to image flow and/or diffusion characteristics within vessels or through tissue. Antiproton annihilations in blood or other fluids create short-lived radioisotopes within the blood or fluids. The most common radioisotopes that will be produced in human fluids are $^{11}$C, $^{15}$O, $^{13}$N, as these atoms are the most common atoms found in the body. These radioisotopes have half lives of 20, 10, and 2 minutes, respectively. Circulatory blockages or hemorrhages could be readily imaged using standard PET imaging equipment to follow the diffusion of small volumes of blood or fluid that is initially irradiated with a low-intensity, highly localized pulse of antiprotons. A low-intensity pulse of antiprotons creates a small volume of radioisotopes that will flow with the blood or fluid in the local region. The path of the flow is readily imaged from the emitted radiation because the background intensity is negligible, as described above, and the resulting signal-to-noise is high. The short half lives of the radioisotope species result in large signals relative to background levels for ease of detection and short total lifetimes for low residual effects.

When a pbar annihilates at rest on a proton it produces a number of energetic charged particles and gamma rays. These particles and gamma rays all move away radially from the annihilation site. It is possible to track these particles and gamma rays which all point back to a common point, the vertex. This is a common technique in high-energy physics to visualize the source of the radiation using vertex reconstruction. In high-energy physics, locating the vertex allows removing certain types of backgrounds and to reconstruct the physics of the event. The same can be used for visualization of a distributed source of annihilation radiation. It is described here a detector system that will allow visualizing on-line the distribution of annihilation sites produced using a pbar beam stopping in tissue.

In order to examine the detector design limitation a model is used. Assume a pbar beam penetrating and stopping at the center of a sphere of water 15 cm in radius. Assume the annihilation radiation is from the pbar-p annihilation of the proton in the hydrogen atom of the water molecule. The detector must be placed outside the sphere for the detection of the radiation products: electrons, muons, pions, kaons, and gamma rays. For this discussion, the annihilation of the pbar with an oxygen nucleus is ignored. (It would have in addition to the pions, kaons, and gamma-rays; protons, neutrons, ion fragments, and hard x-rays.)

The charged particles escaping the 15 cm will have energies greater than that given by the stopping range in 15 cm of H20 shown in table 1.

TABLE 1

Kinetic energy and momenta for particles stopping in 15 cmH20 are shown.

| Muon | Pion | Kaon | Proton |
|---|---|---|---|
| 130 MeV/c | 160 MeV/c | 350 MeV/c | 540 MeV/c |
| 80 MeV | 92 MeV | 124 MeV | 155 MeV |

The mean multiplicity of charged mesons from the annihilation site is 3, and for neutral mesons are 2. The fraction of purely neutral annihilations is 4%. The fraction of annihilations producing at least one neutral meson is >40%. The mean momenta of these mesons are about 400 MeV/c.

TABLE 2

Mean decay distances and the dominant decay products of pbar-p annihilation are given.

| Particle | Muon | Charged pion | Neutral pion | Charged kaon | Neutral kaon short | Neutral kaon long |
|---|---|---|---|---|---|---|
| $c \cdot \tau \cdot$ (cm) | $6.586 \cdot 10^4$ | 780.3 | $2.5 \cdot 10^{-6}$ | 370.9 | 2.675 | 1554 |
| Major Decay products | $e\nu\nu$ | $\mu\nu$ | $\gamma\gamma$ | $\pi \cdot \pi \cdot \pi$ $\pi \cdot \pi^0$ | $\pi \cdot \pi$ $\pi^0 \cdot \pi^0$ | $\pi^0 \cdot \pi^0 \cdot \pi^0$ $\pi \cdot \pi \cdot \pi^0$ |

Table 2. Mean decay distances and the dominant decay products of pbar-p annihilation are given.

Figure 19:
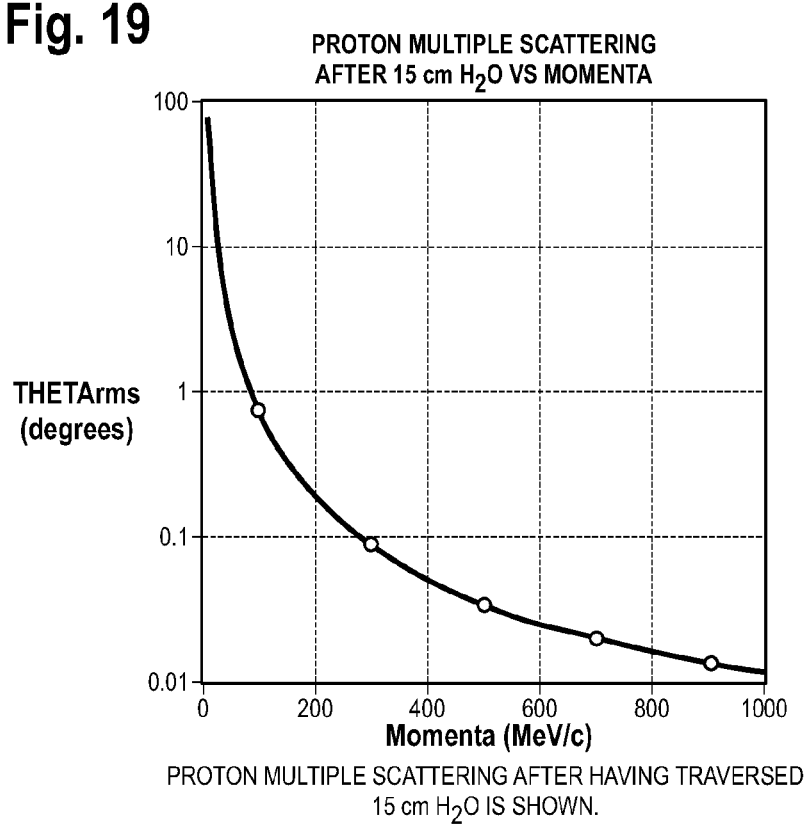
Figure 20:
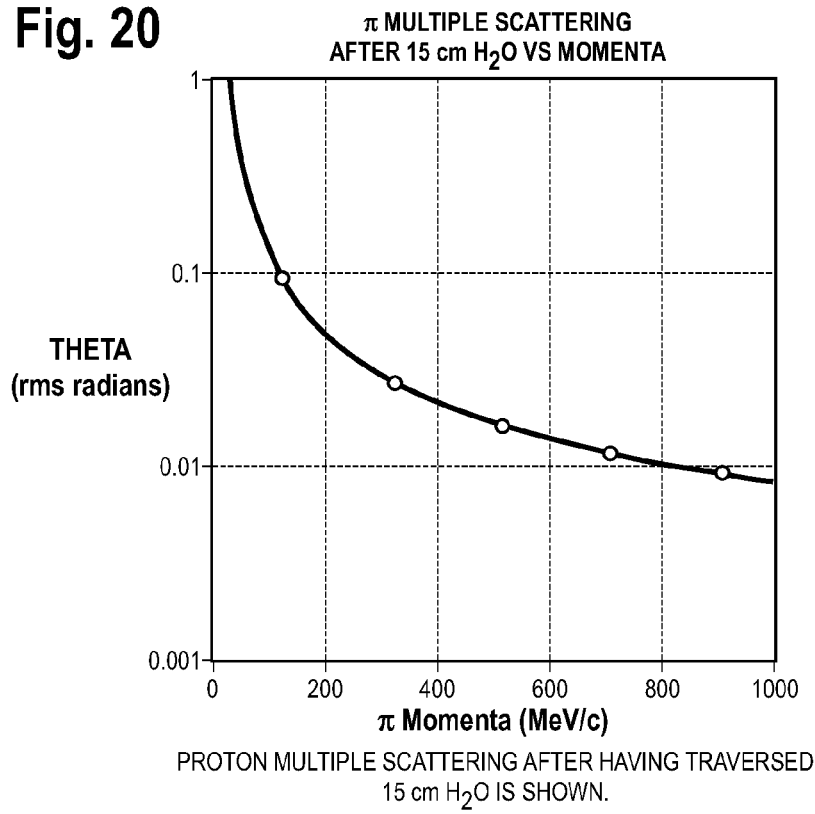

From tables 1 and 2 we see that the muons and charged pions mostly escape the 15 cm sphere. The neutral pion decays in less than 0.025 microns into a pair of gammas that escape with the energy carried by the pion. Only a fraction of the charged kaons escape the 15 cm sphere. The neutral k short decays within 2.65 cm from the primary vertex producing a secondary vertex away from the annihilation site. During the process of the charged particles traversing the 15 cm of H20, they will multiple scatter causing direction changes and therefore impacting our ability to point back to the exact annihilation site. This change of direction is given by the following expression that depends upon the momentum of the particle; it's charge, and the material through which the particle is passing.

$$\theta_0 = 13.6 \cdot \text{MeV} \cdot \frac{z \cdot \sqrt{\frac{x}{X_0}} \cdot \left(1 + 0.038 \cdot \ln\left(\frac{x}{X_0}\right)\right)}{\beta \cdot c \cdot p}$$

where
z is the charge of the particle
$X_0$ is radiation length of the material
p is the momentum of the particle in MeV/c
$\theta_0$ is the angle in radians In fact, the pbar (540 MeV/c) will scatter laterally to the direction of the beam by an rms value of about 4 mm coming to the center of the sphere. See FIG. 19. Charged pions (160 MeV/c) just reaching the surface of the sphere will have scattered laterally to the direction of the track by an rms of about 7 mm. Charged pions having momenta less than 160 MeV/e stop in the water and are not detected. This limits how precisely we can point to the vertex using detection of the charged particles. See FIG. 20.

The pions with a momentum of 300 MeV/c will scatter laterally by an rms of 2.5 mm. The highest momentum of the pions would allow between 1.5 and 2.5 mm precision of locating the annihilation vertex. Charged kaons are worse. Of course, if the site of annihilation is closer to the surface one gains in precision (3× at 1.5 em).

Multiple scattering will be the limiting error for visualization of the geometry of annihilation sites. One cannot hope for better than 1.5 mm precision for viewing annihilation geometry located under 15 cm of H20 using charged pion tracking.

An alternative route to visualization would be to use the neutral pions. They decay to a pair of gammas sharing a total energy of 134.97 MeV plus the momentum of the neutral pion. The pair of gammas points back to the position at which the pion decayed. The gammas have a high probability of escaping the 15 em without interacting. The gamma rays can be detected in a high z, high-density media, where they interact creating an electromagnetic shower. The shower energy is contained (95%) inside a cylinder of radius 2×RM, the Moliere radius, and a length of about 20 XO radiation lengths.

TABLE 3

Some physical properties of three selected materials used for shower detection are shown.

| Material | NaI(T1) | PbWO$_4$ | W |
|---|---|---|---|
| Radiation Length (cm) | 2.59 | 0.89 | 0.323 |
| Moliere Radius cm | 4.5 | 2.2 | 0.8 |
| dE/dx (MeV/cm) per mip | 4.8 | 13.0 | 24.0 |
| Decay time (ns) | 250 | 5-15 | — |
| Relative light output | 1. | 0.01 | — |

Figure 21:
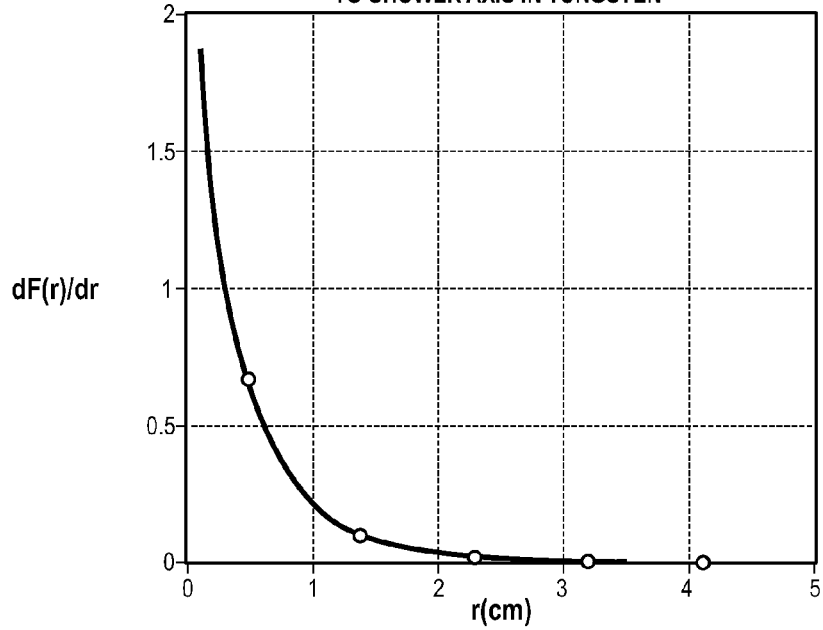

In fact, the lateral distribution of the shower relative to the shower axis is quite peaked on the shower axis. Moliere has calculated this distribution. An analytical approximation to Moliere's calculation is given for r 1 RM<1:

$$\frac{dF}{dr} = 2.85 \cdot (1 + 4 \cdot r) e^{-4 \cdot (r)^{\frac{2}{3}}}$$

where
$R_M = (E_s/\epsilon) \cdot X_0$, the Moliere radius
$X_0$ is the radiation length for the material
$E_s = 21$ MeV
$\epsilon$ is the critical energy, 610 MeV/(Z+1.24), 8.1 MeV for W In FIG. 21, the radial distribution of energy relative to the shower axis for tungsten is shown. Another material having a similar Moliere radius and density is uranium. These materials are not actively sensitive to the shower and would require a sandwich type of construction using layers of tungsten and scintillator. The design has been employed before but not for the purpose of localizing the shower axis. Single points on the shower axis have been localized to about 1 mm using this idea.

We would want multiple points along the shower axis thus giving a vector pointing back to the vertex for each gamma (coming from pi zero decay). The mean number of gammas is four for each annihilation in pbar-p and can be as many as 10. Thus, we should be able to take a cross over point to give the vertex point for the image.

The size of the sensing element for the shower is determined by the Moliere radius, 3.23 mm. Depending upon backgrounds and gamma multiplicity one would either use a 3.23×3.23×3.23 mm3 in a matrix or a crossed 3.23×3.23×200 mm3 hodoscope plastic scintillator array to sample the shower's charged particles passing between sandwich plates. One can aim for 500-micron precision in location of the vertex using this technique.

Figure 22:
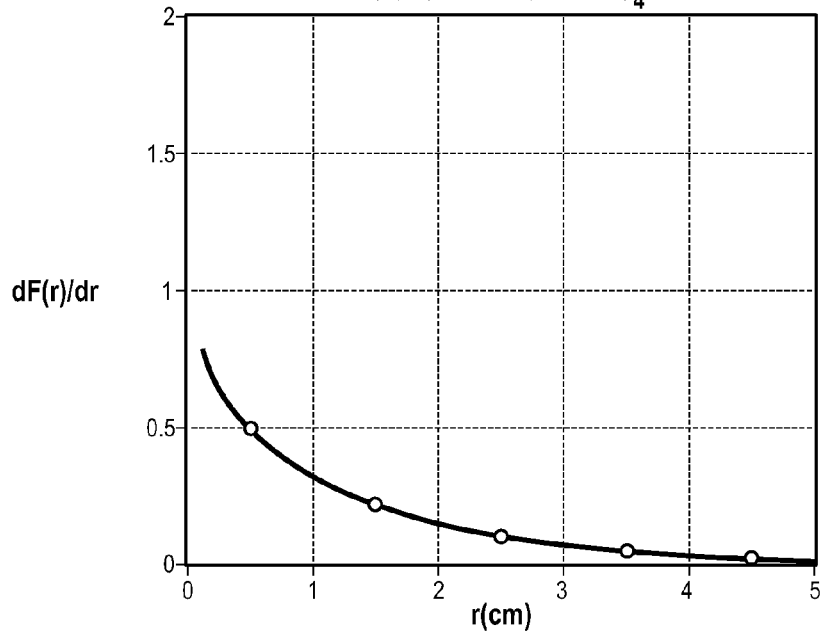

In FIG. 22, the radial distribution of energy relative to the shower axis for PbW04 is shown. This material is a scintillator, see table 3 for some of its properties. The radiation length of PbW04 is 2.7× larger than that of tungsten. One could use a 9×9×9 mm3 in a matrix or a crossed 9×9×200 mm3 hodoscope's sensor array to sample the shower charged particles. These two detector alternatives would have to be studied and compared before one could decide on the better choice. In each case, one would tag the charged particles in an active layer before the shower detector. Either case would be better than using the charged particle tracks.

One important consideration, which favors smaller shower localization of tungsten over PbW04, is its ability to separate the gamma pair of the 0 decay. The opening angle of the gamma pair from the 0 decay is given in the laboratory reference frame as:

$$\cos \phi = 1 - (1+R)^2/2R\gamma^2$$

where $$R = E_1/E_2, R \leq 1$$

$$\gamma = E_\pi/m_\pi$$

Figure 23:
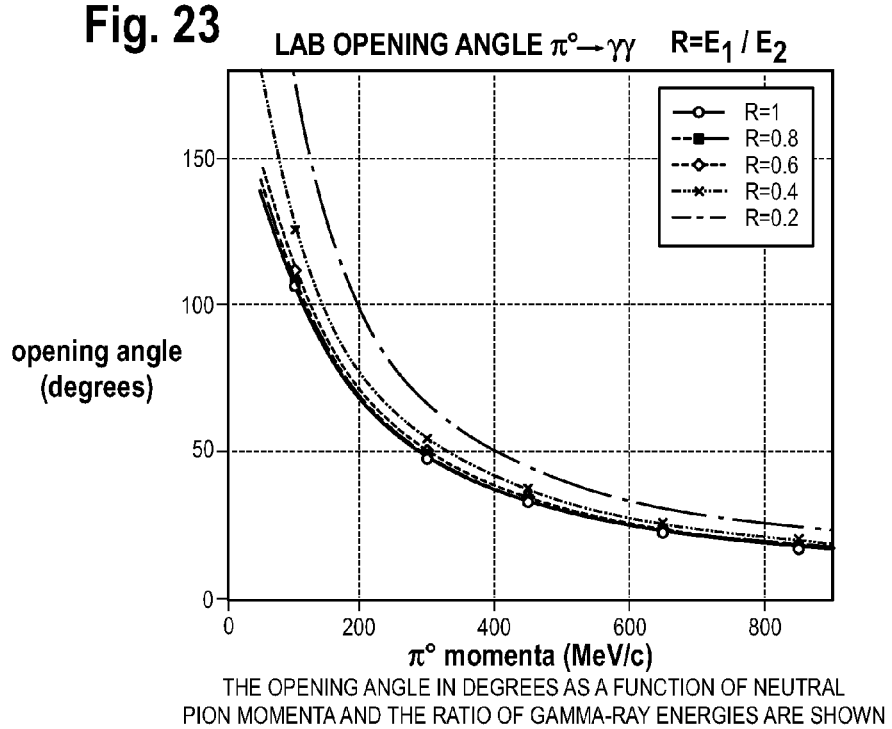
Figure 24:
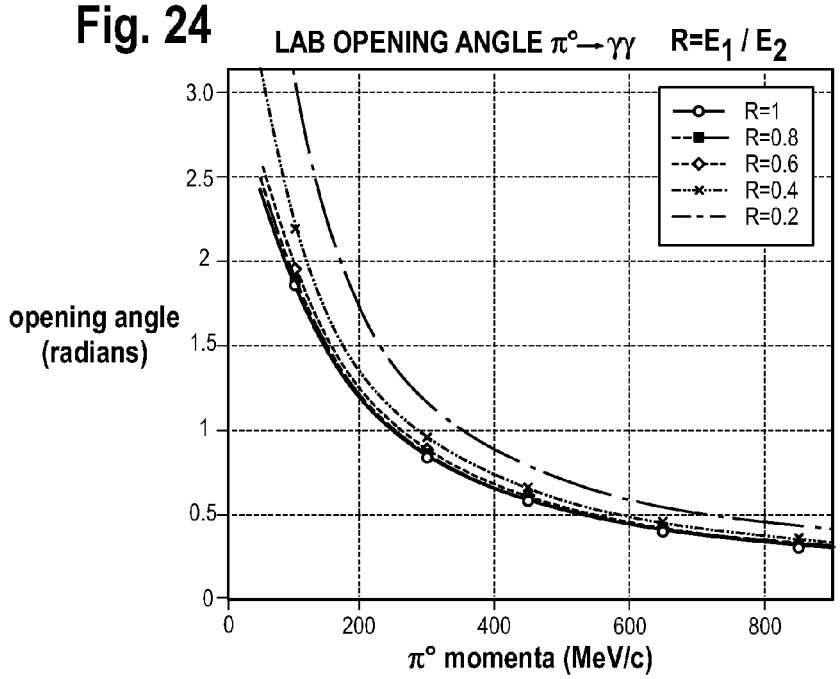

The opening angle of the neutral pion decay is plotted as a function of the 0 momentum. See FIGS. 23 and 24.

The smallest opening angle we should expect is 16 degrees (5 cm separation at 15 cm from annihilation site). However, the average opening angle will be around 40 degrees (9 cm separation at 15 cm from the annihilation site). The PbW04 would loose some efficiency in separating the decay gammas as compared to the tungsten shower detector at the higher pion momenta.

It should be clear that a shower detector would be quite massive (>400 lbs for steradians).

Two techniques for localizing the proton-antiproton annihilation site have been examined for the case where the site is at the center of a 30 cm diameter sphere of water. Tracking charged pions beyond the sphere is limited to >1.5 mm precision on the vertex reconstruction due to multiple scattering in traversing the 15 cm of water. Pointing of the shower axis from neutral pion decays is expected to yield a vertex localization precision of <0.5 mm. The shower detection can be done using fast scintillator <<15 ns) allowing a faster response than the charged particle tracking.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods and build systems in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. A method for treating a patient having a plurality of undesirable cells, comprising:
   inserting a plurality of antiprotons into an accelerator;
   controlling said accelerator so as to control temperature of said antiprotons while accelerating said antiprotons to a predetermined, therapeutic energy level;
   extracting said antiprotons from said accelerator at said therapeutic energy level; and
   exposing at least a portion of the plurality of the undesirable cells to said antiprotons at said therapeutic energy level.

2. The method of claim 1, wherein the exposing is carried out with said undesired cells being cancerous cells.

3. The method of claim 1, further comprising monitoring said antiprotons during said accelerating.

4. The method of claim 3, further comprising monitoring current of said antiprotons during said accelerating.

5. The method of claim 1, wherein the controlling includes adjusting magnetic field in dipole correctors during said accelerating.

6. The method of claim 1, wherein the controlling includes adjusting phase and amplitude of a radio-frequency cavity through which the antiprotons pass during said accelerating.

7. The method of claim 1, wherein said controlling includes adjusting electromagnetic field frequency of a radio-frequency cavity through which the antiprotons pass during said accelerating, said adjusting carried out such that said frequency matches an integer multiple of revolution frequency of said antiprotons during said accelerating.

8. The method of claim 1, further including generating radioisotopes within said patient with said antiprotons in carrying out imaging and therapeutic treatment.

9. A method for treating a patient, comprising:
   inserting a plurality of antiprotons into an accelerator;
   controlling said accelerator so as to control temperature of said antiprotons while accelerating said antiprotons to a predetermined, irradiation energy level;
   extracting said antiprotons from said accelerator at said irradiating energy level;
   irradiating at least a portion of the patient body to said antiprotons at said irradiating energy level;
   generating radioisotopes within said body by irradiating with said antiprotons; and
   providing patient therapy with said radioisotopes.

10. A method for imaging a patient, comprising:
   inserting a plurality of antiprotons into an accelerator;
   controlling said accelerator so as to control temperature of said antiprotons while accelerating said antiprotons to a predetermined, irradiation energy level;
   extracting said antiprotons from said accelerator at said irradiating energy level;
   irradiating at least a portion of the patient body to said antiprotons at said irradiating energy level;
   generating radioisotopes within said body by irradiating with said antiprotons; and
   providing patient imaging with said radioisotopes.

* * * * *